(12) United States Patent
Barbion et al.

(10) Patent No.: US 11,865,118 B2
(45) Date of Patent: Jan. 9, 2024

(54) HETEROCYCLIC COMPOUNDS AND THEIR USE IN PREVENTING OR TREATING BACTERIAL INFECTIONS

(71) Applicant: MUTABILIS, Romainville (FR)

(72) Inventors: Julien Barbion, Sannois (FR); Audrey Caravano, Enghien les Bains (FR); Sophie Chasset, Nandy (FR); Francis Chevreuil, Chantilly (FR); Frédéric Le Strat, Combs la Ville (FR); Christophe Simon, Chevilly Larue (FR); Julie Brias, Paris (FR); Rémi Lebel, Drancy (FR)

(73) Assignee: MUTABILIS, Romainville (FR)

( * ) Notice: Subject to any disclaimer, the term of this patent is extended or adjusted under 35 U.S.C. 154(b) by 208 days.

(21) Appl. No.: 17/263,662

(22) PCT Filed: Jul. 29, 2019

(86) PCT No.: PCT/EP2019/070368
§ 371 (c)(1),
(2) Date: Jan. 27, 2021

(87) PCT Pub. No.: WO2020/025543
PCT Pub. Date: Feb. 6, 2020

(65) Prior Publication Data
US 2021/0275542 A1    Sep. 9, 2021

(30) Foreign Application Priority Data

Jul. 30, 2018 (EP) .................. 18306026

(51) Int. Cl.
| | |
|---|---|
| A61K 31/551 | (2006.01) |
| A61P 31/04 | (2006.01) |
| A61K 31/407 | (2006.01) |
| A61K 31/427 | (2006.01) |
| A61K 31/43 | (2006.01) |
| A61K 31/431 | (2006.01) |
| A61K 31/545 | (2006.01) |
| A61K 31/546 | (2006.01) |
| C07D 495/18 | (2006.01) |
| C07D 513/18 | (2006.01) |

(52) U.S. Cl.
CPC .......... *A61K 31/551* (2013.01); *A61K 31/407* (2013.01); *A61K 31/427* (2013.01); *A61K 31/43* (2013.01); *A61K 31/431* (2013.01); *A61K 31/545* (2013.01); *A61K 31/546* (2013.01); *A61P 31/04* (2018.01); *C07D 495/18* (2013.01); *C07D 513/18* (2013.01)

(58) Field of Classification Search
CPC .............................. A61K 31/551; A61P 31/04
See application file for complete search history.

(56) References Cited

U.S. PATENT DOCUMENTS

| | | | | |
|---|---|---|---|---|
| 7,439,253 | B2 * | 10/2008 | Lampilas ............. | C07D 471/08 514/293 |
| 2005/0245505 | A1 | 11/2005 | Aszodi et al. | |

FOREIGN PATENT DOCUMENTS

| | | | |
|---|---|---|---|
| JP | 2005518333 A | 6/2005 | |
| JP | 2006512335 A | 4/2006 | |
| JP | 2012504593 A | 2/2012 | |
| JP | 2018510198 A | 4/2018 | |
| WO | 2004052891 A1 | 6/2004 | |
| WO | WO-2004052891 A1 * | 6/2004 | ............. A61P 11/00 |
| WO | 2014141132 A1 | 9/2014 | |
| WO | 2017109025 A1 | 6/2017 | |

* cited by examiner

*Primary Examiner* — Craig D Ricci
*Assistant Examiner* — Janet L Coppins
(74) *Attorney, Agent, or Firm* — Thompson Coburn LLP; Steven M. Ritchey

(57) ABSTRACT

The present invention relates to compounds of formula (I) and their use for treating or preventing a bacterial infection or as an antibacterial agent and/or as a β-lactamase inhibitor.

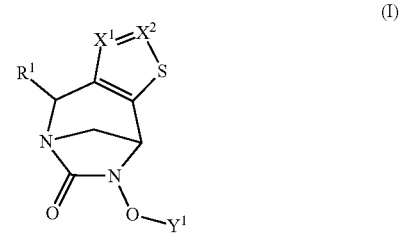

17 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2019/070368 filed on Jul. 29, 2019, claiming the benefit of European Application No. 18306026.8, filed on Jul. 30, 2018, both of which are incorporated herein by reference in their entireties.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

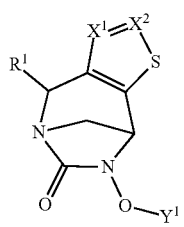

(I)

wherein:

$R^1$ is chosen in the group consisting of H, $(CH_2)_m CN$, $(CH_2)_m C(=O)NR^2R^3$, $(CH_2)_m C(=O)NR^4NR^2R^3$, $(CH_2)_m C(=O)NR^2OR^3$, $(CH_2)_n OR^2$, $(CH_2)_n NR^2R^3$, $(CH_2)_n NR^4C(=NR^4)N(R^4)_2$, $(CH_2)_m C(=NOZ^4)NZ^1Z^2$, or $(CH_2)_n$-(5 to 6-membered)heteroaryl comprising 1 or 4 heteroatoms independently chosen in the group consisting of N, O or S;

m is an integer comprised between 0 and 6;

n is an integer comprised between 1 and 6;

$R^2$ and $R^3$, identical or different, are chosen in the group consisting of H, linear or branched (C1-C6)alkyl, (C3-C11)cycloalkyl, (C6-C10)aryl, (4 to 6-membered)heterocyclyl comprising 1 or 2 heteroatoms independently chosen in the group consisting of N, O or S, (5 to 10-membered)heteroaryl comprising from 1 to 4 heteroatom independently chosen in the group consisting of N, O or S, $C(=O)(C1-C6)alkyl$, $C(=O)(4$ to 6-membered)heterocyclyl comprising 1 or 2 heteroatoms independently chosen in the group consisting of N, O or S, or form together with the nitrogen atom to which they are linked a (4 to 6-membered)heterocyclyl comprising 1 or 2 heteroatom independently chosen in the group consisting in N, O or S; wherein the alkyl, cycloalkyl, aryl, heterocyclyl and heteroaryl are optionally substituted by one or more $R^5$;

$R^4$, each identical or different, is independently chosen in the group consisting of H and linear or branched (C1-C6) alkyl optionally substituted by one or more $R^5$;

$R^5$, each identical or different, is chosen in the group consisting of OH, O(C1-C6)alkyl, $NH_2$, $NH(C1-C6)$alkyl, $N[(C1-C6)alkyl]_2$, $C(=O)NH_2$, $C(=O)NH_2$, $C(=O)NH$ (C1-C6)Alkyl, $C(=O)N[C1-C6)Alkyl]_2$;

$Y^1$ is chosen in the group consisting of $SO_3H$, $CHFC$ $(=O)Y^2$ and $CF_2C(=O)Y^2$, $SO_3(C1-C6)alkyl-C(=O)O$ (C1-C6)alkyl;

$Y^2$ is chosen in the group consisting of OH, O (C1-C6) alkyl linear or branched, O(C3-C11)cycloalkyl, O-(4 to 6-membered)heterocyclyl comprising 1 or 2 heteroatom independently chosen in the group consisting of N, O and S; $NY^3Y^4$, wherein the alkyl, cycloalkyl and heterocyclyl are optionally substituted by one or more $Y^5$;

$Y^3$ and $Y^4$, each identical or different, is chosen in the group consisting of linear or branched (C1-C6)alkyl, linear or branched O(C1-C6)alkyl, (C3-C11)cycloalkyl, (4 to 6-membered)heterocyclyl comprising 1 or 2 heteroatoms independently chosen in the group consisting of N, O or S, or form together with the nitrogen atom to which they are linked a (4 to 6-membered)heterocyclyl comprising 1 or 2 heteroatoms independently chosen in the group consisting of N, O or S; wherein the alkyl, cycloalkyl and heterocyclyl is optionally substituted by one or more $Y^5$;

$Y_5$, each identical or different, is chosen in the group consisting of linear or branched (C1-C6)alkyl, (C3-C6) cycloalkyl, linear or branched O(C1-C6)alkyl, linear or branched O(C1-C6)alkyl-O(C1-C6)alkyl, linear or branched (C1-C6)alkyl-O(C1-C6)alkyl; and O(C3-C6)cycloalkyl;

$X^1=X^2$ is chosen in the group consisting of $N=CX^4$, $CX^3=N$, $CX^3=CX^4$, $CX^3=CA^1$ and $CA^1=CX^4$;

$A^1$ is chosen in the group consisting of H, halogen, linear or branched (C1-C6)alkyl, $(CH_2)_m-C(=O)NA^2A^3$, $(CH_2)_n-NA^2A^3$, $(CH_2)_m$-phenyl, $(CH_2)_m$-(5 to 6-membered heteroaryl comprising from 1 to 4 heteroatoms independently chosen in the group consisting of N,O,S), wherein the alkyl is optionally substituted by one or more OH, CN and/or halogen and the phenyl and heteroaryl are optionally substituted by one or more halogen, linear or branched (C1-C6)alkyl, linear or branched (C1-C6)alkoxy, $CF_3$;

$A^2$ and $A^3$, each identical or different is chosen in the group consisting of H, linear or branched (C1-C6)alkyl, linear or branched O—(C1-C6)alkyl;

$X^3$ and $X^4$, each identical or different, is chosen in the group consisting of $(CH_2)_m-C(=O)NX^6X^7$, $(CH_2)_m-C(=O)NX^6OX^7$, $(CH_2)_m-C(=O)NX^6NX^7X^8$, $(CH_2)_m-C(=NOX^6)X^7$, $(CH_2)_m-C(=NX^6)NHX^7$, $(CH_2)_m-NX^6X^7$, $(CH_2)_n-NX^6C(=O)X^7$, $(CH_2)_n-NX^6C(=O)NX^7X^8$, $(CH_2)_n-NX^6S(=O)_2NX^7X^8$, $(CH_2)_n-NX^6S(=O)_2X^7$, $(CH_2)_n-NHC(=NX^6)NHX^7$, $(CH_2)_n-NHC$ (=NX⁶)X⁷, (CH₂)ₙ—OX⁶, (CH₂)ₘ—S(=O)₂NX⁶X⁷, (CH₂)ₘ—(C3-C6)cycloalkyl, (CH₂)ₘ-phenyl, (CH₂)ₘ-(5 to 6-membered heteroaryl comprising from 1 to 4 heteroatom independently chosen in the group consisting of N, O, S), (CH₂)ₘ-(4 to 6-membered heterocyclyl comprising from 1 to 2 heteroatom independent chosen in the group consisting of N,O,S), wherein the cycloalkyl is optionally substituted by halogen and the phenyl and heteroaryl is substituted at least by one or more Z³ and the heterocyclyl is optionally substituted by Z³;

X⁵, each identical or different, is chosen in the group consisting of linear or branched (C1-C6)alkyl, linear or branched (C2-C6)alkyl-NZ¹Z², linear or branched (C2-C6)alkyl-NH—C(=NZ¹)NHZ², linear or branched (C2-C6)alkyl-NH—C(=NZ¹)H, linear or branched (C2-C6)alkyl-NZ₁C(=O)Z², linear or branched (C2-C6)alkyl-OZ¹, linear or branched (C1-C6)alkyl-C(=NZ¹)NHZ², linear or branched (C1-C6)alkyl-CONZ¹Z², linear or branched (C1-C6)alkyl-COOZ¹, (CH₂)ₘ-aryl, (CH₂)ₘ-(4 to 6-membered heterocyclyl comprising from 1 to 2 heteroatom independently chosen in the group consisting of N,O,S), (CH₂)ₘ-(5 to 6-membered heteroaryl comprising from 1 to 4 independently heteroatom chosen in the group consisting of N,O,S), wherein the aryl, heterocyclyl and heteroaryl are optionally substituted by one or more halogen or Z⁵;

X⁶, X⁷ and X⁸, each identical or different, are chosen in the group consisting of H, linear or branched (C1-C6)alkyl, (C6-C10)aryl, (C7-C11)aralkyl, linear or branched (C1-C6)alkyl-Z³, (C6-C10)aryl-Z³, (C7-C11)aralkyl-Z³, (CH₂)ₘ-(5 to 6-membered heteroaryl comprising from 1 to 4 heteroatom independently chosen in the group consisting of N,O,S), (CH₂)ₘ-(4 to 6-membered heterocyclyl comprising from 1 to 2 heteroatom independently chosen in the group consisting of N,O,S) or form together with the nitrogen atom to which they are linked a 4 to 6-membered heterocyclyl comprising 1 or 2 heteroatoms independently chosen in the group consisting of N, O or S, wherein the heteroaryl and heterocyclyl are optionally substituted by Z³;

Z¹ and Z², each identical or different are chosen in the group consisting of H, linear or branched (C1-C6)alkyl; wherein the alkyl is optionally substituted by one or more halogen or Z⁵;

Z³, each identical or different, is chosen in the group consisting of (CH₂)ₘ—(C6-C10)aryl-Z⁴, (CH₂)ₘ-(5 to 6-membered heteroaryl comprising from 1 to 4 heteroatom independently chosen in the group consisting of N,O,S)—Z⁴, (CH₂)ₘ-(4 to 6-membered heterocyclyl comprising 1 or 2 heteroatoms independently chosen in the group consisting of N, O or S)—Z⁴, (CH₂)ₙ—OZ¹, OZ⁵, (CH₂)ₘ—NZ¹Z², (CH₂)ₘ—C(=O)NZ¹Z², (CH₂)ₘ—NZ¹C(=O)Z², (CH₂)ₘ—NHC(=NH)Z¹, (CH₂)ₘ—NHC(=NH)NHZ¹;

Z⁴, each identical or different, is chosen in the group consisting of H and linear or branched (C1-C6)alkyl, wherein the alkyl is optionally substituted by one or more halogen or Z⁵;

Z⁵, each identical or different, is chosen in the group consisting of H, (CH₂)ₚ—OH, (CH₂)ₚ—NH₂, (CH₂)ₚ—CONH₂, (CH₂)ₚ—NHC(=NH)NH₂, p is an integer chosen among 2, 3, 4, 5 or 6;
any sulphur atom present within a heterocycle can be oxidized to form a S=O group or a S(O)₂ group;
any nitrogen atom present within a heterocycle or present within group wherein it is trisubstituted thus forming a tertiary amino group, can be further quaternized by a methyl group;

and a racemate, an enantiomer, a diastereoisomer, a geometric isomer or a pharmaceutically acceptable salt thereof, with the exception that if one of X³ or X⁴ represent (CH₂)ₘ—C(=O)NX⁶X⁷, (CH₂)ₘ—C(=O)NX⁶OX⁷ or (CH₂)ₙ—NX⁶X⁷ then at least one of X⁶ or X⁷ is different from H, (C1-C6)alkyl, (C6-C10)aryl, (C7-C11)aralkyl or (C1-C6)alkyl-pyridyl.

Preferably,

R¹ is chosen in the group consisting of H, (CH₂)ₘCN, (CH₂)ₘC(=O)NR²R³, (CH₂)ₘC(=O)NR⁴NR²R³, (CH₂)ₘC(=O)NR²OR³, (CH₂)ₙOR², (CH₂)ₙNR²R³, (CH₂)ₙNR⁴C(=NR⁴)N(R⁴)₂, (CH₂)ₙ—(5 to 6-membered)heteroaryl comprising 1 or 4 heteroatoms independently chosen in the group consisting of N, O or S, and/or Y¹ is chosen in the group consisting of SO₃H, CHFC(=O)Y² and CF₂C(=O)Y².

The present invention also relates to a compound of formula (I*)

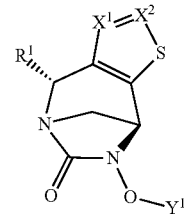

(I*)

wherein R¹, X¹, X² and Y¹ are as defined for compounds of formula (I).

Preferably, among the compounds of formula (I), the invention relates to compounds of formula (IA) or (IA*):

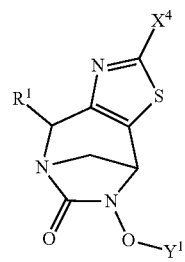

(IA)

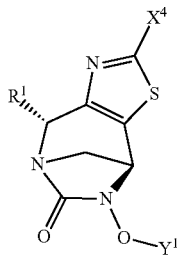

(IA*)

wherein R¹, X⁴ and Y¹ are as defined for compounds of formula (I) above.

Preferably, among the compounds of formula (I), the invention relates to compounds of formula (IB) or (IB*)

Preferably, among the compounds of formula (I), the invention relates to compounds of formula (ID) or (ID*)

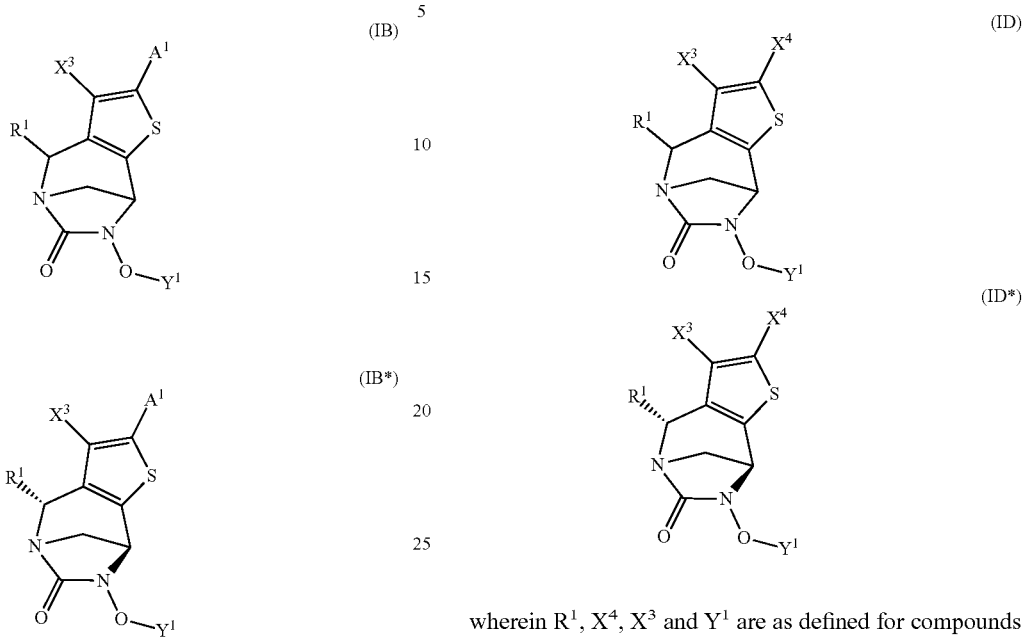

wherein $R^1$, $X^3$, $A^1$ and $Y^1$ are as defined for compounds of formula (I) above.

Preferably, among the compounds of formula (I), the invention relates to compounds of formula (IC) or (IC*)

wherein $R^1$, $X^4$, $X^3$ and $Y^1$ are as defined for compounds of formula (I) above.

Preferably, among the compounds of formula (I), the invention relates to compounds of formula (IE) or (IE*):

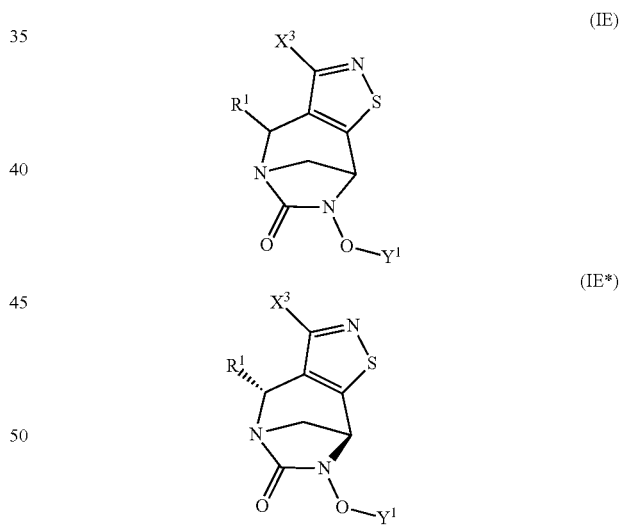

wherein $R^1$, $X^3$ and $Y^1$ are as defined for compounds of formula (I) above.

Preferably, in the compounds of the invention of formula (I), (I*), (IA), (IA*), (IB), (IB*), (IC), (IC*), (ID), (ID*), (IE), (IE*), $R^1$ is chosen in the group consisting of H, CN, C(=O)NR$^2$R$^3$, C(=O)NHNHR$^2$, C(=O)NHOR$^2$, CH$_2$OR$^2$, CH$_2$NHR$^2$, CH$_2$NR$^4$C(=NR$^4$)N(R$^4$)$_2$, C(=NOZ$^4$)NZ$^1$Z$^2$, CH$_2$-(5 to 6 membered)heteroaryl comprising 1 or 4 heteroatoms independently chosen in the group consisting of N, O or S;

wherein $R^1$, $X^4$, $A^1$ and $Y^1$ are as defined for compounds of formula (I) above.

$R^2$ and $R^3$, each identical or different, are chosen in the group consisting of H, linear or branched (C1-C6)alkyl, (4 to 6-membered)heterocyclyl comprising 1 or 2 heteroatoms independently chosen in the group consisting of N, O or S, C(=O)(4 to 6-membered heterocyclyl comprising 1 or 2 heteroatoms independently chosen in the group consisting of N, O or S);

$R^4$, each identical or different, is independently chosen in the group consisting of H, linear or branched (C1-C6)alkyl, wherein the alkyl is optionally substituted by one or more $R^5$;

$R^5$, each identical or different, is chosen in the group consisting of OH, O(linear or branched-C1-C6)alkyl, $NH_2$, NH(linear or branched C1-C6)alkyl, N[(linear or branched C1-C6)Alkyl]$_2$, C(=O)$NH_2$, C(=O)NH(linear or branched C1-C16)alkyl, C(=O)N[linear or branched (C1-C6)alkyl]$_2$;

$Y^2$ is chosen in the group consisting of OH, O(C1-C6) alkyl linear or branched, O-(4 to 6-membered)heterocyclyl comprising 1 or 2 independently heteroatom chosen in the group consisting of N, O and S; wherein the alkyl, heterocyclyl are optionally substituted by one or more $Y^5$;

$Y^5$, each identical or different, is chosen in the group consisting of linear or branched (C1-C6)alkyl, (C3-C6) cycloalkyl, linear or branched O(C1-C6)alkyl, linear or branched O(C1-C6)alkyl-O(C1-C6)alkyl, linear or branched (C1-C6)alkyl-O(C1-C6)alkyl; and O(C3-C6)cycloalkyl;

$X^1=X^2$ is chosen in the group consisting of $N=CX^4$, $CX^3=CX^4$, $CX^3=CA^1$ and $CA^1=CX^4$.

Preferably, $R^1$ is chosen in the group consisting of H, CN, C(=O)$NR^2R^3$, C(=O)$NHNHR^2$, C(=O)$NHOR^2$, $CH_2OR^2$, $CH_2NHR^2$, $CH_2NR^4C(=NR^4)N(R^4)_2$, $CH_2$-(5 to 6 membered)heteroaryl comprising 1 or 4 heteroatoms independently chosen in the group consisting of N, O or S.

In one preferred embodiment, the present invention relates to compounds of formula (IA) or (IA*):

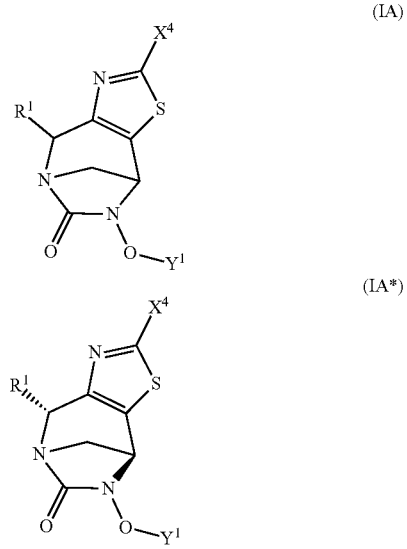

wherein
$R^1$ is H;
$X^4$ is $(CH_2)_m$—C(O)—NH—$(C_1-C_3)$alkyl-$NH_2$, $(CH_2)_n$—NH—C(=NH)—$NH_2$ or $(CH_2)_m$—C(O)—NH—$(C_1-C_3)$alkyl-NH—C(=NH)—$NH_2$;
$Y^1$ is as defined for compounds of formula (I) above.
Preferably in this embodiment $Y^1$ is $SO_3H$, $CF_2COOH$.

In one embodiment $Y^2$ represents O—$CY^6Y^7Y^8$ wherein $Y^6$, $Y^7$ and $Y^8$, identical or different, represent (C1-C3)-alkyl, (C3-C6)-cycloalkyl, (C4-C8)-heterocycloalkyl comprising from 1 to 2 heteroatoms chosen among N—$Y^{10}$, O or S, a group $CH_2$—O—(C1-C3)-alkyl, or a group $CH_2$—O—$(CH_2)_2$—O—(C1-C3)-alkyl, wherein the alkyl, cycloalkyl and heterocycloalkyl is optionally substituted by one or more $Y^9$; or $Y^6$ and $Y^7$ could form together with the carbon atom to which they are linked a (C3-C6)-cycloalkyl or a (C4-C8)-heterocycloalkyl comprising from 1 to 2 heteroatoms chosen among N—$Y^{10}$, O or S, wherein the cycloalkyl and heterocycloalkyl is optionally substituted by one or more $Y^9$;

$Y^{10}$ represents (C1-C6)-alkyl, (C3-C6)-cycloalkyl, C(=O)(C1-C6)-alkyl or C(=O)(C3-C6)-cycloalkyl;

$Y^9$ represents (C1-C6)-alkyl, (C3-C6)-cycloalkyl, O(C1-C6)-alkyl or O(C3-C6)-cycloalkyl.

In one embodiment, in the compounds of the invention $Y^2$ is chosen among

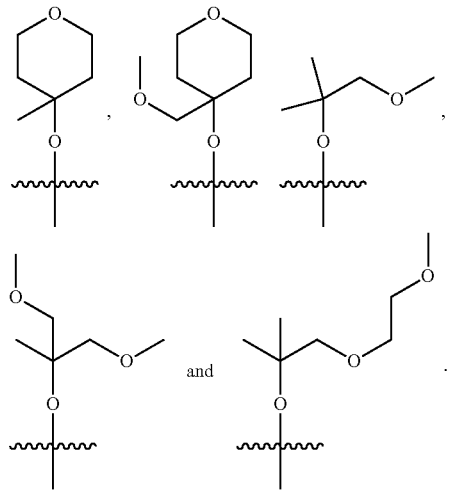

and

The term "alkyl", as used herein, refers to an aliphatic-hydrocarbon group which may be straight or branched, having 1 to 6 carbon atoms in the chain unless specified otherwise.

Preferred alkyl groups have 1 or 2 carbon atoms in the chain. Specific examples of alkyl groups include, but are not limited to, methyl, ethyl, n-propyl, isopropyl. Preferably, the alkyl group is methyl or ethyl.

The term "cycloalkyl" refers to a saturated monocyclic or bicyclic non-aromatic hydrocarbon ring of 3 to 11 carbon atoms, preferably 3 to 4 carbon atoms, which can comprise one or more unsaturation. Specific examples of monocyclic cycloalkyl groups include cyclopropyl, cyclobutyl, cyclopentyl, cyclopentenyl, cyclohexyl, cyclohexenyl. Preferably, the cycloalkyl group is cyclopropyl or cyclobutyl.

Aryl relates to an aromatic mono or bicycle comprising from 6 to 10 carbon atom. An example of aryl is phenyl, naphtyl, preferably phenyl.

The term "heterocyclyl", as used herein and without contrary definition specifically mentioned, either alone or in combination with another radical, refers to a monocyclic saturated or partially unsaturated non-aromatic ring containing from 4 to 6 atom, of which at least one atom, preferably 1 or 2 atom, of the ring is a heteroatom such as N, O, S, S(O) or S(O)$_2$. Preferably, the heterocycle is a monocyclic saturated or partially unsaturated non-aromatic ring containing from 4 to to 6 atom of which at least one atom, preferably 1 or 2 atom, of the ring is a heteroatom such as N, O, S, S(O) or S(O)2. The carbon atoms of the heterocyclyl can also be oxidized to form a C(O) group. Suitable heterocycles are also disclosed in the Handbook of Chemistry and Physics, 76th Edition, CRC Press, Inc., 1995-1996, pages 2-25 to 2-26. Exemplary heterocyclyl groups include but are not limited to azetidinyl, oxetanyl, oxazolyl, oxazolidinyl, oxadiazolyl, pyrrolyl, pyrrolidinyl, pyridyl, dihydropyridinyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, dihydropyranyl, tetrahydropyranyl. Without contrary definition specifically mentioned, the heterocyclyl can be carbon or nitrogen linked.

Heteroaryl as used herein and without contrary definition specifically mentioned, either alone or in combination with another radical, refers to an aromatic monocyclic heterocyclyl ring comprising from 5 to 6 atoms of which at least one atom, preferably from 1 to 4 atom, of the ring is a heteroatom such as N, O, S, S(O) or S(O)2.. Without contrary definition specifically mentioned, the heteroaryl can be carbon or nitrogen linked. Examples of heteroaryl are furanyl, imidazolyl, isothiazolyl, isoxazolyl, oxazolyl, pyrazinyl, pyrazolyl, pyridazinyl, pyrimidinyl, pyridinyl, pyrrolyl, tetrazolyl, thiadiazolyl, thiazolyl, thienyl, triazolyl, etc.

Moreover some compounds according to this invention may contain a basic amino group and thus may form an inner zwitterionic salt (or zwitterion) with the acidic group —$OSO_3H$, —$OCFHCO_2H$ or —$OCF_2CO_2H$ and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be utilized as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids or aminohydroxyl-O-sulfonic acid; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, PA, 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p.1-19 (1977).

Compounds according to the invention also include isotopically-labelled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2H$, $^3H$, $^{11}C$, $^{13}C$, $^{14}C$, $^{18}F$, $^{13}N$, $^{15}N$, $^{33}S$, $^{34}S$, $^{35}S$, $^{36}S$, $^{17}O$ or $^{18}O$. Isotopically-labelled compounds are useful in drug and/or substrate tissue distribution studies. Substitution with heavier isotopes such as deuterium ($^2H$) affords greater metabolic stability (for example increased in vivo half-life or reduced dosage requirements). Isotopically-labelled compounds are prepared by any suitable method or by processes using an appropriate isotopically-labelled reagent in replacement of the non-labelled reagent otherwise employed.

The invention provides compounds having antibacterial properties and/or compounds acting as β-lactamase inhibitors.

The invention also provides a process for the preparation of a compound according to the invention.

The compounds of the present invention of formula (I) can be prepared by the following reaction Schemes 1-9.

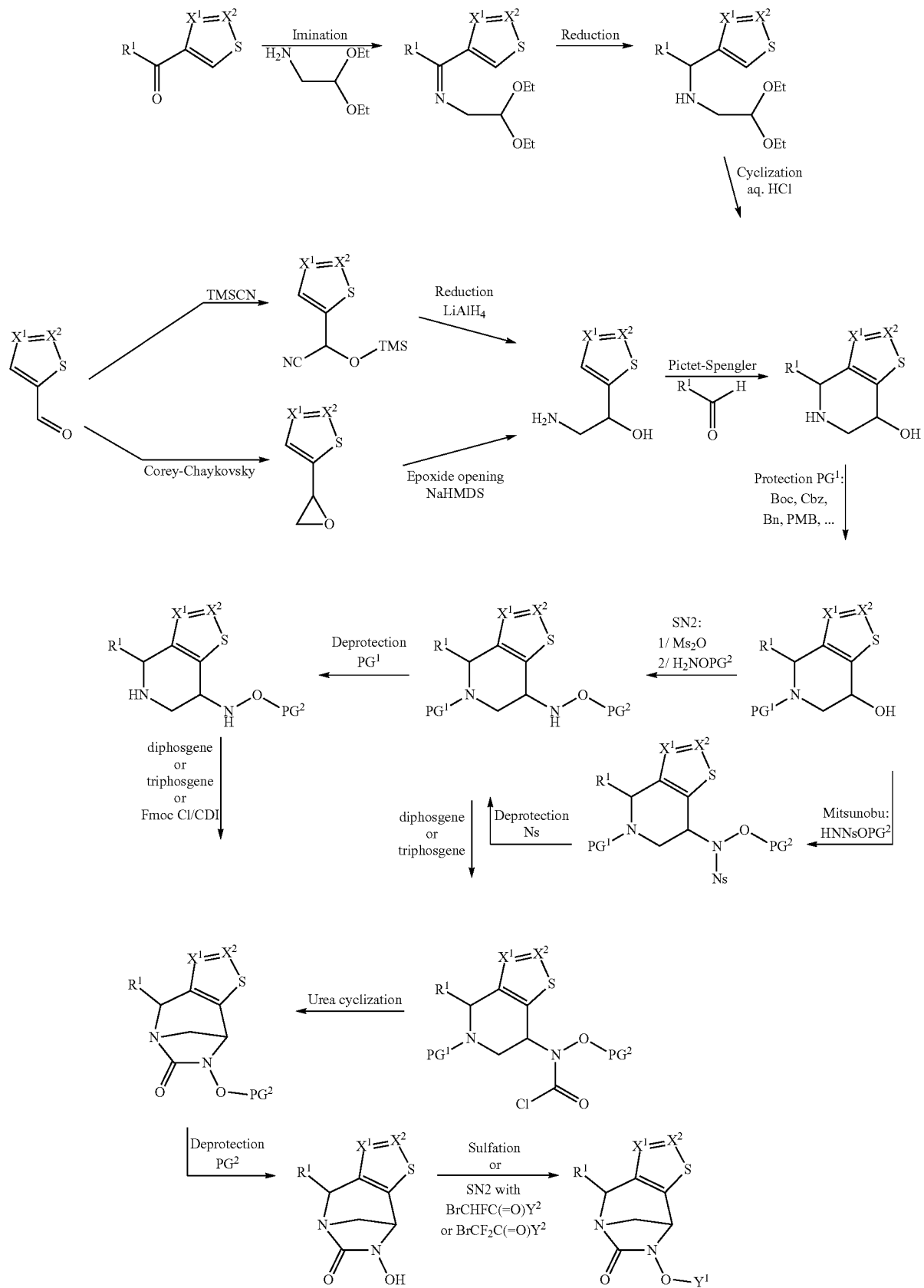

Scheme 2: R¹ introduction, route A
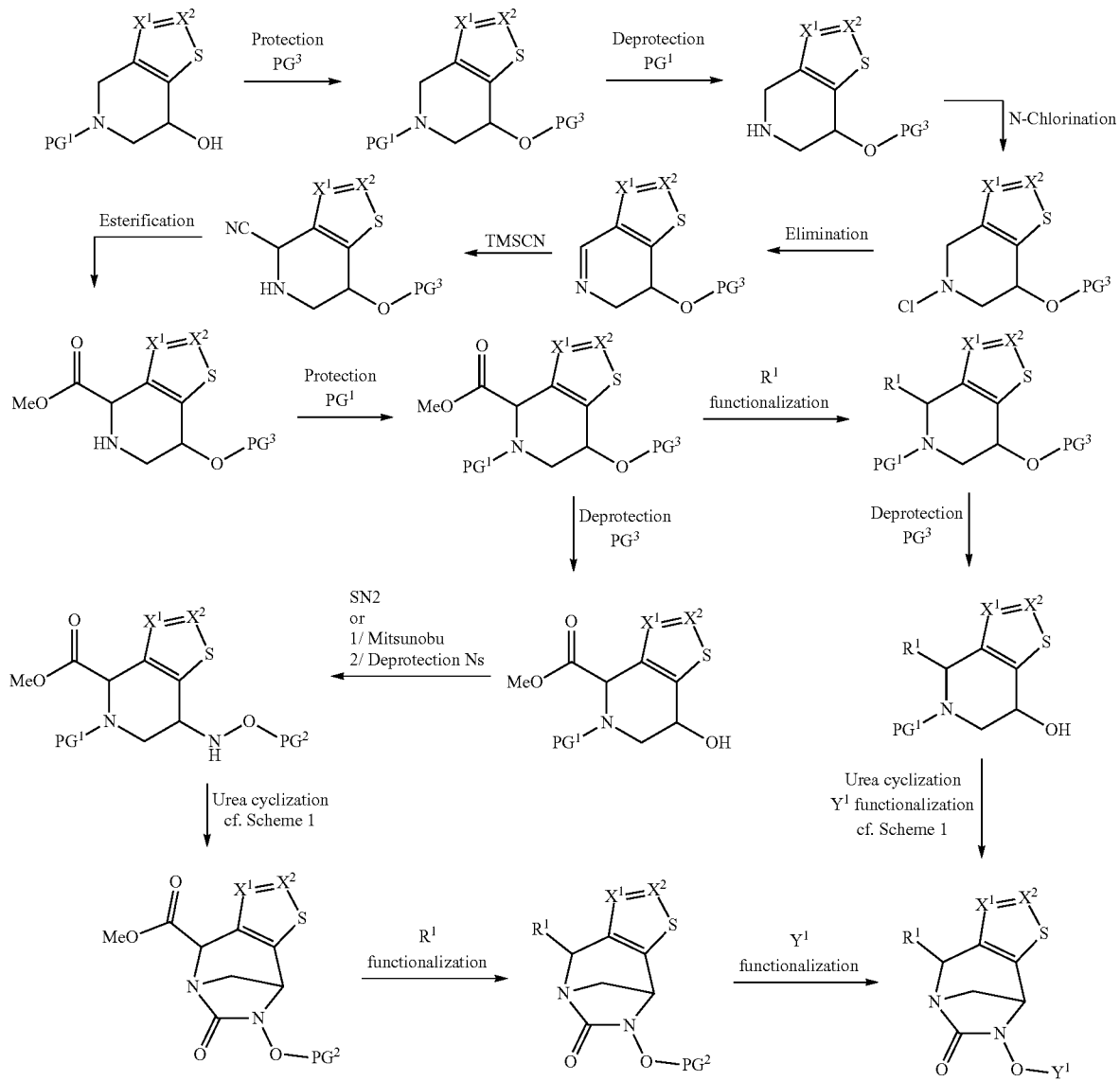
Scheme 3: R¹ introduction, route B
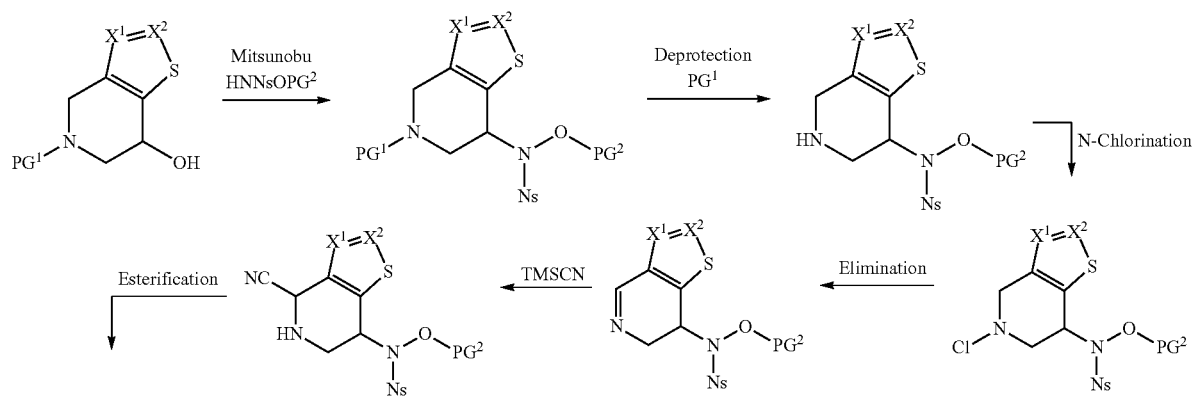

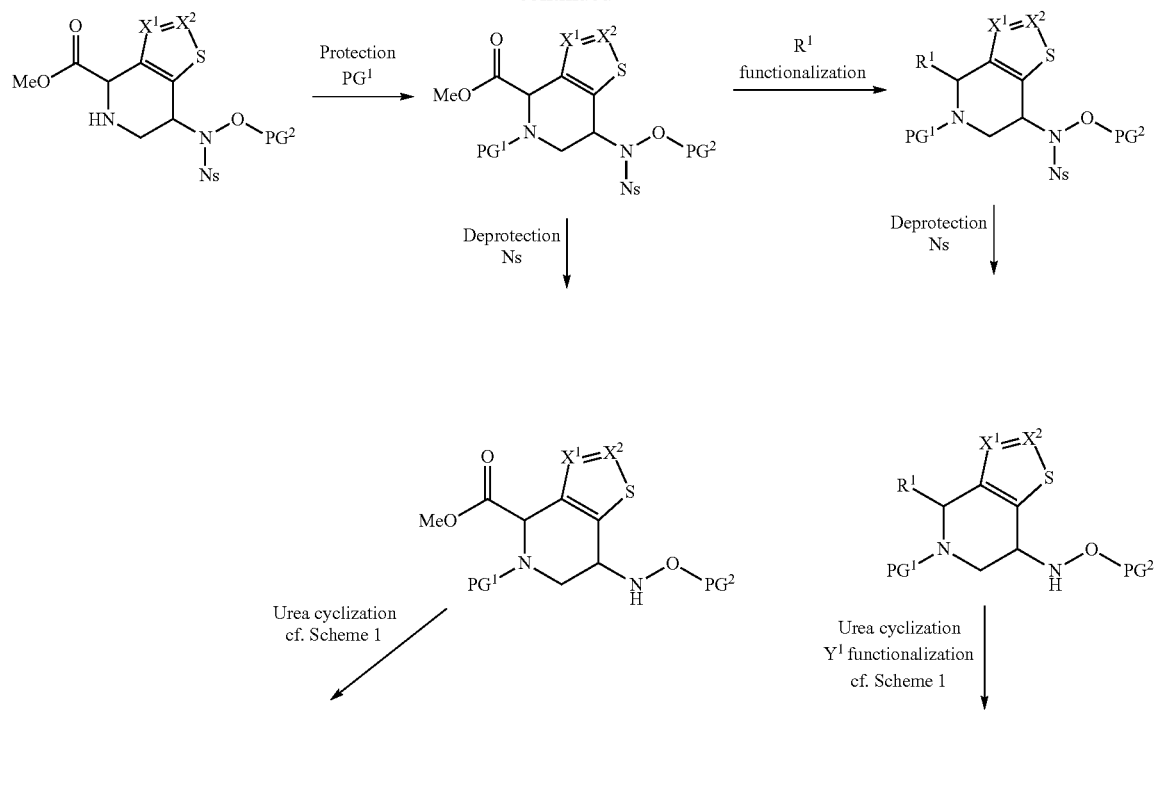
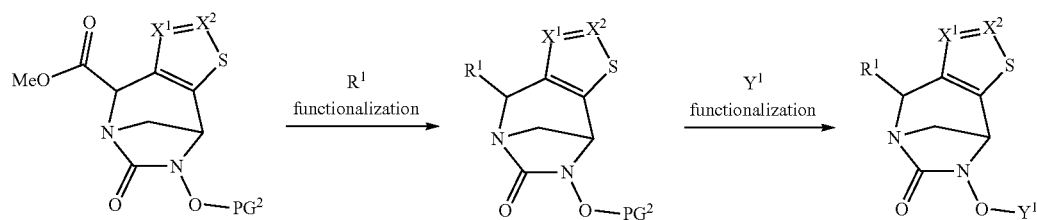
Scheme 4: Thiazole $X^4$ functionalization
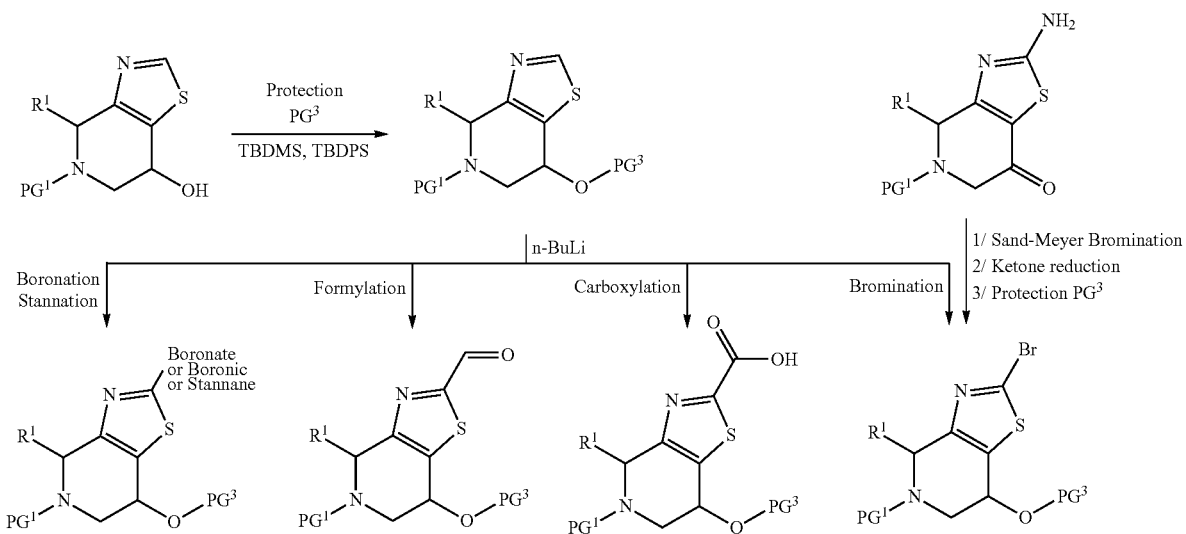

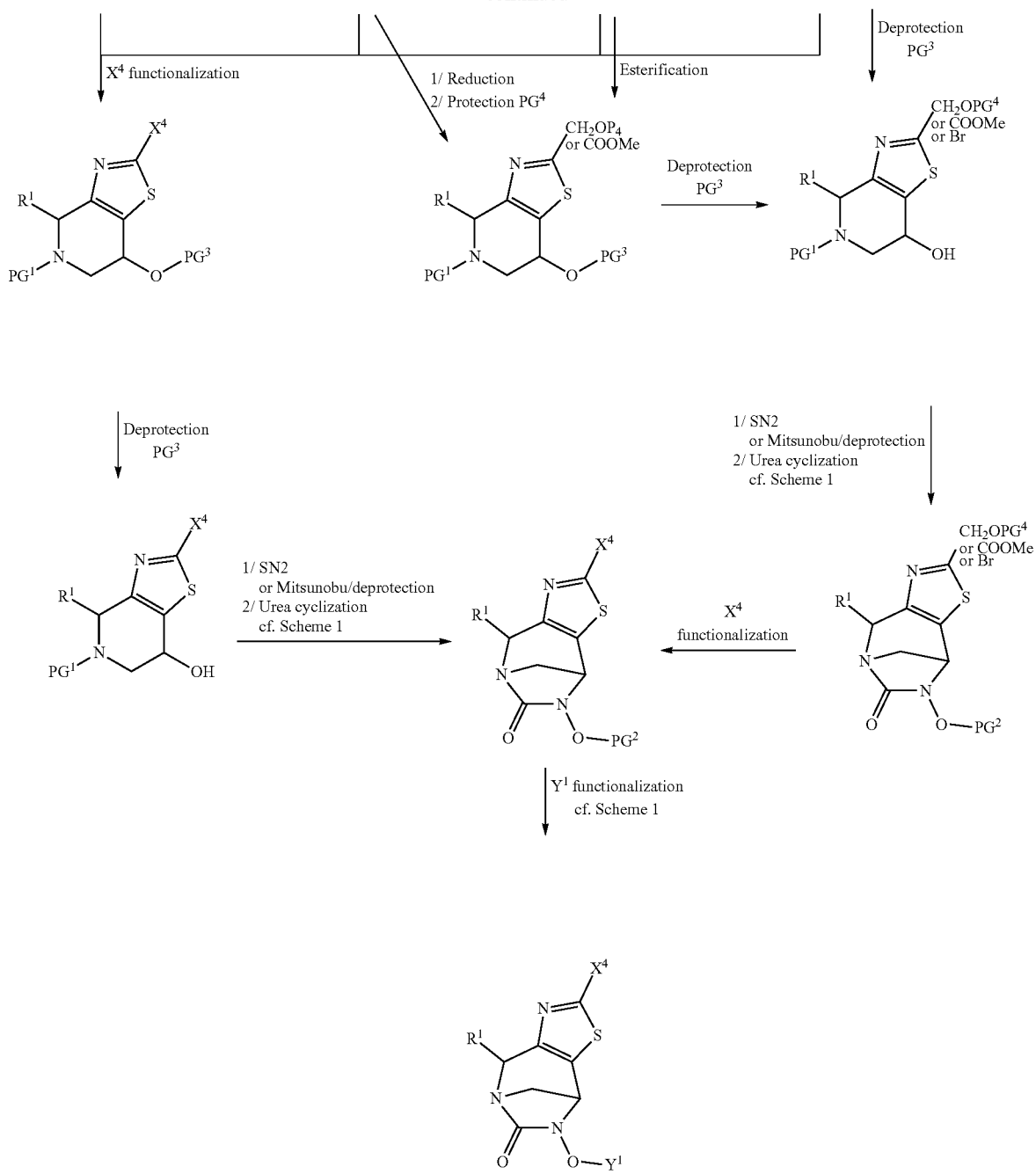
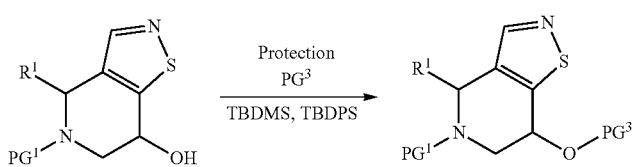
Scheme 5: Isothiazole $X^3$ functionalization

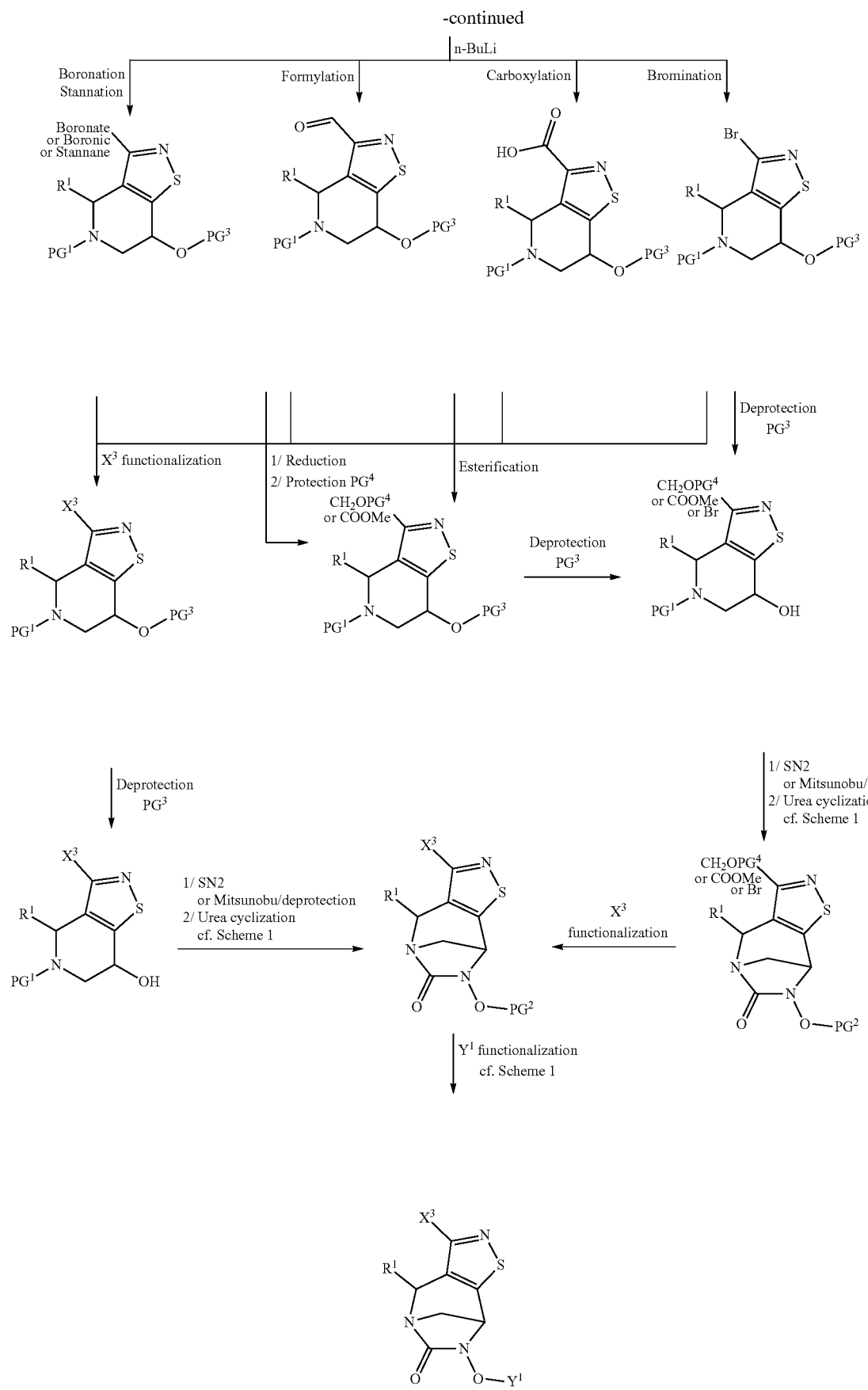

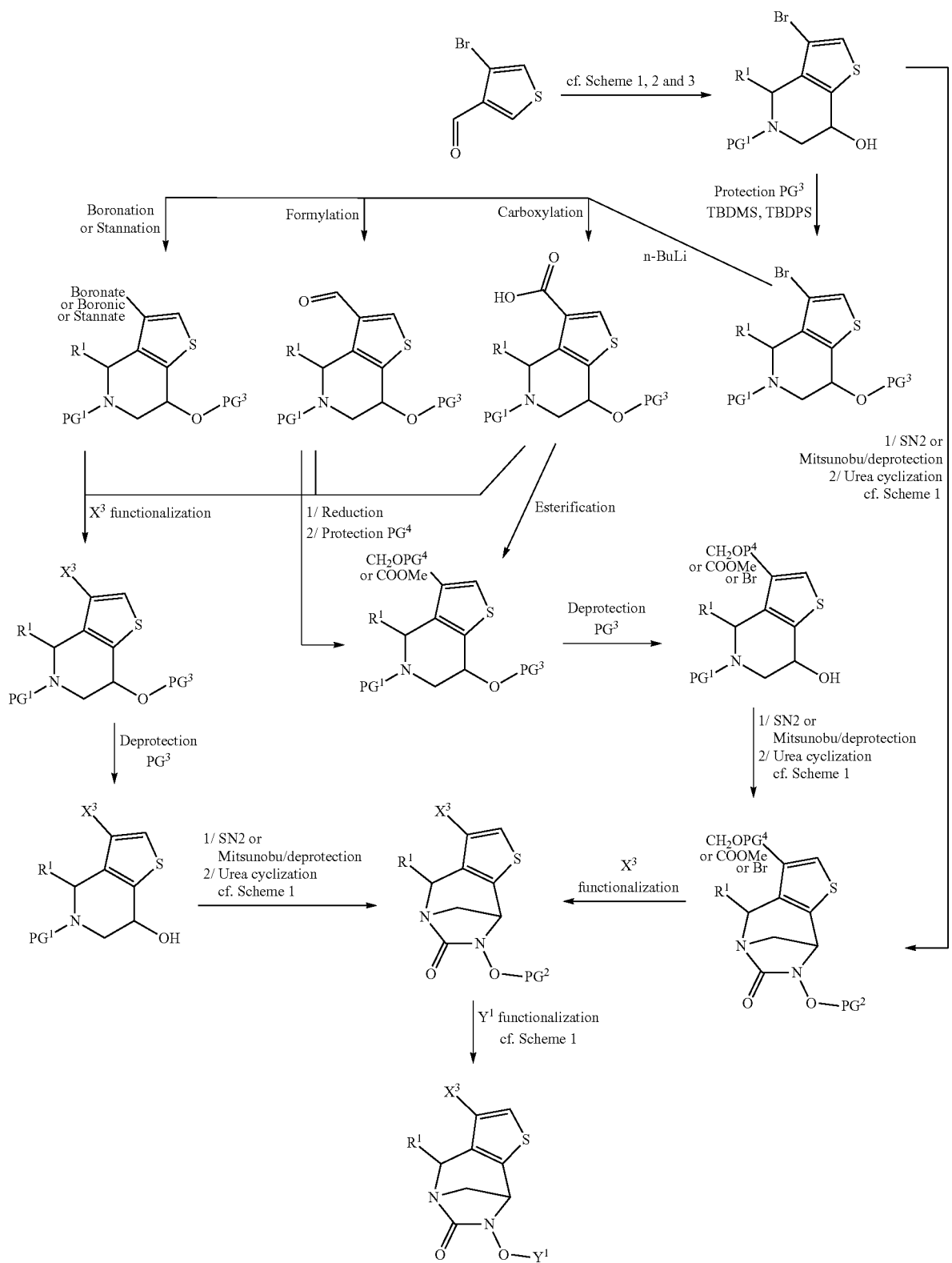
Scheme 6: Thiopene X³ functionalization

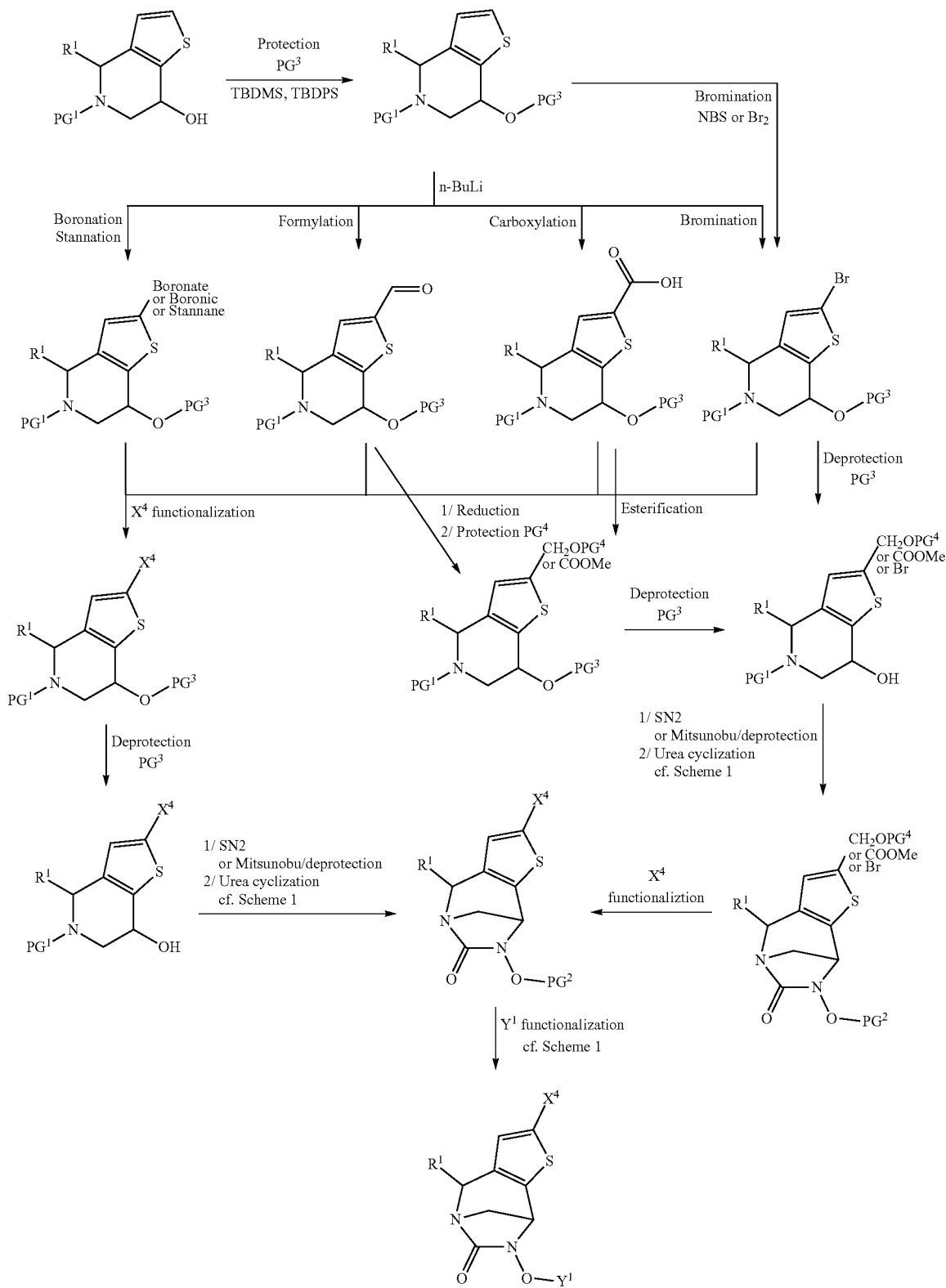
Scheme 7: Thiophene $X^4$ functionalization

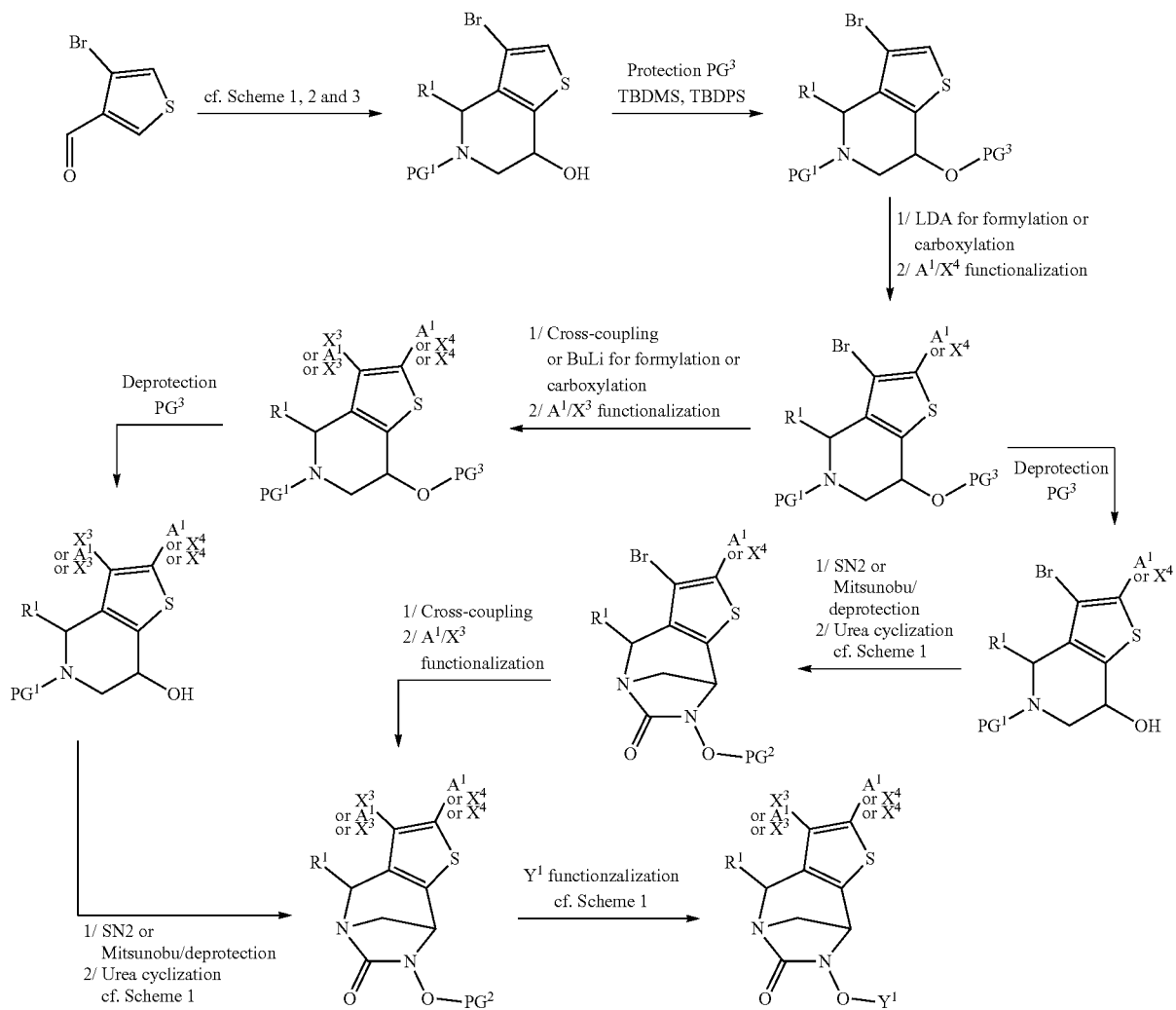

Scheme 9: Thiophene $X^3$, $X^4$ and $A^1$ functionalization

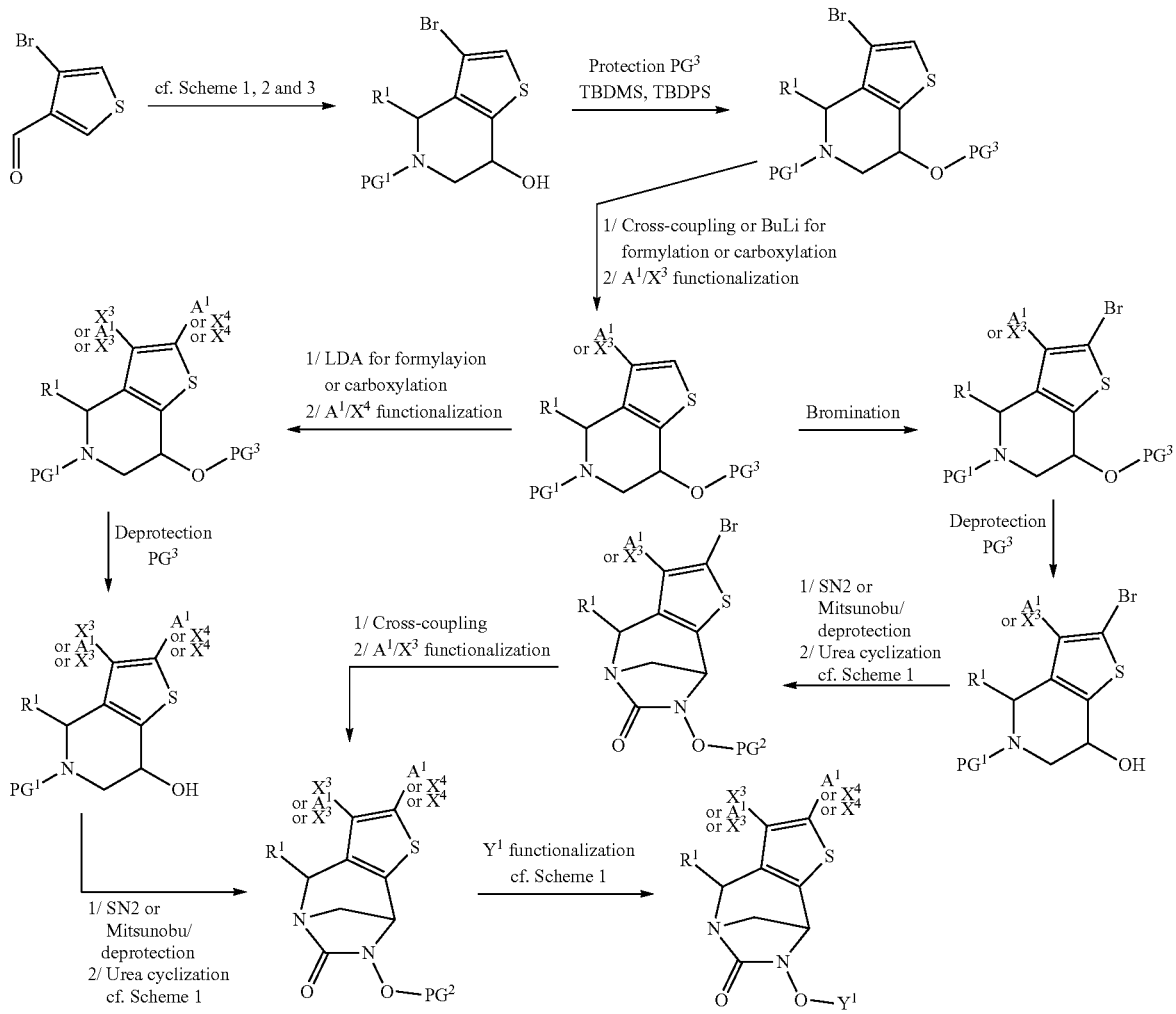

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (I*), (IA), (IA*), (IB), (IB*), (IC), (IC*), (ID), (ID*), (IE), (IE*) in mixture with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a β-lactam chemical group or moiety.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium crosscarmellose, glucose, gelatine, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8th Ed., Pergamon press, 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefiderocol, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072, LYS228 and nocardicin A, alone or in mixture.

The present invention also relates to a composition comprising at least a compound of formulae (I), (I*), (IA), (IA*), (IB), (IB*), (IC), (IC*), (ID), (ID*), (IE), (IE*) according to the invention and ceftazidime.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
a pharmaceutical composition comprising at least a compound of formulae (I) or (I*), according to the invention; and
a pharmaceutical composition comprising ceftazidime.

The present invention also refers to a compound selected within the compounds of formulae (I), (I*), (IA), (IA*), (IB), (IB*), (IC), (IC*), (ID), (ID*), (IE), (IE*) according to the invention for its use as a medicine.

The present invention also refers to a compound selected within the compounds of formulae (I), (I*), (IA), (IA*), (IB), (IB*), (IC), (IC*), (ID), (ID*), (IE), (IE*) according to the invention for its use for the preparation of a medicine.

The present invention also refers to a compound selected within the compounds of formulae (I), (I*), (IA), (IA*), (IB), (IB*), (IC), (IC*), (ID), (ID*), (IE), (IE*) according to the invention for its use as an antibacterial agent.

The present invention also refers to the use of a compound selected within the compounds of formulae (I), (I*), (IA), (IA*), (IB), (IB*), (IC), (IC*), (ID), (ID*), (IE), (IE*) according to the invention or to the use of a pharmaceutical composition according to the invention for the preparation of an antibacterial agent comprising medicine.

The present invention also refers to the use of a compound selected within the compounds of formulae (I), (I*), (IA), (IA*), (IB), (IB*), (IC), (IC*), (ID), (ID*), (IE), (IE*) according to the invention or to the use of a pharmaceutical composition according to the invention for the preparation of a beta-lactamase inhibitor comprising medicine.

The present invention also refers to the use of a compound selected within the compounds of formulae (I), (I*), (IA), (IA*), (IB), (IB*), (IC), (IC*), (ID), (ID*), (IE), (IE*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (I*), (IA), (IA*), (IB), (IB*), (IC), (IC*), (ID), (ID*), (IE), (IE*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (I*), (IA), (IA*), (IB), (IB*), (IC), (IC*), (ID), (ID*), (IE), (IE*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:

to reduce or to eliminate either bacterial infection or one or more symptoms associated with a bacterial infection, or to retard the progression of a bacterial infection or of one or more symptoms associated with a bacterial infection, or to reduce the severity of a bacterial infection or of one or more symptoms associated with a bacterial infection, or to suppress the clinical manifestation of a bacterial infection, or to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus influenza, Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (I*), (IA), (IA*), (IB), (IB*), (IC), (IC*), (ID), (ID*), (IE), (IE*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (I*), (IA), (IA*), (IB), (IB*), (IC), (IC*), (ID), (ID*), (IE), (IE*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (I*), (IA), (IA*), (IB), (IB*), (IC), (IC*), (ID), (ID*), (IE), (IE*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I) or (I*) according to the invention and the further antibacterial agent are administered simultaneously, separately or sequentially.

The present invention also refers to the use of a compound selected within the compounds of formulae (I), (I*), (IA), (IA*), (IB), (IB*), (IC), (IC*), (ID), (ID*), (IE), (IE*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (I*), (IA), (IA*), (IB), (IB*), (IC), (IC*), (ID), (ID*), (IE), (IE*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches. The pharmaceutical composition may be conveniently administered in unit dosage form and may be prepared by any method well-known in the pharmaceutical art, for example, as described in Remington: The Science and Practice of Pharmacy, 20th ed.; Gennaro, A. R., Ed.; Lippincott Williams & Wilkins: Philadelphia, PA, 2000.

Preferred formulations include pharmaceutical compositions wherein a compound according to the present invention is formulated for oral or parenteral administration. For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, crosscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antibacterial activity of compounds according to the invention.

Preparation of the compounds and biological activity:
Abbreviations or symbols used herein include:

| ACHN: | 1,1'-azobis(cyclohexanecarbonitrile) |
|---|---|
| ACN: | acetonitrile |
| AcOH: | acetic acid |
| Bn: | benzyl |
| Boc: | tert-butoxycarbonyl |
| Boc₂O: | tert-butoxycarbonyl anhydride |
| BocON: | [2-(tert-butoxycarbonyloxyimino)-2-phenylacetonitrile] |
| bs: | broad singlet |
| Burgess reagent: | methyl N-(triethylammoniosulfonyl)carbamate |
| CFU: | colony-forming units |
| CLSI: | clinical laboratory standards institute |
| d: | doublet |
| DBU: | 1,8-diazabicyclo[5.4.0]undec-7-ene |
| DCM: | dichloromethane |
| dd: | double doublet |
| ddd: | double double doublet |
| ddt: | double double triplet |
| dq: | double quartet |
| dt: | double triplet |
| DTAD: | di-tert-butylazodicarboxylate |
| DEAD: | diethyl azodicarboxylate |
| Dess-Martin periodinane: | 1,1,1-tris(acetyloxy)-1,1-dihydro-1,2-benziodoxol-3-(1 H)-one |
| DHP | 3,4-dihydro-2H-pyran |
| DIAD: | diisopropyl azodicarboxylate |
| DIPEA: | N,N-diisopropylethylamine |
| DMAP: | 4-dimethylaminopyridine |
| DMF: | N,N-dimethylformamide |
| DMSO: | dimethylsulfoxide |
| EtOAc: | ethyl acetate |
| Et₂O: | diethyl ether |
| h: | hours |
| HATU: | 1-[Bis(dimethylamino)methylene]-1H-1,2,3-triazolo[4,5-b]pyridinium-3-oxid hexafluorophosphate |
| m: | multiplet |
| min: | minutes |
| MeOH: | methanol |
| MeONa: | sodium methoxide |
| MIC: | minimum inhibitory concentration |
| MS: | mass spectrometry |
| MsCl: | methanesulfonyl chloride |
| NBS: | N-bromosuccinimide |
| NMR: | nuclear magnetic resonance spectroscopy |
| Ns: | nosyl, nitrobenzenesulfonyl |
| Pd(Ph₃)₄: | tetrakis(triphenylphosphine)palladium(0) |
| PG: | protective group |
| PhSH: | thiophenol |
| PMe₃: | trimethylphosphine |
| PPh₃: | triphenylphosphine |
| Ppm: | parts per million |
| q: | quartet |
| rt: | room temperature |
| S: | singlet |
| SEM: | [2-(trimethylsilyl)ethoxy]methyl |
| t: | triplet |
| TBAF: | tetra-n-butylammonium fluoride |
| TBDMSCl: | tert-butyldimethylsilyl chloride |
| TBDMSOTf: | trifluoromethanesulfonic acid tert-butyldimethylsilyl ester |
| TBSOTf: | trimethylsilyl trifluoromethanesulfonate |
| tBuOK: | potassium tert-butoxide |

Preparation of the compounds and biological activity:
Abbreviations or symbols used herein include:

| TEA: | triethylamine |
|---|---|
| TFA: | trifluoroacetic acid |
| THF: | tetrahydrofuran |
| THP: | tetrahydropyranyl |
| TLC: | thin layer chromatography |
| TMSI: | Iodotrimethylsilane |

Example 1: synthesis of [2-(2-aminoethylcarbamoyl)-5,8-methano-6-oxo-4,8-dihydrothiazolo[4,5-e][1,3]diazepin-7-yl]sulfonic acid

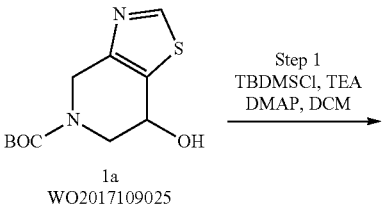

1a
WO2017109025

Step 1
TBDMSCl, TEA
DMAP, DCM

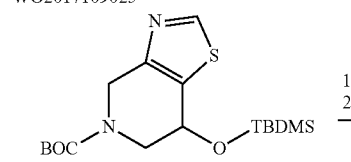

1b

Step 2
1) nBuLi, THF
2) CO₂

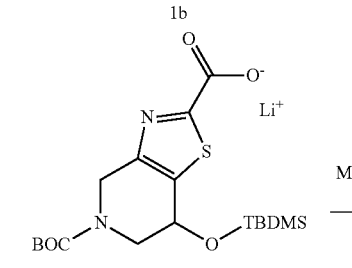

1c

Step 3
Me₂SO₄, K₂CO₃
Acetone

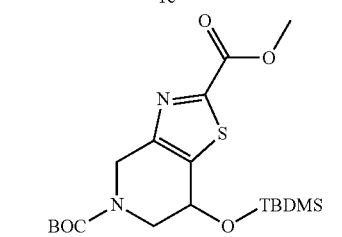

1d

Step 4
TBAF, THF

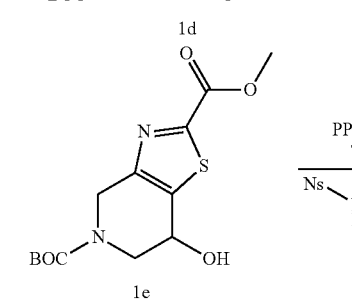

1e

Step 5
PPh₃, DTAD
Toluene

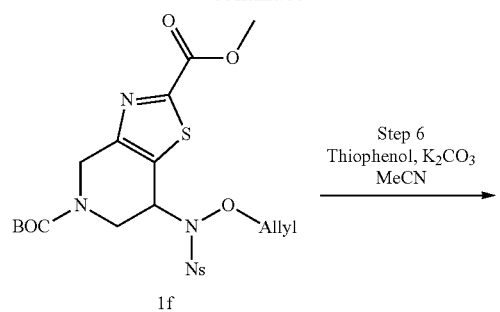

1f

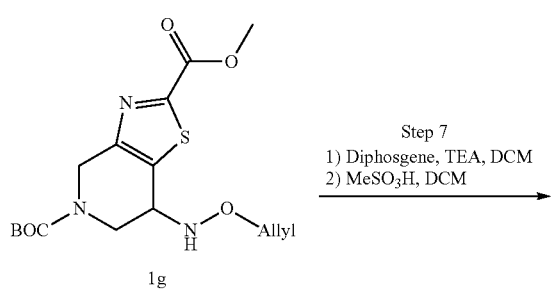

1g

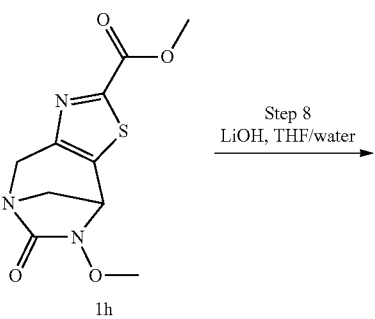

1h

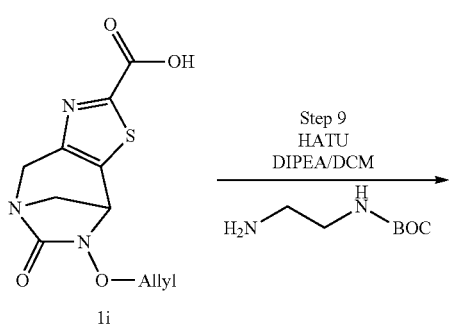

1i

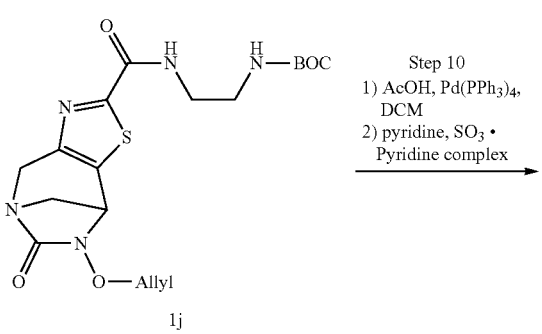

1j

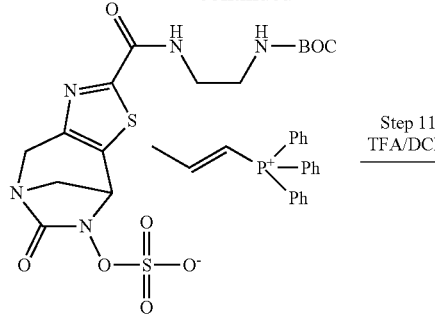

1k

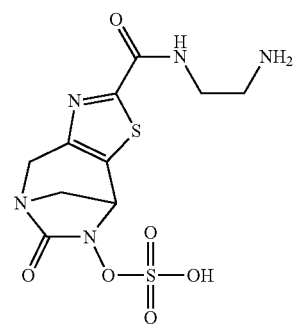

Example 1

Step 1: preparation of intermediate tert-butyl 7-[tert-butyl(dimethyl)silyl]oxy-6,7-dihydro-4H-thiazolo[4,5-c]pyridine-5-carboxylate (1b)

Intermediate (1a) (WO2017109025, 4.86 g, 19 mmol) was dissolved in DCM (38 mL). TEA (5.87 mL, 42 mmol), TBDMSCI (3.15 g, 21 mmol) and DMAP (catalytic amount) were added. The mixture was stirred at rt overnight. As starting material was not totally consumed, TBDMSCI (1.14 g, 7.5 mmol) was added and mixture was stirred at rt for the night. The mixture was diluted with DCM and washed with $H_2O$ and brine. The organic layer was dried over $Na_2SO_4$, filtered and concentrated in vacuo. The crude product was purified by column chromatography on silica gel (DCM/Acetone: 10/0 to 8/2) to give intermediate (1b) (5.45 g, 14.8 mmol, 78%). MS m/z ([M+H]$^+$) 371. $^1$H NMR (400 MHz, CDCl$_3$): δ (ppm) 0.18 (s, 3H), 0.20 (s, 3H), 0.93 (s, 9H), 1.49 (s, 9H), 3.05-3.35 (m, 1H), 4.00-4.35 (m, 1H), 4.45 (d, J=16.8 Hz, 1H), 4.80-5.05 (m, 2H), 8.70 (s, 1H).

Step 2: preparation of intermediate lithium 5-tert-butoxycarbonyl-7-[tert-butyl(dimethyl)silyl]oxy-6,7-dihydro-4H-thiazolo[4,5-c]pyridine-2-carboxylate (1c)

At −78° C., a solution of nBuLi 1.6M in hexane (16.5 mL, 26 mmol) was added to a solution of Intermediate (1b) (4.9 g, 13 mmol) in THF (100 mL). After 30 min, $CO_2$ gas was bubbled in the mixture for 5 min at −78° C. The mixture was warmed rt for 45 min and then concentrated to give a crude which was used in next step without purification. MS m/z ([M+H]$^+$) 415.

Step 3: preparation of intermediate O5-tert-butyl O2-methyl 7-[tert-butyl(dimethyl)silyl]oxy-6,7-dihydro-4H-thiazolo[4,5-c]pyridine-2,5-dicarboxylate (1d)

At rt, a solution of intermediate (1c) (13 mmol), $K_2CO_3$ (2.76 g, 20 mmol) and $Me_2SO_4$ (1.88 mL, 20 mmol) in acetone (85 mL) was stirred for 18 h. As the conversion was not complete, Me$_2$SO$_4$ (1.88 mL, 20 mmol) was added and mixture was stirred at rt for 18 h more. The mixture was quenched by addition of TEA (5.8 mL, 42 mmol) and then stirred at rt for 30 min The mixture was diluted with AcOEt and washed with H$_2$O and brine. The organic layer was dried over Na$_2$SO$_4$, filtered and concentrated in vacuo. The crude product was purified by chromatography on silica gel (DCM/Acetone: 10/0 to 8/2) to give intermediate (1d) (3.75 g, 8.7 mmol, 68% on 2 steps). MS m/z ([M+H]$^+$) 429. $^1$H NMR (400 MHz, CDCl$_3$): δ (ppm) 0.19 (s, 3H), 0.22 (s, 3H), 0.94 (s, 9H), 1.49 (s, 9H), 3.00-3.20 (m, 1H), 4.00 (s, 3H), 4.11-4.41 (m, 1H), 4.40 (dd, J=1.8, 17.1 Hz, 1H), 4.85-5.05 (m, 2H).

Step 4: preparation of intermediate O5-tert-butyl O2-methyl 7-hydroxy-6,7-dihydro-4H-thiazolo[4,5-c]pyridine-2,5-dicarboxylate (1e)

At rt, a solution of TBAF 1M in THF (8.7 mL, 8.7 mmol) was added to a solution of intermediate (1d) (3.75 g, 8.7 mmol) in THF (44 mL). After 30 min, the mixture was diluted with AcOEt and washed with H$_2$O and brine. The organic layer was dried over Na$_2$SO$_4$, filtered and concentrated in vacuo. The crude product was purified by chromatography on silica gel (DCM/Acetone: 10/0 to 5/5) to give intermediate (1e) (2.2 g, 7.0 mmol, 80%). MS m/z ([M+H]$^+$) 315. $^1$H NMR (400 MHz, CDCl$_3$): δ (ppm) 1.48 (s, 9H), 3.74-3.90 (m, 2H), 4.01 (s, 3H), 4.59 (dd, J=1.3, 17.2 Hz, 1H), 4.78-4.88 (m, 1H), 4.96-5.05 (m, 1H).

Step 5: preparation of intermediate O5-tert-butyl O2-methyl 7-[allyloxy-(2-nitrophenyl)sulfonyl-amino]-6,7-dihydro-4H-thiazolo[4,5-c]pyridine-2,5-dicarboxylate (1f)

At 0° C., DTAD (2.09 g, 9.1 mmol) was added portion wise to a solution of intermediate (1e) (2.2 g, 7.0 mmol), N-allyloxy-2-nitro-benzenesulfonamide (2.35 g, 9.1 mmol) and PPh$_3$ (2.38 g, 9.1 mmol) in toluene (70 mL). The mixture was stirred at rt for 2 h 30 and then concentrated. The residue was roughly purified by flash chromatography on silica gel (DCM/Acetone: 10/0 to 7/3) to give intermediate (1f) which was used in next step without further purification. MS m/z ([M+H]$^+$) 555.

Step 6: preparation of intermediate O5-tert-butyl O2-methyl 7-(allyloxyamino)-6,7-dihydro-4H-thiazolo[4,5-c]pyridine-2,5-dicarboxylate (1g)

At 0° C., K$_2$CO$_3$ (7.25 g, 52.5 mmol) and thiophenol (3.59 mL, 35.0 mmol) were added to a solution of intermediate (1f) (7.0 mmol) in ACN (70 mL). After 3 h 30 at rt, the mixture was filtered on celite which was washed with ACN and DCM. The filtrate was concentrated and the residue was purified by flash chromatography on silica gel (DCM/Acetone: 10/0 to 7/3) to provide intermediate (1g) (1.62 g, 4.4 mmol, 62% on 2 steps). MS m/z ([M+H]$^+$) 370. $^1$H NMR (400 MHz, CDCl$_3$): δ (ppm) 1.48 (s, 9H), 3.57-3.79 (m, 1H), 4.00 (s, 3H), 4.00-4.05 (m, 1H), 4.31 (d, J=6.0 Hz, 2H), 4.39-4.45 (m, 1H), 4.51-4.64 (m, 1H), 4.73-4.92 (m, 1H), 5.24 (dd, J=1.5, 10.5 Hz, 1H), 5.33 (dd, J=1.5 17.3 Hz, 1H), 5.93 (ddt, J=5.9, 10.3, 17.3 Hz, 1H).

Step 7: preparation of intermediate methyl 7-allyloxy-5,8-methano-6-oxo-4,8-dihydrothiazolo[4,5-e][1,3]diazepine-2-carboxylate (1h)

At 0° C., diphosgene (0.37 mL, 3.0 mmol) was added to a solution of intermediate (1g) (1.62 g, 4.4 mmol) and TEA (0.92 mL, 6.6 mmol) in DCM (44 mL). The mixture was stirred at 0° C. for 45 min then a solution of MeSO$_3$H (4.27 mL, 65.8 mmol) in DCM (22 mL) was added. After 1 h at 0° C., TEA (12.23 mL, 87.8 mmol) was added and mixture was stirred at rt for 10 min. After partial concentration under azote, the mixture was diluted with DCM and washed with H$_2$O and brine. The organic layer was dried over Na$_2$SO$_4$, filtered and concentrated in vacuo. The crude product was purified by column chromatography on silica gel (DCM/Acetone: 10/0 to 8/2) to give intermediate (1h) (777 mg, 2.6 mmol, 60%). MS m/z ([M+H]$^+$) 296. $^1$H NMR (400 MHz, CDCl$_3$): δ (ppm) 3.26 (d, J=11.3 Hz, 1H), 3.78 (dd, J=2.9, 11.3 Hz, 1H), 4.00 (s, 3H), 4.37-4.53 (m, 3H), 4.67 (d, J=9.4 Hz, 1H), 4.69 (d, J=5.0 Hz, 1H), 5.29-5.40 (m, 2H), 6.00 (dddd, J=6.0, 6.7, 10.3, 17.1 Hz, 1H).

Step 8: preparation of intermediate 7-allyloxy-5,8-methano-6-oxo-4,8-dihydrothiazolo[4,5-e][1,3]diazepine-2-carboxylic acid (1i)

At 0° C., LiOH 1N (2.6 mL, 2.6 mmol) was added to a solution of intermediate (1h) (775 mg, 2.6 mmol) in a mixture of THF (26 mL) and water (13 mL). The mixture was stirred at 0° C. After 40 min, starting material remained and supplementary LiOH 1N (0.26 mL, 0.26 mmol) was added. The mixture was stirred at 0° C. for 15 min more until complete consumption of intermediate (1h). At 0° C., the mixture was quenched by addition of HCl 1N (2.88 mL, 2.88 mmol), diluted with AcOEt and washed with H$_2$O and brine. The organic layer was dried over Na$_2$SO$_4$, filtered and concentrated in vacuo to give intermediate (1i) (639 mg, 2.27 mmol, 87%) which was used in next step without further purification. MS m/z ([M+H]$^+$) 282.

Step 9: preparation of intermediate tert-butyl N-[2-[(7-allyloxy-5,8-methano-6-oxo-4,8-dihydrothiazolo[4,5-e][1,3]diazepine-2-carbonyl)amino]ethyl]carbamate (1j)

DIPEA (0.23 mL, 1.33 mmol) and HATU (243 mg, 0.64 mmol) were added to a solution of intermediate (1i) (150 mg, 0.53 mmol) in DCM (5 mL). After 10 min, tert-butyl N-(2-aminoethyl)carbamate (128 mg, 0.80 mmol) was added and mixture was stirred at rt for 18 h. The mixture was diluted with DCM and washed with H$_2$O and brine. The organic layer was dried over Na$_2$SO$_4$, filtered and concentrated in vacuo. The crude product was purified twice by column chromatography on silica gel (DCM/Acetone: 10/0 to 7/3) to give intermediate (1j) (52 mg, 0.123 mmol). MS m/z ([M−H]$^-$) 422.

Step 10: preparation of intermediate triphenyl-propenylphosphonium [2-[2-(tert-butoxycarbonylamino)ethylcarbamoyl]-5,8-methano-6-oxo-4,8-dihydrothiazolo[4,5-e][1,3]diazepin-7-yl] sulfate (1k)

AcOH (14 μL, 0.24 mmol) and Pd(PPh$_3$)$_4$ (71 mg, 0.06 mmol) were successively added to a solution of intermediate (1j) (52 mg, 0.12 mmol) in anhydrous DCM (1.2 mL). The mixture was stirred at rt for 2 h. Pyridine (1.2 mL) and sulfur trioxide pyridine complex (97 mg, 0.61 mmol) were then added and the mixture was stirred at rt for the night. The heterogeneous mixture was diluted with DCM and solids were filtered off. The filtrate was concentrated and the crude was purified by flash chromatography on silica gel (DCM/ acetone 10/0 to 0/10) to provide intermediate (1k) (22 mg, 0.028 mmol, 24%). MS m/z ([M−H]⁻) 462.

Step 11: preparation of [2-(2-aminoethylcarbamoyl)-5,8-methano-6-oxo-4,8-dihydrothiazolo[4,5-e][1,3]diazepin-7-yl]sulfonic acid, Example 1

At 0° C., TFA (0.1 mL) was added to a solution of intermediate (1k) (22 mg, 0.028 mmol) in DCM (0.13 mL). The mixture was stirred at 0° C. for 30 min. At 0° C., Et₂O was added to give a precipitate and supernatant was eliminated (operation done 3 times). The residue was triturated twice with ACN and supernatant was eliminated each time. The precipitate was filtered on PTFE membrane and dried under vacuum. The crude was purified by column chromatography on C18 (Water/ACN 99/1 to 70/30). The fractions containing the desired compound were combined, partially concentrated under flux of nitrogen to remove ACN, frozen and lyophilized to provide Example 1 (6 mg, 0.016 mmol, 60%). MS m/z ([M+H]⁺) 364. ¹H NMR (400 MHz, D₂O): δ (ppm) 3.30 (t, J=5.7 Hz, 2H), 3.61 (d, J=11.7 Hz, 1H), 3.68-3.84 (m, 2H), 3.97 (dd, J=3.0, 11.7 Hz, 1H), 4.58 (d, J=16.8 Hz, 1H), 4.65 (d, J=16.8 Hz, 1H), 5.30 (d, J=2.8 Hz, 1H). ¹⁹F NMR (377 MHz, D₂O): no fluorine.

Example 2: synthesis of [2-(quanidinomethyl)-5,8-methano-6-oxo-4,8-dihydrothiazolo[4,5-e][1,3]diazepin-7-yl]sulfonic acid

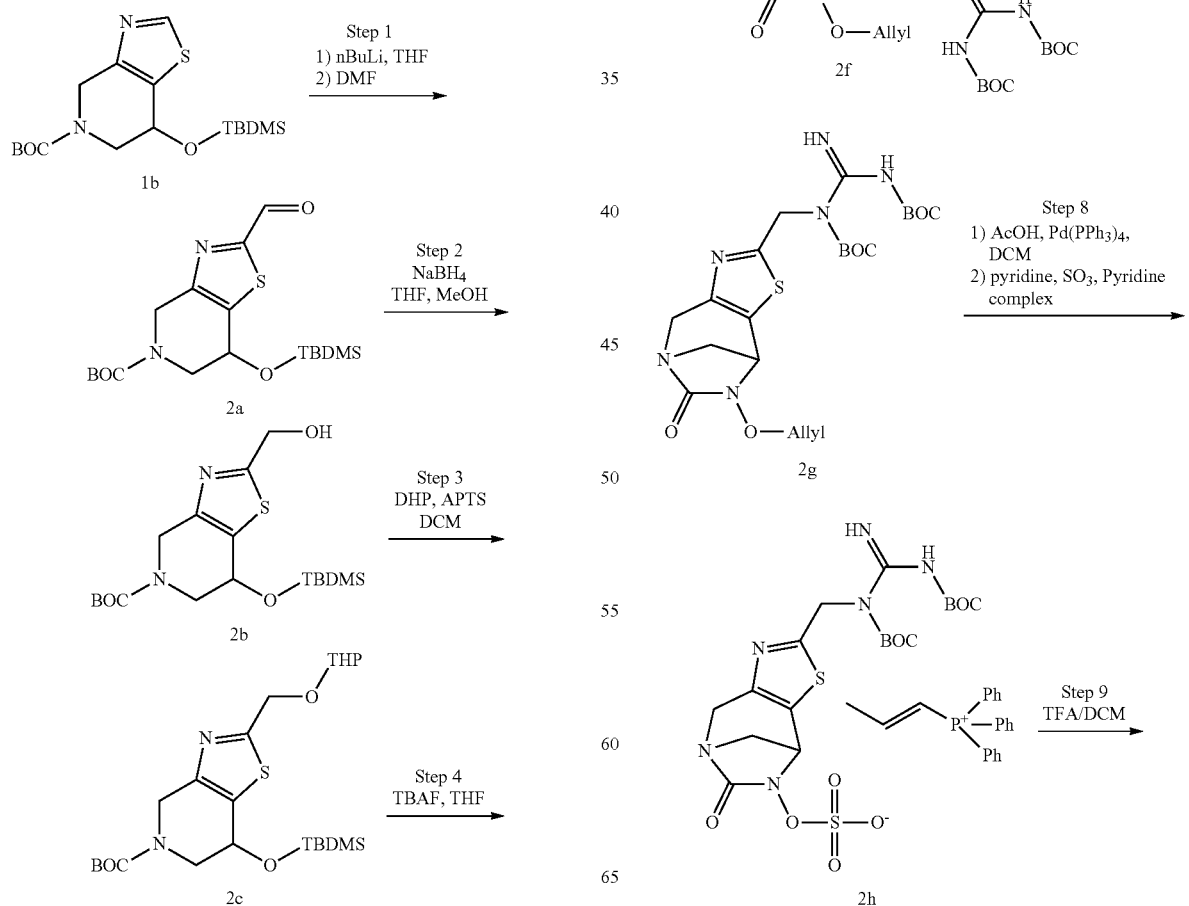

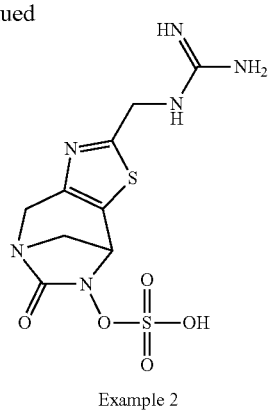

Example 2

Step 1: preparation of intermediate tert-butyl 7-[tert-butyl(dimethyl)silyl]oxy-2-formyl-6,7-dihydro-4H-thiazolo[4,5-c]pyridine-5-carboxylate (2a)

At −78° C. a solution of nBuLi 1.6M in hexanes (2.16 mL, 5.4 mmol) was added to a solution of intermediate (1b) (2.0 g, 5.4 mmol) in THF (27 mL). The mixture was stirred at −78° C. for 30 min before a solution of DMF (0.42 mL, 5.4 mmol) in THF (3 mL) was added. The mixture was stirred for 10 min at −78° C. The temperature was allowed to rise up at 0° C. for 1h. The reaction was quenched by addition of NH$_4$Cl solution, diluted with AcOEt, washed with H$_2$O and brine. The organic layer was dried over Na$_2$SO$_4$, filtered and concentrated in vacuo. The residue was used in next step without purification. MS m/z ([M+H]$^+$) 399. $^1$H NMR (400 MHz, CDCl$_3$): δ (ppm) 0.20 (s, 3H), 0.22 (s, 3H), 0.94 (s, 9H), 1.50 (s, 9H), 2.95-3.20 (m, 1H), 4.15-4.43 (m, 1H), 4.41 (d, J=16.8 Hz, 1H), 4.87-5.08 (m, 2H), 9.91 (s, 1H).

Step 2: preparation of intermediate tert-butyl 7-[tert-butyl(dimethyl)silyl]oxy-2-(hydroxymethyl)-6,7-dihydro-4H-thiazolo[4,5-c]pyridine-5-carboxylate (2b)

At 0° C., NaBH$_4$ (225 mg, 5.94 mmol) was added to a solution of intermediate (2a) (5.4 mmol) in a mixture of THF (5 mL)/MeOH (15 mL). The mixture was stirred at rt for 30 min. Reaction was quenched by addition of acetone and water. After partial concentration, the residue was diluted with AcOEt and washed with H$_2$O and brine. The organic layer was dried over Na$_2$SO$_4$, filtered and concentrated in vacuo. The crude product was purified by column chromatography on silica gel (DCM/Acetone: 10/0 to 5/5) to give intermediate (2b) (1.38 g, 3.5 mmol, 64% on 2 steps). MS m/z ([M+H]$^+$) 401. $^1$H NMR (400 MHz, CDCl$_3$): δ (ppm) 0.18 (s, 3H), 0.20 (s, 3H), 0.93 (s, 9H), 1.48 (s, 9H), 2.74 (bs, 1H), 3.04-3.30 (m, 1H), 3.99-4.32 (m, 1H), 4.39 (dd, J=1.7, 17.0 Hz, 1H), 4.73-4.96 (m, 2H), 4.93 (s, 2H).

Step 3: preparation of intermediate tert-butyl 7-[tert-butyl(dimethyl)silyl]oxy-2-(tetrahydropyran-2-yloxymethyl)-6,7-dihydro-4H-thiazolo[4,5-c]pyridine-5-carboxylate (2c)

DHP (0.17 mL, 1.87 mmol) and APTS (catalytic amount) were added to a solution of intermediate (2b) (500 mg, 1.25 mmol) in DCM (12 mL). The mixture was stirred at rt for 3h, diluted with DCM and washed with H$_2$O and brine. The organic layer was dried over Na$_2$SO$_4$, filtered and concentrated in vacuo. The crude product was purified by chromatography on silica gel (DCM/Acetone: 10/0 to 7/3) to give intermediate (2c) (570 mg, 1.18 mmol, 95%). MS m/z ([M+H]$^+$) 485. $^1$H NMR (400 MHz, CDCl$_3$): δ (ppm) 0.18 (s, 3H), 0.20 (s, 3H), 0.93 (s, 9H), 1.48 (s, 9H), 1.52-1.92 (m, 6H), 3.08-3.32 (m, 1H), 3.53-3.60 (m, 1H), 3.89 (ddt, J=2.8, 8.8, 11.4 Hz, 1H), 3.97-430 (m, 1H), 4.39 (d, J=16.8 Hz, 1H), 4.76 (d, J=13.7 Hz, 1H), 4.77-4.81 (m, 2H), 4.86-4.98 (m, 1H), 4.94 (d, J=13.7 Hz, 1H).

Step 4: preparation of intermediate tert-butyl 7-hydroxy-2-(tetrahydropyran-2-yloxymethyl)-6,7-dihydro-4H-thiazolo[4,5-c]pyridine-5-carboxylate (2d)

At 0° C., TBAF 1M in THF (1.18 mL, 1.18 mmol) was added to a solution of intermediate (2c) (570 mg, 1.18 mmol) in THF (6 mL). The mixture was stirred at 0° C. for 1 h, diluted with AcOEt and washed with H$_2$O and brine. The organic layer was dried over Na$_2$SO$_4$, filtered and concentrated in vacuo. The crude product was purified by column chromatography on silica gel (DCM/Acetone: 10/0 to 4/6) to give intermediate (2d) (413 mg, 1.12 mmol, 95%). MS m/z ([M+H]$^+$) 371. $^1$H NMR (400 MHz, CDCl$_3$): δ (ppm) 1.49 (s, 9H), 1.51-1.90 (m, 6H), 3.57 (ddt, J=2.9, 5.6, 9.8 Hz, 1H), 3.60-3.70 (m, 1H), 3.83-3.92 (m, 1H), 3.98 (dd, J=4.2, 13.7 Hz, 1H), 4.42 (d, J=17.0 Hz, 1H), 4.74-4.86 (m, 3H), 4.89-4.96 (m, 1H), 4.95 (d, J=14.0 Hz, 1H).

Step 5: preparation of intermediate tert-butyl 7-(allyloxyamino)-2-(tetrahydropyran-2-yloxymethyl)-6,7-dihydro-4H-thiazolo[4,5-c]pyridine-5-carboxylate (2e)

At −78° C., a solution of Ms$_2$O (580 mg, 3.33 mmol) in DCM (2.5 mL) was added to a solution of TEA (0.61 mL, 4.44 mmol) and intermediate (2d) (410 mg, 1.11 mmol) in DCM (11 mL). After 45 min at −78° C., a solution of NH$_2$OAll (566 mg, 7.76 mmol) in DCM (2.5 mL) was added. The mixture was stirred 15 min at −78° C. Temperature was allowed to rise up at rt for 1h. The mixture was diluted with DCM and washed with H$_2$O and brine. The organic layer was dried over Na$_2$SO$_4$, filtered and concentrated in vacuo. The crude product was purified by column chromatography on silica gel (DCM/AcOEt: 10/0 to 2/8) to give intermediate (2e) (375 mg, 0.88 mmol, 80%). MS m/z ([M+H]$^+$) 426. $^1$H NMR (400 MHz, CDCl$_3$): δ (ppm) 1.49 (s, 9H), 1.51-1.92 (m, 6H), 3.45-3.65 (m, 2H), 3.88 (ddd, J=3.1, 8.9, 11.4 Hz, 1H), 4.10-4.53 (m, 5H), 4.73-4.86 (m, 3H), 4.98 (dd, J=6.2, 14.6 Hz, 1H), 5.21-5.26 (m, 1H), 5.29-5.36 (m, 1H), 5.94 (ddt, J=5.9, 10.3, 17.3 Hz, 1H).

Step 6: preparation of intermediate 7-allyloxy-2-(hydroxymethyl)-5,8-methano-4,8-dihydrothiazolo[4,5-e][1,3]diazepin-6-one (2f)

At 0° C., diphosgene (74 µL, 0.61 mmol) was added to a solution of intermediate (2e) (370 mg, 0.87 mmol) and TEA (0.18 mL, 1.3 mmol) in DCM (9 mL). The mixture was stirred at 0° C. for 45 min then a solution of MeSO$_3$H (0.85 mL, 13.05 mmol) in DCM (1 mL) was added. After 1 h at 0° C., TEA (2.4 mL, 17.4 mmol) was added and the mixture was stirred at rt for 1 h. The mixture was diluted with DCM and washed with H$_2$O and brine. The organic layer was dried over Na$_2$SO$_4$, filtered and concentrated in vacuo. The crude product was purified by column chromatography on silica gel (DCM/Acetone: 10/0 to 2/8) to give intermediate (2f) (163 mg, 0.61 mmol, 71%). MS m/z ([M+H]$^+$) 268. $^1$H NMR (400 MHz, CDCl$_3$): δ (ppm) 3.17 (d, J=11.0 Hz, 1H), 3.66 (dd, J=2.9, 11.1 Hz, 1H), 4.29 (d, J=16.8 Hz, 1H), 4.30-4.43 (m, 2H), 4.49 (d, J=16.8 Hz, 1H), 4.55 (d, J=2.3 Hz, 1H), 4.78 (s, 2H), 5.22-5.27 (m, 1H), 5.30 (dq, J=1.4, 17.2 Hz, 1H), 5.88-5.99 (m, 1H).

Step 7: preparation of intermediate tert-butyl N-[(7-allyloxy-5,8-methano-6-oxo-4,8-dihydrothiazolo[4,5-e][1,3]diazepin-2-yl)methyl]-N-(N-tert-butoxycarbonylcarbamimidoyl)carbamate (2g)

Under argon atmosphere and at 0° C., DTAD (48 mg, 0.21 mmol) was added portionwise to a solution of intermediate (2f) (50 mg, 0.17 mmol), tert-butyl N-(N-tert-butoxycarbonylcarbamimidoyl)carbamate (54 mg, 0.21 mmol) and PPh3 (55 mg, 0.21 mmol) in toluene (1.2 mL). The mixture was stirred at rt for 2h and then concentrated. The residue was purified by column chromatography on silica gel (DCM/AcOEt: 10/0 to 4/6) to provide intermediate (2g) (40 mg, 0.08 mmol, 47%). MS m/z ([M+H]$^+$) 509. $^1$H NMR (400 MHz, CDCl$_3$): δ (ppm) 1.39 (s, 9H), 1.49 (s, 9H), 3.21 (d, J=10.9 Hz, 1H), 3.70 (dd, J=2.9, 11.0 Hz, 1H), 4.32 (d, J=16.8 Hz,1H), 4.35-4.48 (m, 2H), 4.52 (d, J=16.8 Hz, 1H), 4.56 (d, J=2.7 Hz, 1H), 5.26-5.38 (m, 3H), 5.49 (d, J=16.0 Hz, 1H), 5.92-6.04 (m, 1H), 9.40-9.43 (m, 2H).

Step 8: preparation of intermediate triphenyl-propenylphosphonium [2-[[tert-butoxycarbonyl-(N-tert-butoxycarbonylcarbamimidoyl)amino]methyl]-5,8-dimethyl-6-oxo-4,8-dihydrothiazolo[4,5-e][1,3]diazepin-7-yl] sulfate (2h)

AcOH (9 μL, 0.16 mmol) and Pd(PPh$_3$)$_4$ (45 mg, 0.04 mmol) were successively added to a solution of intermediate (2g) (40 mg, 0.08 mmol) in anhydrous DCM (0.8 mL). After stirring for 1 h 30 at rt, pyridine (0.8 mL) and sulfur trioxide pyridine complex (62 mg, 0.39 mmol) were added and the mixture was stirred at rt overnight. The heterogeneous mixture was diluted with DCM and the solids were filtered off. The filtrate was concentrated and purified by flash chromatography on silica gel (DCM/acetone 10/0 to 0/10) to provide intermediate (2h) (38 mg, 0.05 mmol, 58%) with traces of POPh$_3$. MS m/z ([M+H]$^+$) 549 and 303.

Step 9: preparation of [2-(quanidinomethyl)-5,8-dimethyl-6-oxo-4,8-dihydrothiazolo[4,5-e][1,3]diazepin-7-yl]sulfonic acid, Example 2

At 0° C., TFA (0.15 mL) was added to a solution of intermediate (2h) (38 mg, 0.05 mmol) in DCM (0.15 mL). The mixture was stirred at 0° C. for 3 h 30. As reaction was not completed, TFA (0.15 mL) was added and mixture was stirred at 0° C. for 1 h 30 more (operation repeated twice). At 0° C., a precipitate was obtained by addition of Et$_2$O and the supernatant was eliminated (operation repeated 3 times). The residue was triturated with ACN and supernatant was eliminated (operation repeated twice). The precipitate was filtered, dried under vacuum and purified by column chromatography on C18 (Water/ACN 99/1 to 50/50). The fractions containing the desired compound were combined, partially concentrated under flux of nitrogen to remove ACN, frozen and lyophilized to provide Example 2 as zwitterion (2.1 mg, 0.006 mmol, 14%). MS m/z ([M−H]$^-$) 347. $^1$H NMR (400 MHz, D$_2$O): δ (ppm) 3.59 (d, J=11.6 Hz, 1H), 3.92 (dd, J=3.0, 11.6 Hz, 1H), 4.50 (d, J=16.8 Hz, 1H), 4.59 (d, J=16.8 Hz, 1H), 4.78 (s, 2H), 5.20 (d, J=2.8 Hz, 1H). $^{19}$F NMR (377 MHz, D$_2$O): no fluorine.

Example 3: synthesis of [2-(2-quanidinoethylcarbamoyl)-5,8-methano-6-oxo-4,8-dihydrothiazolo[4,5-e][1,3]diazepin-7-yl]sulfonic acid

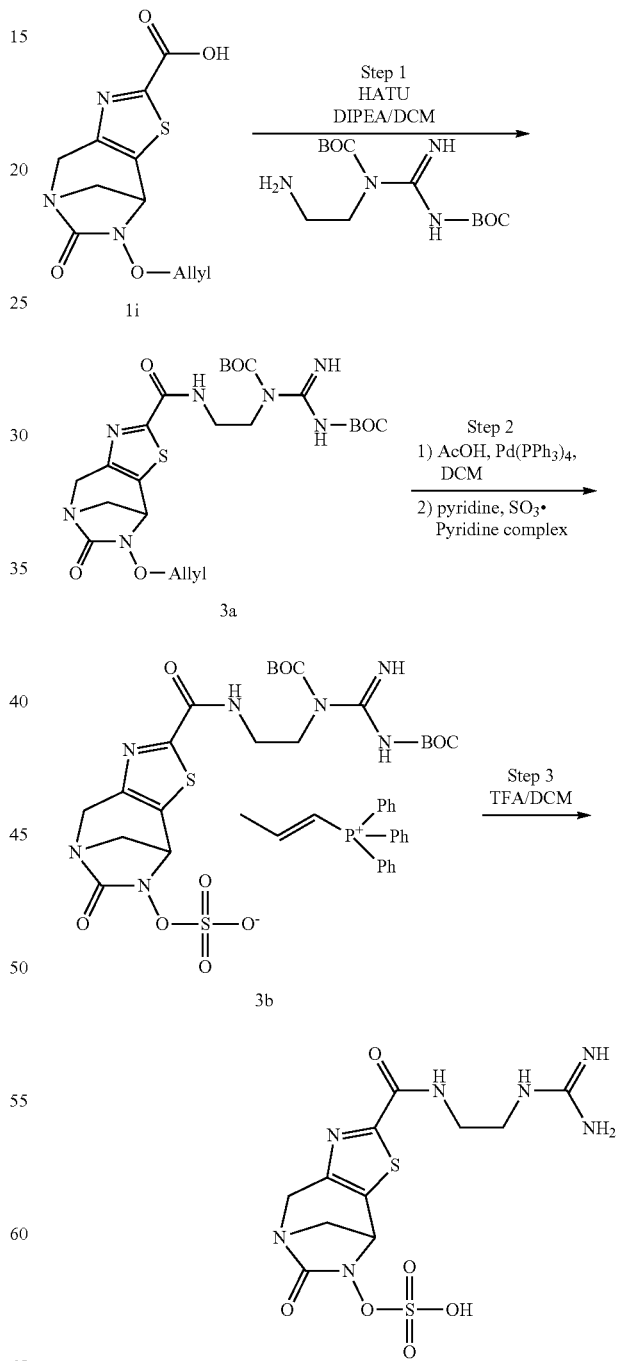

Example 3

Step 1: preparation of intermediate tert-butyl N-[2-[(7-allyloxy-5,8-methano-6-oxo-4,8-dihydrothiazolo[4,5-e][1,3]diazepine-2-carbonyl)amino]ethyl]-N-(N- tert-butoxycarbonylcarbamimidoyl)carbamate (3a)

DIPEA (0.23 mL, 1.33 mmol) and HATU (243 mg, 0.64 mmol) were added to a solution of intermediate (1i) (150 mg, 0.53 mmol) in DCM (3.5 mL). After 10 min, tert-butyl N-[N'-(2-aminoethyl)-N-tert-butoxycarbonyl-carbamimidoyl]carbamate (193 mg, 0.64 mmol) was added and mixture was stirred at rt for 4h. As starting material was not totally consumed, HATU (60 mg, 0.16 mmol) was added and mixture was stirred for 40 min more. The mixture was diluted with DCM and washed with H$_2$O and brine. The organic layer was dried over Na$_2$SO$_4$, filtered and concentrated in vacuo. The crude product was purified twice by column chromatography on silica gel (DCM/AcOEt: 10/0 to 7/3) and by preparative TLC (eluting DCM/AcOEt 9/1) to give intermediate (3a) (105 mg, 0.160 mmol). MS m/z ([M+H]$^+$) 566.

Step 2: preparation of intermediate triphenyl-propenylphosphonium [2-[2-[tert-butoxycarbonyl-(N-tert-butoxycarbonylcarbamimidoyl)amino]ethylcarbamoyl]-5,8-methano-6-oxo-4,8-dihydrothiazolo[4,5-e][1,3]diazepin-7-yl] sulfate (3b)

AcOH (19 µL, 0.32 mmol) and Pd(PPh$_3$)$_4$ (92 mg, 0.06 mmol) were successively added to a solution of intermediate (3a) (105 mg, 0.16 mmol) in anhydrous DCM (1.6 mL). The mixture was stirred at rt for 2 h. Pyridine (1.6 mL) and sulfur trioxide pyridine complex (127 mg, 0.80 mmol) were then added and the mixture was stirred at rt overnight. The heterogeneous mixture was diluted with DCM and solids were filtered off. The filtrate was concentrated and the crude was purified by flash chromatography on silica gel (DCM/acetone 10/0 to 0/10) to provide intermediate (3b) (38 mg, 0.041 mmol, 26%). MS m/z ([M+H]$^+$) 606 and 303.

Step 3: preparation of [2-(2-quanidinoethylcarbamoyl)-5,8-methano-6-oxo-4,8-dihydrothiazolo[4,5-e][1,3]diazepin-7-yl]sulfonic acid, Example 3

At 0° C., TFA (0.4 mL) was added to a solution of intermediate (3b) (38 mg, 0.041 mmol) in DCM (0.4 mL). The mixture was stirred at 0° C. for 7 h and at −20° C. for 18 h. At 0° C., Et$_2$O was added to give a precipitate and supernatant was eliminated (operation repeated 3 times). The residue was triturated twice with ACN and supernatant was eliminated each time. After trituration, the obtained solid was filtered on PTFE membrane and dried under vacuum. The crude was purified by column chromatography on C18 (Water/ACN 99/1 to 80/20). The fractions containing the desired compound were combined, partially concentrated under flux of nitrogen to remove ACN, frozen and lyophilized to provide Example 3 as zwitterion (2 mg, 0.005 mmol, 13%). MS m/z ([M−H]$^-$) 404. $^1$H NMR (400 MHz, D$_2$O): δ (ppm) 3.45-3.51 (m, 2H), 3.54-3.64 (m, 2H), 3.65-3.73 (m, 1H), 3.96 (dd, J=3.0, 11.7 Hz, 1H), 4.58 (d, J=16.9 Hz, 1H), 4.65 (d, J=16.9 Hz, 1H), 5.29 (d, J=2.8 Hz, 1H). $^{19}$F NMR (377 MHz, D$_2$O): no fluorine.

Example 4 (comparative): synthesis of [2-(aminomethyl)-5,8-dimethyl-6-oxo-4,8-dihydrothiazolo[4,5-e][1,3]diazepin-7-yl] hydrogen sulfate

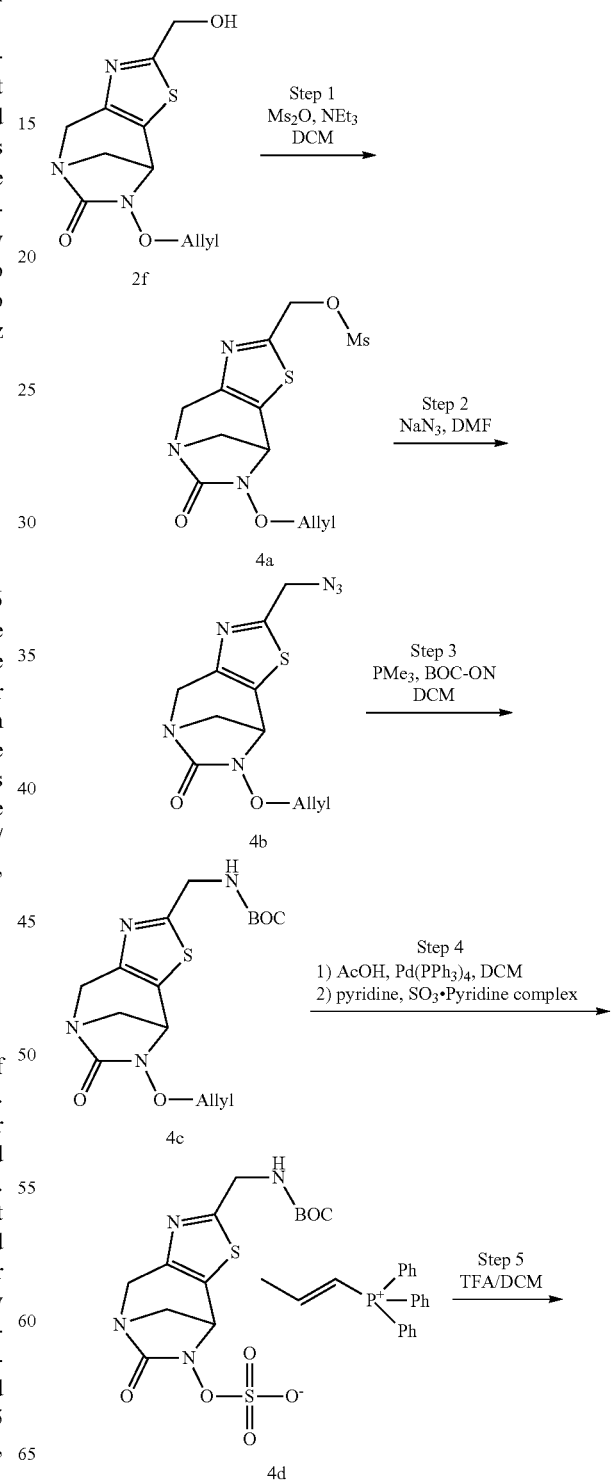

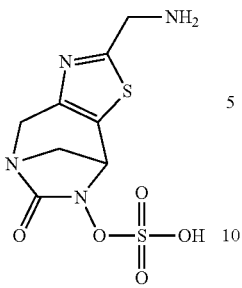

Example 4

Step 1: preparation of intermediate (7-allyloxy-5,8-methano-6-oxo-4,8-dihydrothiazolo[4,5-e][1,3]diazepin-2-yl)methyl methanesulfonate (4a)

Under argon atmosphere and at 0° C., TEA (0.15 mL, 1.12 mmol) and Ms$_2$O (130 mg, 0.75 mmol) were added to a solution of intermediate (2f) (100 mg, 0.37 mmol) in DCM (1.9 mL). The mixture was stirred at 0° C. for 1 h 30, diluted with DCM and washed with H$_2$O and brine. The organic layer was dried over Na$_2$SO$_4$, filtered and concentrated in vacuo to provide intermediate (4a) (118 mg) which was used in next step without purification. MS m/z ([M+H]$^+$) 346.

Step 2: preparation of intermediate 7-allyloxy-2-(azidomethyl)-5,8-methano-4,8-dihydrothiazolo[4,5-e][1,3]diazepin-6-one (4b)

Under argon atmosphere, NaN$_3$ (111 mg, 1.71 mmol) was added to a solution of intermediate (4a) (118 mg) in DMF (1.1 mL). The mixture was stirred at 60° C. for 1h, diluted with AcOEt and washed with H$_2$O and brine. The organic layer was dried over Na$_2$SO$_4$, filtered and concentrated in vacuo to provide intermediate (4b) (68 mg, 0.23 mmol, 63% on 2 steps) which was used in next step without purification. MS m/s ([M+H]$^+$) 293.

Step 3: preparation of intermediate tert-butyl N-[(7-allyloxy-5,8-methano-6-oxo-4,8-dihydrothiazolo[4,5-e][1,3]diazepin-2-yl)methyl]carbamate (4c)

Under argon atmosphere and at 0° C., PMe$_3$ 1M in THF (0.35 mL, 0.35 mmol)) was added to a solution of intermediate (4b) (68 mg) in THF (2.4 mL). The mixture was stirred at 0° C. for 45 min then BOC-ON (86 mg, 0.35 mmol) in solution in THF (0.5 mL) was added. The mixture was stirred at 0° C. for 1h and then concentrated. The residue was purified by flash chromatography on silica gel (DCM/acetone 10/0 to 4/6) to provide intermediate (4c) (51 mg, 57%). MS m/z ([M+H]$^+$) 367. $^1$H NMR (400 MHz, CDCl$_3$): δ (ppm) 1.46 (s, 9H), 3.21 (d, J=11.0 Hz, 1H), 3.70 (dd, J=2.9, 11.0 Hz, 1H), 4.33 (d, J=16.8 Hz, 1H), 4.33-4.50 (m, 3H), 4.53 (d, J=16.8 Hz, 1H), 4.57 (d, J=16.8 Hz, 1H), 5.25-5.38 (m, 3H), 5.93-6.04 (m, 1H).

Step 4: preparation of intermediate tert-butyl N-[(7-hydroxy-5,8-methano-6-oxo-4,8-dihydrothiazolo[4,5-e][1,3]diazepin-2-yl)methyl]carbamate (4d)

AcOH (16 μL, 0.27 mmol) and Pd(PPh$_3$)$_4$ (79 mg, 0.07 mmol) were successively added to a solution of intermediate (4c) (50 mg, 0.13 mmol) in anhydrous DCM (1.4 mL). After stirring for 1 h 30 at rt, pyridine (1.4 mL) and sulfur trioxide pyridine complex (108 mg, 0.68 mmol) were added and the mixture was stirred at rt overnight. The mixture was diluted with DCM and the solids were filtered off. The filtrate was concentrated and the residue was purified by flash chromatography on silica gel (DCM/acetone 10/0 to 0/10) to provide intermediate (4d) (75 mg, 0.10 mmol, 78%). MS m/z ([M−H]$^-$) 405.

Step 5: preparation of [2-(aminomethyl)-5,8-dimethyl-6-oxo-4,8-dihydrothiazolo[4,5-e][1,3]diazepin-7-yl] hydrogen sulfate, Example 4

At 0° C., TFA (0.3 mL) was added to a solution of intermediate (4d) (75 mg, 0.10 mmol) in DCM (0.1 mL). After 30 min at 0° C., conversion was not complete. TFA was so added at 0° C. until complete conversion. At 0° C., a precipitate was obtained by addition of Et2O and the supernatant was eliminated (operation repeated 3 times). The residue was triturated with ACN and supernatant was eliminated (operation repeated twice). The solid was filtered, dried under vacuum and purified twice by column chromatography on C18 (Water/ACN 99/1 to 50/50). The fractions containing the desired compound were combined, partially concentrated under flux of nitrogen to remove ACN, frozen and lyophilized to provide Example 4 as zwitterion (3.8 mg, 0.012 mmol, 12%). MS m/z ([M−H]$^-$) 306. $^1$H NMR (400 MHz, D$_2$O): δ (ppm) 3.60 (d, J=11.6 Hz, 1 H), 3.94 (dd, J=3.0, 11.6 Hz, 1H), 4.54 (d, J=16.9 Hz, 1H), 4.57 (s, 2H), 4.62 (d, J=16.9 Hz, 1H), 5.23 (d, J=2.9 Hz, 1H). $^{19}$F NMR (377 MHz, D$_2$O): no fluorine.

Example 9: synthesis of [trans-4-(dimethylcarbamoyl)-2-(2-guanidinoethylcarbamoyl)-5,8-methano-6-oxo-4,8-dihydrothiazolo[4,5-e][1,3]diazepin-7-yl] hydrogen sulfate

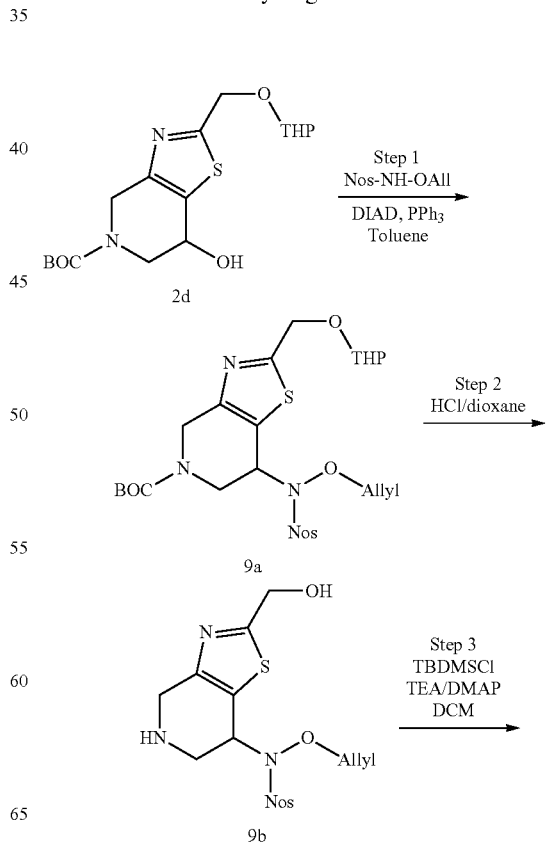

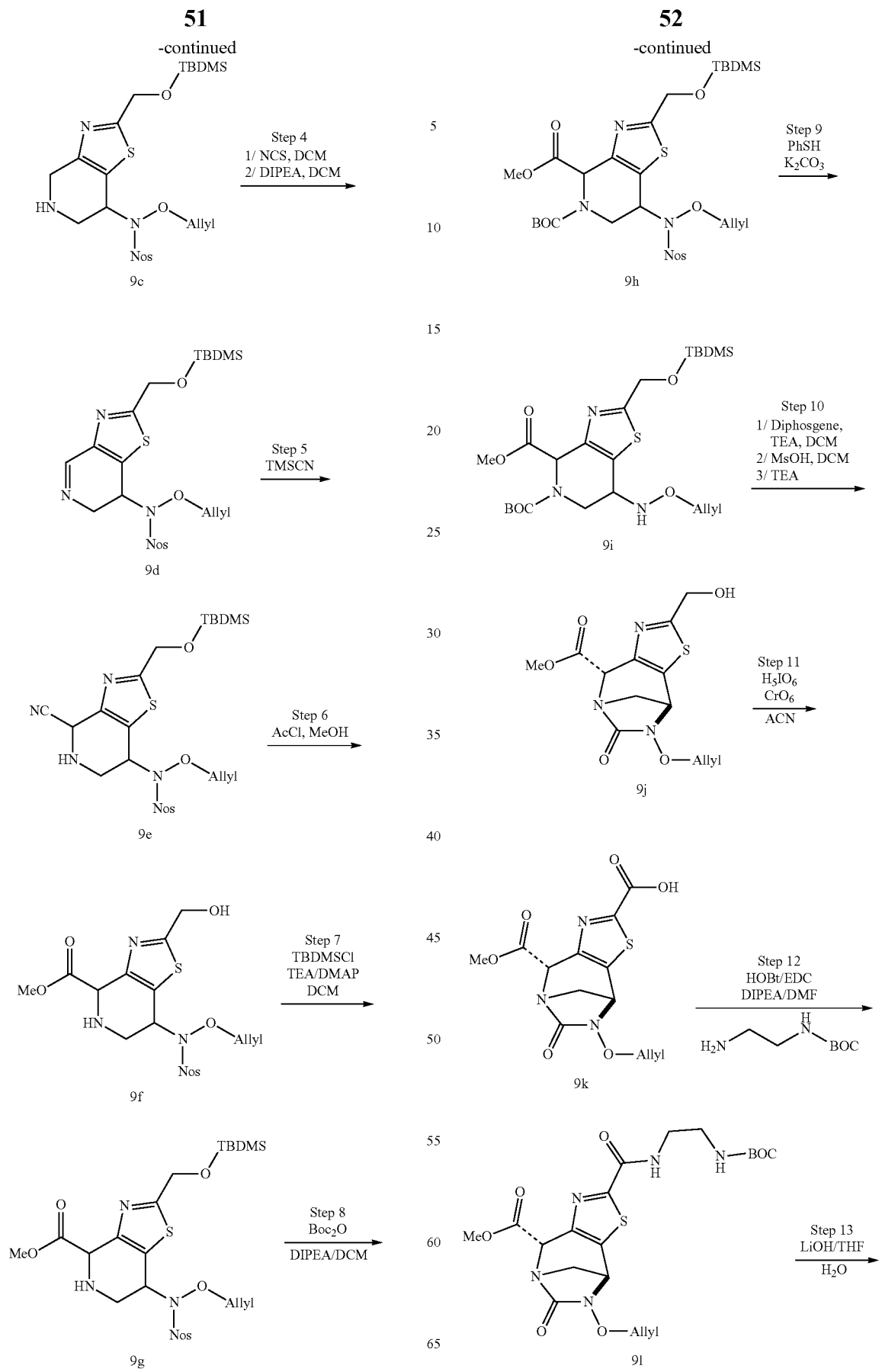

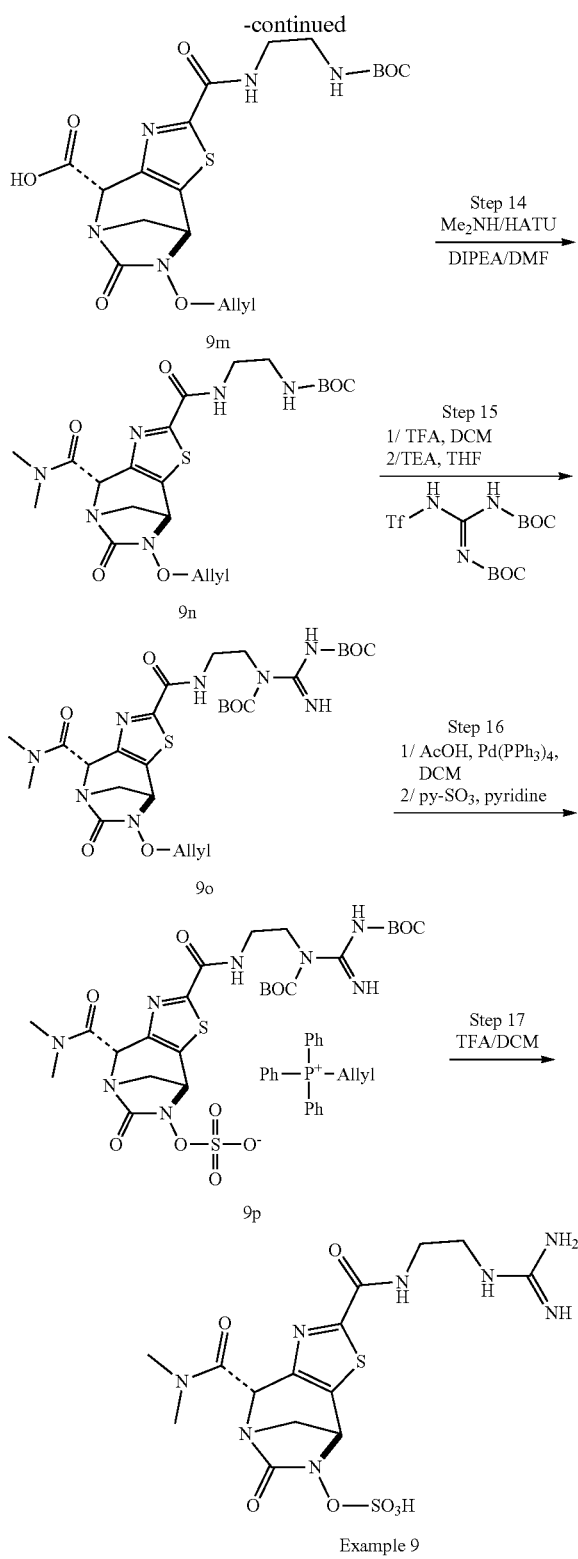

Example 9

Step 1: preparation of intermediate tert-butyl 7-[allyloxy-(2-nitrophenyl)sulfonyl-amino]-2-(tetrahydropyran-2-yloxymethyl)-6,7-dihydro-4H-thiazolo[4,5-c]pyridine-5-carboxylate (9a)

Under inert atmosphere, DIAD (10.47 g, 51.82 mmol) was added portionwise to a solution of intermediate (2d) (16 g, 43.18 mmol), N-allyloxy-2-nitro-benzenesulfonamide (13.38 g, 51.82 mmol) and PPh$_3$ (13.59 g, 51.8 mmol) in toluene (308 mL). The mixture was stirred at rt for 16 h and then concentrated. The crude product was purified by column chromatography on silica gel (DCM/Acetone: 10/0 to 8/2) to give intermediate (9a) (20.1 g, 31.27 mmol, 72%). MS m/z ([M+H]$^+$) 611. $^1$H NMR (400 MHz, CDCl$_3$): δ (ppm) 1.45 (s, 9H), 1.53-1.94 (m, 6H), 3.34-3.63 (m, 2H), 3.87 (t, J=10.2 Hz, 1H), 4.18 (s, 2H), 4.33 (d, J=17.2 Hz, 2H), 4.67-4.87 (m, 2H), 4.87-5.01 (m, 2H), 5.08 (d, J=10.2 Hz, 2H), 5.32 (s, 1H), 5.57 (s, 1H), 7.67 (d, J=7.8 Hz, 1H), 7.75-7.85 (m, 2H), 8.16 (dd, J=7.9, 1.5 Hz, 1H).

Step 2: preparation of intermediate N-allyloxy-N-[2-(hydroxymethyl)-4,5,6,7-tetrahydrothiazolo[4,5-c]pyridin-7-yl]-2-nitro-benzenesulfonamide hydrochloride (9b)

Under inert atmosphere intermediate (9a) (20 g, 32.88 mmol) was diluted in HCl 4N in dioxane (312 mL). The reaction mixture was stirred at rt for 1 h 20. The precipitate was filtered. The solid was successively washed with dioxane and Et$_2$O to give intermediate (9b) (15.1 g, 31.27 mmol, 95%). MS m/z ([M+H]$^+$) 427. $^1$H NMR (400 MHz, D$_2$O): δ (ppm) 3.64-3.73 (m, 1H), 3.81 (dd, J=3.5, 14.0 Hz, 1H), 3.90-3.99 (m, 1H), 4.05 (dd, J=6.3, 11.9 Hz, 1H), 4.30 (dd, J=1.5, 16.0 Hz, 1H), 4.44 (d, J=15.9 Hz, 1H), 4.82 (d, J=1.1 Hz, 2H), 4.89-5.02 (m, 2H), 5.37 (ddd, J=5.3, 10.3, 17.0 Hz, 1H), 5.67 (s, 1H), 7.88 (ddd, J=1.6, 7.3, 8.0 Hz, 1H), 7.92-8.03 (m, 2H), 8.20 (dd, J=1.4, 8.0 Hz, 1H).

Step 3: preparation of intermediate N-allyloxy-N-[2-[[tert-butyl(dimethyl)silyl]oxymethyl]-4,5,6,7-tetrahydrothiazolo[4,5-c]pyridin-7-yl]-2-nitro-benzenesulfonamide (9c)

Under inert atmosphere, intermediate (9b) (15.1 g, 32.6 mmol) was diluted in anhydrous DCM (65.2 mL). At 0° C., TBDMSCl (7.4 g, 48.9 mmol), TEA (13.6 mL, 97.8 mmol) and DMAP (398 mg, 3.3 mmol) were added. The mixture was stirred at rt for 16 h. The mixture was concentrated to dryness under reduced pressure. The crude product was purified by column chromatography on silica gel (DCM/Acetone: 10/0 to 6/4) to give intermediate (9c) (15.7 g, 28.46 mmol, 87%). MS m/z ([M+H]$^+$) 541. $^1$H NMR (400 MHz, CDCl$_3$): δ (ppm) 0.00 (s, 6H), 0.82 (s, 9H), 2.88 (dd, J=4.7, 14.6 Hz, 1H), 3.02 (s, 1H), 3.67 (d, J=17.0 Hz, 1H), 3.86 (d, J=17.0 Hz, 1H), 3.97 (s, 1H), 4.31 (dd, J=6.2, 11.3 Hz, 1H), 4.78 (s, 2H), 4.92-5.04 (m, 3H), 5.40-5.53 (m, 1H), 7.51 (dd, J=1.3, 7.9 Hz, 1H), 7.62 (td, J=1.4, 7.7 Hz, 1H), 7.66-7.72 (m, 1H), 8.01 (dd, J=1.5, 7.9 Hz, 1H).

Step 4: preparation of intermediate N-allyloxy-N-[2-[[tert-butyl(dimethyl)silyl]oxymethyl]-6,7-dihydrothiazolo[4,5-c]pyridin-7-yl]-2-nitro-benzenesulfonamide (9d)

Under inert atmosphere at 0° C. intermediate (9c) (4.94 g, 9.1 mmol) was diluted in DCM (55.4 mL). A solution of NCS (1.6 g, 11.9 mmol) in DCM (55.4 mL) was added dropwise. After stirring for 2h at 0° C., DIPEA (5.9 mL, 33.8 mmol) was added dropwise and the reaction mixture was stirred at rt for 16 h. The crude product was purified by column chromatography on silica gel (DCM/Acetone: 10/0 to 6/4) to give intermediate (9d) (4.44 g, 8.24 mmol, 83%). MS m/z ([M+H]$^+$) 539. $^1$H NMR (400 MHz, CDCl$_3$): δ (ppm) 0.14 (s, 6H), 0.96 (s, 9H), 3.76-3.91 (m, 1H), 4.02 (bs, 2H), 4.37 (dd, J=6.3, 11.2 Hz, 1H), 4.92 (d, J=5.4 Hz, 2H), 5.04-5.15 (m, 2H), 5.55 (m, 2H), 7.66 (dd, J=1.3, 7.9 Hz, 1H), 7.73 (td, J=1.3, 7.7 Hz, 1H), 7.82 (td, J=1.4, 7.7 Hz, 1H), 8.07 (d, J=7.9 Hz, 1H), 8.40 (s, 1H).

Step 5: preparation of intermediate N-allyloxy-N-[2-[[tert-butyl(dimethyl)silyl]oxymethyl]-4-cyano-4,5,6,7-tetrahydrothiazolo[4,5-c]pyridin-7-yl]-2-nitro-benzenesulfonamide (9e)

Under inert atmosphere at 0° C., intermediate (9d) (4.44 g, 8.24 mmol) was diluted in anhydrous DCM (57 mL). TMSCN (10.3 mL, 82.4 mmol) was added. The reaction mixture was stirred at rt for 46 h. The mixture was concentrated to dryness under reduced pressure. The crude product was purified by column chromatography on silica gel (DCM/Acetone: 10/0 to 8/2) to give intermediate (9e) (4.45 g, 7.9 mmol, 87%). MS m/z ([M+H]$^+$) 566. $^1$H NMR (400 MHz, CDCl$_3$): δ (ppm) 0.00 (s, 6H), 0.79 (s, 9H), 2.11 (s, 1H), 3.21 (d, J=13.9 Hz, 1H), 3.95 (s, 1H), 4.28 (dd, J=6.2, 11.3 Hz, 1H), 4.69-4.80 (m, 2H), 4.85 (s, 1H), 4.86-4.97 (m, 2H), 4.99 (dd, J=1.9, 3.5 Hz, 1H), 5.32-5.46 (m, 1H), 7.46-7.53 (m, 1H), 7.60 (td, J=1.3, 7.7 Hz, 1H), 7.68 (td, J=1.5, 7.7 Hz, 1H), 7.96 (dd, J=1.4, 7.9 Hz, 1H).

Step 6: preparation of intermediate methyl 7-[allyloxy-(2-nitrophenyl)sulfonyl-amino]-2-(hydroxymethyl)-4,5,6,7-tetrahydrothiazolo[4,5-c]pyridine-4-carboxylate (9f)

Under inert atmosphere at 0° C., acetyl chloride (7.8 mL, 110.2 mmol) was diluted in anhydrous MeOH (20 mL). After stirring for 2 h at rt, a solution of intermediate (9e) (4.45 g, 7.9 mmol) in anhydrous MeOH (9.8 mL) was added. The reaction mixture was heated at 50° C. for 16 h 30. The mixture was concentrated to dryness under reduced pressure. The residue was diluted with DCM and sat NaHCO$_3$. Aqueous layer was extracted with DCM. The combined organic layers were dried over Na$_2$SO$_4$, evaporated to dryness to give intermediate (9f) (3.55 g, 7.34 mmol, 83%). MS m/z ([M+H]$^+$) 485.

Step 7: preparation of intermediate methyl 7-[allyloxy-(2-nitrophenyl)sulfonyl-amino]-2-[[tert-butyl(dimethyl)silyl]oxymethyl]-4,5,6,7-tetrahydrothiazolo[4,5-c]pyridine-4-carboxylate (9Q)

Using the procedure described in example 9 (step 3), intermediate (9f) (3.55 g, 7.34 mmol) was converted into intermediate (9g) (3.31 g, 5.5 mmol, 71%) after purification by flash chromatography on silica gel (DCM/acetone: 100/0 to 60/40). MS m/z ([M+H]$^+$) 599.

Step 8: preparation of intermediate O5-tert-butyl O4-methyl 7-[allyloxy-(2-nitrophenyl)sulfonyl-amino]-2-[[tert-butyl(dimethyl)silyl]oxymethyl]-6,7-dihydro-4H-thiazolo[4,5-c]pyridine-4,5-dicarboxylate (9h)

Under inert atmosphere intermediate (9g) (3.31 g, 5.5 mmol) was diluted in anhydrous DCM (55 mL). DIPEA (1.25 mL, 7.19 mmol) and Boc$_2$O (1,57 g, 7.2 mmol) were successively added. After stirring for 65 h at rt, the mixture was concentrated to dryness under reduced pressure. The crude product was purified by column chromatography on silica gel (cyclohexane/EtOAc: 10/0 to 0/10) to give intermediate (9h) (3.52 g, 5.04 mmol, 87%) MS m/z ([M+H]$^+$) 699. $^1$H NMR (400 MHz, CDCl$_3$): δ (ppm) 0.00 (d, J=3.7 Hz, 6H), 0.83 (s, 9H), 1.30 (d, J=9.2 Hz, 9H), 3.38-3.73 (m, 4H), 4.00-4.48 (m, 3H), 4.80 (s, 2H), 4.85-5.08 (m, 2H), 5.09-5.31 (m, 1H), 5.31-5.76 (m, 2H), 7.54 (dd, J=8.3, 11.5 Hz, 1H), 7.60-7.76 (m, 2H), 7.95-8.10 (m, 1H).

Step 9: preparation of intermediate O5-tert-butyl O4-methyl 7-(allyloxyamino)-2-[[tert-butyl(dimethyl)silyl]oxymethyl]-6,7-dihydro-4H-thiazolo[4,5-c]pyridine-4,5-dicarboxylate (9i)

Under inert atmosphere, intermediate (9h) (3.52 g, 5.04 mmol) was diluted in anhydrous ACN (34 mL). Thiophenol (2.6 g, 25.2 mmol) and K$_2$CO$_3$ (5.22 g, 37.8 mmol) were successively added. The reaction mixture was stirred at rt for 2 h. The mixture was filtered over a pad of Célite® which was washed with ACN. The filtrate was concentrated to dryness under reduced pressure. The crude product was purified by column chromatography on silica gel (cyclohexane/EtOAc: 10/0 to 7/3) to give intermediate (9i) (2.59 g, 5.04 mmol, 95%). MS m/z ([M+H]$^+$) 514. $^1$H NMR (400 MHz, CDCl$_3$): δ (ppm) 0.00 (d, J=1.4 Hz, 6H), 0.82 (s, 9H), 1.24-1.43 (m, 9H), 3.32-3.43 (m, 1H), 3.66 (d, J=1.5 Hz, 3H), 4.07-4.68 (m, 4H), 4.80 (m, 2H), 5.00-5.33 (m, 2H), 5.36-5.70 (m, 1H), 5.82 (m, 1H).

Step 10: preparation of intermediate methyl trans-7-allyloxy-2-(hydroxymethyl)-5,8-methano-6-oxo-4,8-dihydrothiazolo[4,5-e][1,3]diazepine-4-carboxylate (9j)

Under inert atmosphere at 0° C., intermediate (9i) (2.59 g, 5.05 mmol) was diluted in anhydrous DCM (51 mL). TEA (1.06 mL, 7.58 mmol) was added. Diphosgene (427 μL, 3.54 mmol) was added dropwise. After stirring for 45 min at 0° C., a solution of MeSO$_3$H (4.92 mL, 75.77 mmol) in DCM (5.6 mL) was added dropwise. After stirring for 1 h at 0° C., TEA (14.08 mL, 101.03 mmol) was added dropwise. The reaction mixture was stirred at rt for 1 h. The reaction mixture was diluted with DCM and the solution was washed with H$_2$O and brine. The organic layer was dried over Na$_2$SO$_4$, filtered and concentrated in vacuo. The crude product was purified by column chromatography on silica gel (DCM/Acetone: 10/0 to 5/5) to give intermediate (9j) (1.195 g, 3.67 mmol, 73%). MS m/z ([M+H]$^+$) 326. $^1$H NMR (400 MHz, CDCl$_3$): δ (ppm) 3.64 (dd, J=2.9, 11.5 Hz, 1H), 3.77 (dd, J=0.8, 11.6 Hz, 1H), 3.88 (s, 3H), 4.46 (qdt, J=1.2, 6.7, 12.3 Hz, 2H), 4.65 (dd, J=0.7, 2.9 Hz, 1H), 4.91 (s, 2H), 5.28 (s, 1H), 5.30-5.47 (m, 2H), 6.00-6.05 (m, 1H).

Step 11: preparation of intermediate trans-7-allyloxy-4-methoxycarbonyl-5,8-methano-6-oxo-4,8-dihydrothiazolo[4,5-e][1,3]diazepine-2-carboxylic acid (9k)

Under inert atmosphere, periodic acid (1.38 g, 6.06 mmol) was diluted in ACN (16 mL) and water (1.2 mL). Chromium (VI)oxide (14.3 mg, 0.14 mmol) was added. Under inert atmosphere at 0° C. of intermediate (9j) (464 mg, 1.43 mmol) was diluted in ACN (16 mL). The previous solution was added dropwise over 30 min. The reaction mixture was stirred at rt for 1 h. The reaction mixture was diluted with DCM and the solution was washed with aq. citric acid 10%, brine, dried over Na$_2$SO$_4$ and concentrated in vacuo to give intermediate (9k) (305 mg, 0.89 mmol, 60%) which was used in next step without further purification. MS m/z ([M+H]$^+$) 340.

Step 12: preparation of intermediate (methyl trans-7-allyloxy-2-[2-(tert-butoxycarbonylamino)ethylcarbamoyl]-5,8-dimethyl-6-oxo-4,8-dihydrothiazolo[4,5-e][1,3]diazepine-4-carboxylate (9l)

Under inert atmosphere at 0° C., intermediate (9k) (305 mg, 0.89 mmol) was diluted in anhydrous DMF (3.9 mL). N-Boc-ethylenediamine (171 µL, 1.08 mmol), EDC (248 mg, 1.29 mmol), HOBt (166 mg, 1.08 mmol) and DIPEA (470 µL, 2.7 mmol), were successively added. After stirring for 19 h at 50° C., the mixture was diluted with EtOAc and the solution was washed with brine. The organic layer was dried over $Na_2SO_4$, filtered and concentrated in vacuo. The crude product was purified by column chromatography on silica gel (DCM/Acetone: 10/0 to 8/2) to give intermediate (9l) (183 mg, 0.32 mmol, 35%). MS m/z ([M+H]$^+$) 482. $^1$H NMR (400 MHz, CDCl$_3$): δ (ppm) 1.44 (s, 9H), 3.38 (s, 2H), 3.56 (qd, J=7.2, 13.8 Hz, 2H), 3.66 (dd, J=2.9, 11.7 Hz, 1 H), 3.79 (dd, J=0.8, 11.8 Hz, 1H), 3.89 (s, 3H), 4.46 (qdt, J=1.2, 6.6, 12.2 Hz, 2H), 4.62-4.75 (m, 1H), 4.89 (s, 1H), 5.30-5.47 (m, 3H), 5.98-6.03 (m, 1H), 7.49 (s, 1H).

Step 13: preparation of intermediate trans-7-allyloxy-2-[2-(tert-butoxycarbonylamino)ethylcarbamoyl]-5,8-methano-6-oxo-4,8-dihydrothiazolo[4,5-e][1,3]diazepine-4-carboxylic acid (9m)

Under inert atmosphere at 0° C. intermediate (9l) (183 mg, 0.32 mmol) was diluted in a mixture of THF (1.7 mL) and water (1.1 mL). A solution LiOH 1N (319 µL, 0.32 mmol) was added dropwise. After 1 h at rt, further LiOH 1N (62 µL, 0.06 mmol) was added at 0° C. After 2 h 20, further LiOH 1N (62 µL, 0.06 mmol) was added at 0° C. The mixture was stirred at rt for 1h more until complete consumption of intermediate (9l). At 0° C., the mixture was quenched by addition of HCl 1N to pH=2. The mixture was extracted with DCM. The organic layer was dried over $Na_2SO_4$, filtered and concentrated in vacuo to give intermediate (9m) (149 mg, 0.32 mmol, 100%) which was used in next step without further purification. MS m/z ([M+H]$^+$) 468.

Step 14: preparation of intermediate tert-butyl N-[2-[[trans-7-allyloxy-4-(dimethylcarbamoyl)-5,8-methano-6-oxo-4,8-dihydrothiazolo[4,5-e][1,3]diazepine-2-carbonyl]amino]ethyl]carbamate (9n)

Under inert atmosphere at 0° C. intermediate (9m) (199 mg, 0.43 mmol) was diluted in anhydrous DMF (1.8 mL). Dimethylamine hydrochloride (69 mg, 0.85 mmol), DIPEA (222 µL, 1.28 mmol) and HATU (178 mg, 0.47 mmol) were successively added. After stirring for 2 h at rt, the reaction mixture was diluted with EtOAc and the solution was washed with brine. The organic layer was dried over $Na_2SO_4$, filtered and concentrated in vacuo. The crude product was purified by column chromatography on silica gel (DCM/Acetone: 10/0 to 5/5) to give intermediate (9n) (274 mg, 0.40 mmol, 94%). MS m/z ([M+H]$^+$) 495. $^1$H NMR (400 MHz, CDCl$_3$): δ (ppm) 1.34-1.49 (m, 9H), 3.04 (d, J=1.5 Hz, 3H), 3.30 (s, 2H), 3.34 (d, J=1.5 Hz, 3H), 3.44-3.55 (m, 3H), 3.70 (d, J=11.3 Hz, 1H), 4.34-4.50 (m, 2H), 4.67 (t, J=2.0 Hz, 1H), 5.30-5.44 (m, 3H), 5.95-6.03 (m, 1H).

Step 15: preparation of intermediate tert-butyl N-[2-[[trans-7-allyloxy-4-(dimethylcarbamoyl)-5,8-methano-6-oxo-4,8-dihydrothiazolo[4,5-e][1,3]diazepine-2-carbonyl]amino]ethyl]-N-(N-tert-butoxycarbonylcarbamimidoyl)carbamate (9o)

At 0° C., TFA (1.73 mL) was added to a solution of intermediate (9n) (210 mg, 0.425 mmol) in DCM (4.2 mL). After stirring for 1 h at 0° C., the mixture was concentrated to dryness under reduced pressure. The residue was diluted in anhydrous THF (4,25 mL). TEA (180 µL, 1.27 mmol) and 2-(trifluoromethylsulfonyl)guanidine (332 mg, 0.85 mmol) were successively added. After stirring for 1 h 30 at rt, the mixture was concentrated to dryness under reduced pressure. The crude product was purified by column chromatography on silica gel (DCM/Acetone: 10/0 to 7/3) to give intermediate (9o) (152 mg, 0.23 mmol, 53%). MS m/z ([M+H]$^+$) 637. $^1$H NMR (400 MHz, CDCl$_3$): δ (ppm) 1.43 (m, 18H), 2.98 (s, 3H), 3.28 (s, 3H), 3.45 (m, 2H), 3.53-3.69 (m, 3H), 3.73 (d, J=11.4 Hz, 1H), 4.37 (qdt, J=1.2, 6.6, 12.4 Hz, 2H), 4.60 (d, J=2.6 Hz, 1H), 5.21-5.38 (m, 3H), 5.86-5.99 (m, 1H), 7.23 (s, 1H), 8.48 (s, 1H).

Step 16: preparation of intermediate allyl(triphenyl)phosphonium [trans-2-[2-[tert-butoxycarbonyl-(N-tert-butoxycarbonylcarbamimidoyl)amino]ethylcarbamoyl]1-4-(dimethylcarbamoyl)-5,8-methano-6-oxo-4,8-dihydrothiazolo[4,5-e][1,3]diazepin-7-yl] sulfate (9p)

AcOH (27 µL, 0.48 mmol) and Pd(PPh$_3$)$_4$ (138 mg, 0.12 mmol) were successively added to a solution of intermediate (9o) (152 mg, 0.24 mmol) in anhydrous DCM (4.9 mL). After 2 h 20 at rt, further AcOH (1.5 µL, 0.026 mmol) and Pd(PPh$_3$)$_4$ (70 mg, 0.06 mmol) were added. After 3 h 40 at rt, further AcOH (7 µL, 0.122 mmol) was added. After 4 h 30 at rt, conversion was not complete and phenylsilane (10.3 µL, 0.084 mmol) was added. The mixture was stirred at rt for 1 h 30 more until complete consumption of intermediate (9o). Pyridine (2.4 mL) and sulfur trioxide pyridine complex (190 mg, 1.19 mmol) were then added and the mixture was stirred at rt for the night. The heterogeneous mixture was diluted with DCM and solids were filtered off. The filtrate was concentrated and the crude was purified by column chromatography on silica gel (DCM/Acetone: 10/0 to 0/10) to give intermediate (9p) (100 mg, 0.10 mmol, 39%) which was used in next step without further purification. MS m/z ([M+H]$^+$) 677.

Step 17: synthesis of [trans-4-(dimethylcarbamoyl)-2-(2-guanidinoethylcarbamoyl)-5,8-methano-6-oxo-4,8-dihydrothiazolo[4,5-e][1,3]diazepin-7-yl] hydrogen sulfate, Example 9

At 0° C., TFA (0.455 mL) was added to a solution of intermediate (9p) (100 mg, 0.102 mmol) in DCM (1.02 mL). At 0° C., further TFA was added four times every 2 h per portion of 150 µL. The mixture was stirred for further 5 h 30 until complete conversion on intermediate (9p). The mixture was diluted in Et$_2$O. The precipitate was filtered and triturated in Et$_2$O and ACN. The crude was purified by column chromatography on C18 (Water/ACN 99/1 to 90/10). Fractions of interest were combined, partially concentrated in vacuo, frozen and lyophilized to provide Example 9 (27 mg, 0.057 mmol, 42%). MS m/z ([M+H]$^+$) 477. $^1$H NMR (400 MHz, D$_2$O): δ (ppm) 2.99 (s, 3H), 3.33 (s, 3H), 3.39 (dd, J=5.1, 6.4 Hz, 2H), 3.52-3.60 (m, 3H), 3.74 (dd, J=2.9, 12.1 Hz, 1H), 5.23 (d, J=2.5 Hz, 1H), 5.66 (s, 1H).

Example 10: synthesis of [N-[[trans-4-(dimethylcarbamoyl)-5,8-methano-6-oxo-7-sulfooxy-4,8-dihydrothieno[2,3-e][1,3]diazepin-3-yl]methyl]carbamimidoyl]ammonium 2,2,2-trifluoroacetate
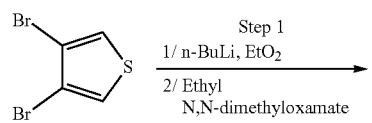
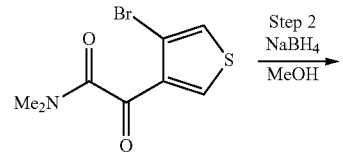
10a
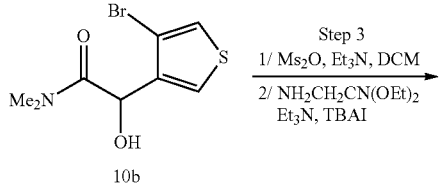
10b
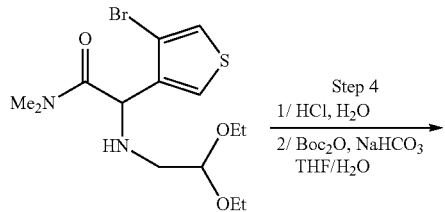
10c
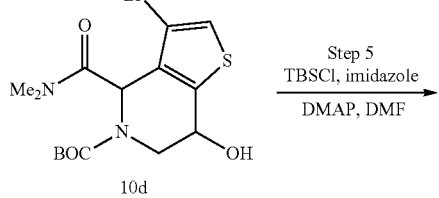
10d
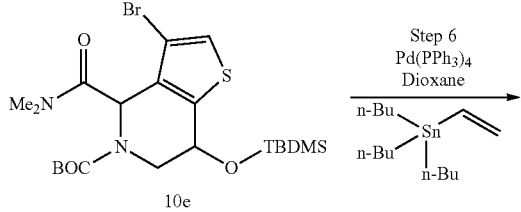
10e
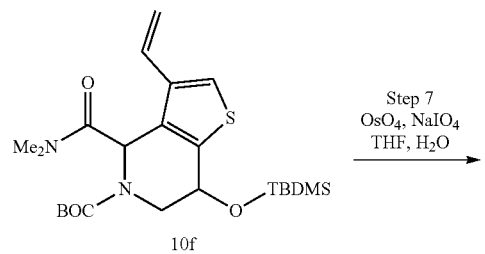
10f
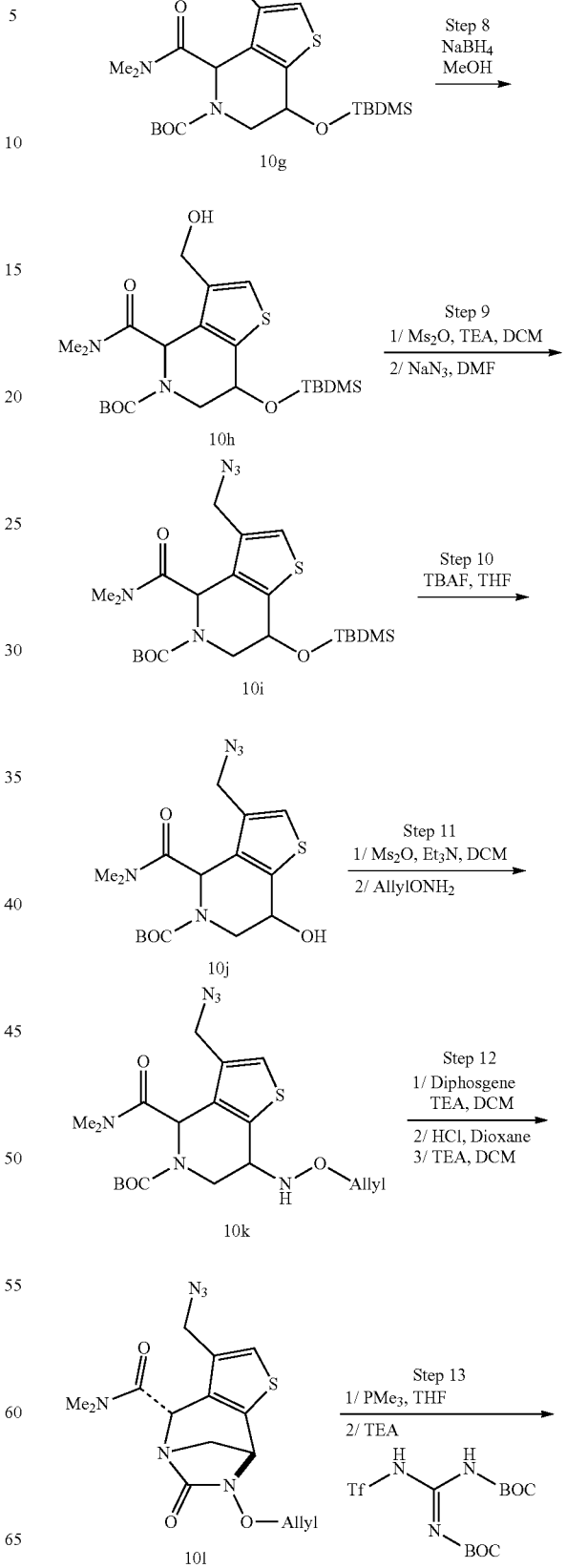

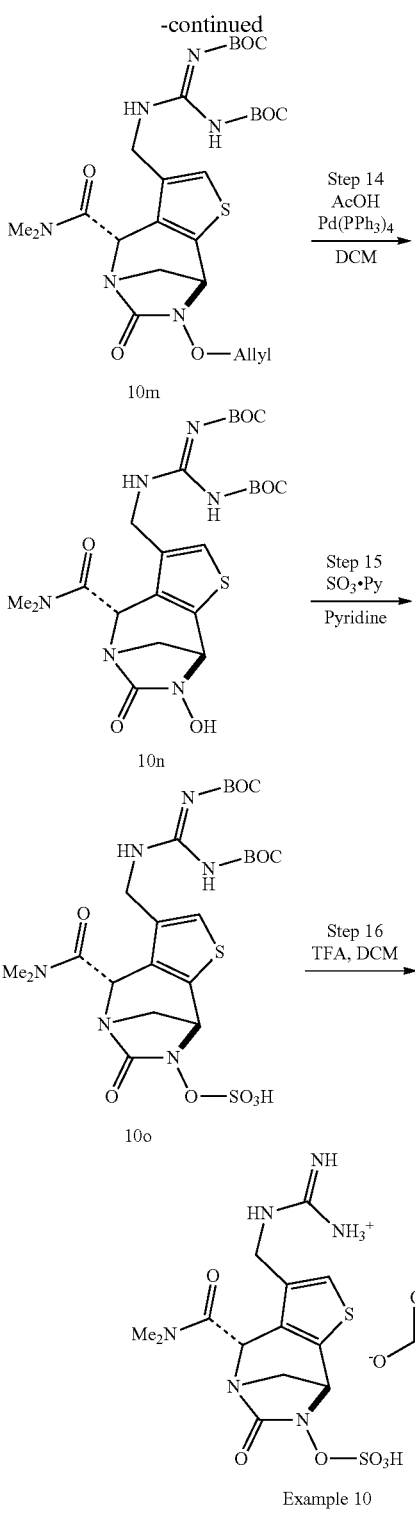

Example 10

Step 1: preparation of intermediate 2-(4-bromo-3-thienyl)-N,N-dimethyl-2-oxo-acetamide (10a)

At −78° C. under nitrogen atmosphere, to a solution of 3,4-dibromothiophene (10 g, 41.33 mmol) in anhydrous Et$_2$O (100 mL) was dropwise added a n-butyllithium solution 2.5 M in hexanes (18.2 mL, 45.47 mmol). The mixture was stirred at −78° C. for 20 min then added (via cannula) to a solution of ethyl N,N-dimethyloxamate (6.18 mL, 45.47 mmol) in anhydrous Et$_2$O (100 mL) at −78° C. The mixture was stirred at −78° C. for 30 min. Water (100 mL) was added and the mixture was stirred for 5 min at rt. The layers were separated. The aqueous layer was extracted with Et$_2$O (100 mL). The combined organic layers were dried over Na$_2$SO$_4$ and concentrated in vacuo to provide intermediate (10a) (8.72 g, 33.26 mmol, 80%) as a yellow oil which was used without further purification. MS m/z ([M+H]$^+$) 262/264. $^1$H NMR (400 MHz, CDCl$_3$): δ (ppm) 3.01 (s, 3H), 3.07 (s, 3H), 7.36 (d, J=3.5 Hz, 1H), 8.25 (d, J=3.5 Hz, 1H).

Step 2: preparation of intermediate 2-(4-bromo-3-thienyl)-2-hydroxy-N,N-dimethyl-acetamide (10b)

At 0° C., sodium borohydride (1.26 g, 33.26 mmol) was portionwise added to a solution of intermediate (10a) (8.72 g, 33.26 mmol) in methanol (100 mL). The mixture was stirred at 0° C. for 40 min then water (50 mL) was added. Methanol was evaporated in vacuo. The resulting solution was extracted with AcOEt (2×60 mL). The combined organic layers were dried over Na$_2$SO$_4$ and concentrated in vacuo. The residue was purified by flash chromatography on silica gel (cyclohexane/AcOEt 50/50 to 0/100) to provide intermediate (10b) (7.51 g, 28.43 mmol, 85% mmol) as a white solid. MS m/z ([M+H]$^+$) 264/266. $^1$H NMR (400 MHz, CDCl$_3$): δ (ppm) 2.74 (s, 3H), 3.05 (s, 3H), 4.00 (bs, 1H), 5.35 (s, 1H), 7.18 (d, J=3.4 Hz, 1H), 7.30 (d, J=3.4 Hz, 1H).

Step 3: preparation of intermediate 2-(4-bromo-3-thienyl)-2-(2,2-diethoxyethylamino)-N,N-dimethyl-acetamide (10c)

At 0° C., methanesulfonic anhydride (7.43 g, 42.65 mmol) was added to a solution of intermediate (10b) (7.51 g, 28.43 mmol) in DCM (120 mL) and TEA (7.9 mL, 56.86 mmol). The mixture was stirred at 0° C. for 1 h. Aminoacetaldehyde diethyl acetal (8.47 mL, 58.28 mmol), TEA (7.9 mL, 56.86 mmol) and tetrabutylammonium iodide (2.1 g, 5.68 mmol) were added and the mixture was stirred at rt overnight. The mixture was concentrated in vacuo. The residue was dissolved in MTBE (100 mL) and a saturated solution of NaHCO$_3$ (100 mL). Layers were separated. The aqueous layer was extracted with MTBE (100 mL). The organic layers were combined, dried over Na$_2$SO$_4$ and concentrated in vacuo. The residue was purified by flash chromatography on silica gel (DCM/acetone 100/0 to 60/40) to provide intermediate (10c) (10.08 g, 26.57 mmol, 93%). MS m/z ([M+H]$^+$) 379/381. $^1$H NMR (400 MHz, CDCl$_3$): δ (ppm) 1.10-1.27 (m, 6H), 2.59 (dd, J=5.8, 12.1 Hz, 1H), 2.80 (dd, J=5.2, 12.1 Hz, 1H), 2.89 (s, 3H), 2.97 (s, 3H), 3.43-3.59 (m, 2H), 3.60-3.73 (m, 2H), 4.60 (t, J=5.5 Hz, 1 H), 4.85 (s, 1H), 7.27 (d, J=3.5 Hz, 1 H), 7.28 (d, J=3.5 Hz, 1H).

Step 4: preparation of intermediate tert-butyl 3-bromo-4-(dimethylcarbamoyl)-7-hydroxy-6,7-dihydro-4H-thieno[3,2-c]pyridine-5-carboxylate (10d)

A mixture of intermediate (10c) (10.08 g, 26.57 mmol) in a hydrochloric acid solution (6M in water, 180 mL) was heated at 80° C. overnight. The mixture was filtered and the filtrate was concentrated in vacuo. The residue was dissolved in water (150 mL) and NaHCO$_3$ (17.8 g, 212.6 mmol) was carefully added. A solution of di-tert-butyl dicarbonate (8.12 g, 37.20 mmol) in THF (150 mL) was added and the mixture was stirred at rt overnight. THF was evaporated in vacuo. The aqueous solution was extracted with MTBE (2×150 mL). The organic layers were combined, washed with aqueous HCl 0.1M, brine, dried over $Na_2SO_4$ and concentrated in vacuo. The residue was purified by flash chromatography on silica gel (DCM/AcOEt 10/0 to 5/5) to provide intermediate (10d) as a (6.07 g, 14.97 mmol, 56%, mixture of trans and cis isomers) as a light yellow foam. MS m/z ([M+H]$^+$) 405/407. $^1$H NMR (400 MHz, $CDCl_3$): δ (ppm) 1.48 and 1.49 (s, 9H), 2.96-2.99 (m, 3H), 3.35-3.60 (m, 3.5H), 4.33 (d, J=14.4 Hz, 0.5H), 4.08 (dd, J=4.5, 12.7 Hz, 0.5H), 4.33 (d, J=14.4 Hz, 0.5H), 4.73-4.85 (m, 1H), 5.92 and 6.12 (2s, 1H), 7.19 and 7.23 (2s, 1H).

Step 5: preparation of intermediate tert-butyl 3-bromo-7-[tert-butyl(dimethyl)silyl]oxy-4-(dimethylcarbamoyl)-6,7-dihydro-4H-thieno[3,2-c]pyridine-5-carboxylate (10e)

To a solution of intermediate (10d) (6.07 g, 14.97 mmol) in DMF (60 mL) were successively added DMAP (183 mg, 1.50 mmol), imidazole (2.04 g, 29.95 mmol) and tert-butyldimethylsilyl chloride (3.38 g, 22.46 mmol). The mixture was stirred at rt for 2 h. Water (100 mL) was added. The mixture was extracted with MTBE (2×100 mL). The organic layers were combined, washed with brine (100 mL), dried over $Na_2SO_4$ and concentrated in vacuo. The residue was purified by flash chromatography on silica gel (n-heptane/AcOEt 10/0 to 5/5) to provide intermediate (10e) (6.61 g, 12.72 mmol, 84%, mixture of diastereoisomers) as a colorless oil. MS m/z ([M+Na]$^+$) 541/543, ([M+H]$^+$) 519/521. $^1$H NMR (400 MHz, $CDCl_3$): δ (ppm) 0.13-0.20 (m, 6H), 0.88-0.95 (m, 9H), 1.48 (s, 9H), 2.96 and 2.99 (s, 3H), 3.37-3.51 (m, 3.5H), 3.88 (dd, J=3.0, 13.9 Hz, 0.5H), 4.11 (dd, J=5.4, 12.9 Hz, 0.5H), 4.17 (d, J=14.0 Hz, 0.5H), 4.75 (dd, J=5.4, 10.1 Hz, 0.5H), 4.85 (dd, J=2.0, 2.9 Hz, 0.5H), 5.95 and 6.12 (2s, 1H), 7.13 and 7.18 (2s, 1H).

Step 6: preparation of intermediate tert-butyl 4-(dimethylcarbamoyl)-7-hydroxy-3-vinyl-6,7-dihydro-4H-thieno[3,2-c]pyridine-5-carboxylate (10f)

To a degassed solution of intermediate (10e) (1.0 g, 1.92 mmol) in dioxane (6.4 mL) were added tributyl(vinyl)tin (692 mg, 2.11 mmol) and $Pd(PPh_3)_4$ (111 mg, 0.10 mmol). The flask was sealed and the mixture was heated at 100° C. for 8 h. The mixture was filtered and the filtrate was concentrated in vacuo. The residue was purified by flash chromatography on silica gel (Petroleum Ether/AcOEt 10/0 to 5/5) to provide intermediate (10f) (897 mg, 1.92 mmol, 99%, mixture of diastereoisomers) as a solid. MS m/z ([M+H]) 467. $^1$H NMR (400 MHz, $CDCl_3$): δ (ppm) 0.15-0.20 (m, 6H), 0.91-0.95 (m, 9H), 1.48-1.54 (m, 9H), 2.94-2.97 (m, 3H), 3.32-3.44 (m, 3H), 3.82-4.19 (m, 2H), 4.79-4.86 (m, 1H), 5.14-5.20 (m, 1H), 5.44-5.51 (m, 1H), 6.01-6.17 (m, 1H), 6.29-6.42 (m, 1H), 7.16-7.18 (m, 1H).

Step 7: preparation of intermediate tert-butyl 4-(dimethylcarbamoyl)-3-formyl-7-hydroxy-6,7-dihydro-4H-thieno[3,2-c]pyridine-5-carboxylate (10g)

To a solution of intermediate (10f) (787 mg, 1.69 mmol) in $THF/H_2O$ (17/17 mL) were added $OsO_4$(4% in $H_2O$) (215 mL, 0.03 mmol) and $NaIO_4$ (905 mg, 4.22 mmol). The mixture was stirred at rt for 5 h. A saturated solution of $Na_2S_2O_3$ was added and the mixture was extracted twice with AcOEt. The organic layers were combined, washed with brine, dried over $Na_2SO_4$ and concentrated in vacuo. The residue was purified by flash chromatography on silica gel (DCM/AcOEt 10/0 to 6/4) to provide intermediate (10g) (800 mg, 1.69 mmol, 99%) as a solid. MS m/z ([M+H]$^+$) 469.

Step 8: preparation of intermediate tert-butyl 4-(dimethylcarbamoyl)-7-hydroxy-3-(hydroxymethyl)-6,7-dihydro-4H-thieno[3,2-c]pyridine-5-carboxylate (10h)

Under inert atmosphere, to a solution of intermediate (10g) (700 mg, 1.49 mmol) in MeOH (13 mL) was added $NaBH_4$ (80 mg, 2.09 mmol) at 0° C. The mixture was stirred at 0° C. for 30 min. Water was added and MeOH was evaporated in vacuo. The mixture was extracted twice with AcOEt. The organic layers were combined, washed with brine, dried over $Na_2SO_4$ and concentrated in vacuo to give crude product (10h) (560 mg, 1.19 mmol, 80%) as a white solid. MS m/z ([M+H]$^+$) 471.

Step 9: preparation of intermediate tert-butyl 3-(azidomethyl)-4-(dimethylcarbamoyl)-7-hydroxy-6,7-dihydro-4H-thieno[3,2-c]pyridine-5-carboxylate (10i)

To a solution of intermediate (10h) (415 mg, 0.88 mmol) in anhydrous DCM (8.8 mL) at −10° C. were successively added TEA (0.5 mL, 3.53 mmol) and methanesulfonic anhydride (460 mg, 2.64 mmol). The mixture was stirred at −10° C. for 30 min and at rt for 3 h. A saturated solution of $NaHCO_3$ was added and the mixture was extracted twice with DCM. The organic layers were combined, dried over $Na_2SO_4$ and concentrated in vacuo. The residue was solubilized in anhydrous DMF (4.3 mL) and sodium azide (256 mg, 3.9 mmol) was added. The mixture was stirred at rt for 30 min before being poured in a saturated solution of NaCl. The mixture was extracted twice with AcOEt. The organic layer was washed with brine, dried over $Na_2SO_4$ and concentrated in vacuo, to provide intermediate (10i) (509 mg, <100%) as a crude product. MS m/z ([M+H]$^+$) 496.

Step 10: preparation of intermediate tert-butyl 3-(azidomethyl)-4-(dimethylcarbamoyl)-7-hydroxy-6,7-dihydro-4H-thieno[3,2-c]pyridine-5-carboxylate (10j)

To a solution of intermediate (10i) (430 mg, 0.87 mmol) in anhydrous THF (4.3 mL) at 0° C. under inert atmosphere was added a solution of TBAF 1M in THF (1 mL, 1.04 mmol). The mixture was stirred at rt for 20 min then water was added to the mixture. The aqueous layer was extracted twice with AcOEt. The organic layers were combined, dried over $Na_2SO_4$ and concentrated in vacuo. The residue was purified by flash chromatography on silica gel (DCM/Acetone 10/0 to 8/2) to provide intermediate (10j) (330 mg, 0.86 mmol, 72%) as a white solid. MS m/z ([M+H]$^+$) 382.

Step 11: preparation of intermediate tert-butyl 7-(allyloxyamino)-3-(azidomethyl)-4-(dimethylcarbamoyl)-6,7-dihydro-4H-thieno[3,2-c]pyridine-5-carboxylate (10k)

To a solution of intermediate (10j) (236 mg, 0.62 mmol) in DCM (6.2 mL) at −78° C. were added TEA (0.30 mL, 2.16 mmol) and methanesulfonic anhydride (222 mg, 1.24 mmol). The mixture was stirred at −78° C. for 50 min. A solution of o-allylhydroxylamine 90% in DCM (350 mg, 4.33 mmol) was added and the mixture was stirred at rt for 4 h. Water was added. Layers were separated. The aqueous layer was extracted with DCM. The organic layers were combined, dried over $Na_2SO_4$ and concentrated in vacuo. The residue was purified by flash chromatography on silica gel (n-heptane/AcOEt 10/0 to 6/4) to provide intermediate (10k) (158 mg, 0.36 mmol, 60%) as a mixture of diastereoisomers. MS m/z ([M+H]$^+$) 437. $^1$H NMR (400 MHz, CDCl$_3$): δ (ppm) 1.49-1.51 (m, 9H), 3.0 (s, 3H), 3.34 (s, 3H), 3.65 (d, J=14.0 Hz, 1H), 4.05-4.55 (m, 5H), 5.19-5.40 (m, 2H), 5.73 (d, J=8.0 Hz, 1H), 5.90-6.02 (m, 1H), 6.09-6.18 (m, 1H), 6.38-6.85 (m,1H), 7.0-7.2 (m, 1H).

Step 12: preparation of intermediate trans-7-allyloxy-3-(2-azidomethyl)-5,8-methano-N,N-dimethyl-6-oxo-4,8-dihydrothieno[2,3-e][1,3]diazepine-4-carboxamide (10l)

To a solution of intermediate (10k) (155 mg, 0.36 mmol) in anhydrous DCM (2 mL) under inert atmosphere at 0° C. were added TEA (0.1 mL, 0.71 mmol) and diphosgene (34 µL, 0.278 mmol). The mixture was stirred at 0° C. for 2 h. A saturated solution of NaHCO$_3$ was added. The aqueous layer was extracted with DCM. The organic layers were combined, dried over $Na_2SO_4$ and concentrated in vacuo. The residue was solubilized in dioxane (0.5 mL) and a solution of HCl 4N in dioxane (2 mL, 7.1 mmol) was added. The mixture was stirred at rt for 5 h and then concentrated in vacuo. The residue was dissolved in DCM (2 mL) and TEA (0.2 mL, 0.73 mmol) was added. The mixture was stirred at rt overnight. Water was added. The aqueous layer was extracted with DCM. The organic layers were combined, dried over $Na_2SO_4$ and concentrated in vacuo. The residue was purified by flash chromatography on silica gel (DCM/AcOEt 10/0 to 5/5) to provide intermediate (10l ) as trans isomer (25 mg, 0.07 mmol, 19%, trans isomer) and the cis isomer (8 mg, 0.02 mmol, 5.5%) as white solids.

Trans isomer: MS m/z ([M+H]$^+$) 363. $^1$H NMR (400 MHz, CDCl$_3$): δ (ppm) 3.04 (s, 3H), 3.34 (s, 3H), 3.48 (dd, J=2.9, 11.0 Hz, 1H), 3.55 (dd, J=0.8, 11.1 Hz, 1H), 4.08 (dd, J=1.1, 14.2 Hz, 1H), 4.25 (dd, J=0.7, 14.1 Hz, 1H), 4.30-4.54 (m, 3H), 5.27-5.41 (m, 3H), 6.03 (ddt, J=6.3, 10.3, 16.9 Hz, 1H), 7.09 (s, 1H).

Cis isomer: MS m/z ([M+H]$^+$) 363. $^1$H NMR (400 MHz, CDCl$_3$): δ (ppm) 3.06 (s, 3H), 3.20 (d, J=10.8 Hz, 1H), 3.33 (s, 3H), 3.76 (dd, J=2.9, 10.7 Hz, 1H), 4.38-4.42 (m, 4H), 4.44 (d, J=2.8 Hz, 1H), 5.18 (s, 1H), 5.24-5.35 (m, 2H), 6.00 (ddt, J=6.3, 10.3, 16.7 Hz, 1H), 7.05 (d, J=0.9 Hz, 1H).

Step 13: preparation of intermediate tert-butyl N-[[[trans-7-allyloxy-4-(dimethylcarbamoyl)-5,8-methano-6-oxo-4,8-dihydrothieno[2,3-e][1,3]diazepin-3-yl]methylamino]-(tert-butoxycarbonylamino)methylene]carbamate (10m)

To a solution of intermediate (10l) (25 mg, 0.07 mmol) in anhydrous THF (0.7 mL) at 0° C. was added trimethylphosphine 1M in THF (0.1 mL, 0.1 mmol). The mixture was stirred at 0° C. for 2 h. Then, TEA (21 µL, 0.15 mmol) and 1,3-Di-Boc-2-(trifluoromethylsulfonyl)guanidine (35 mg, 0.09 mmol) were added at rt and the mixture was stirred for 2 h. The mixture was concentrated in vacuo. The residue was purified by flash chromatography on silica gel (n-Heptane/AcOEt 10/0 to 2/8) to provide intermediate (10m) (25 mg, 0.04 mmol, 62%) as a white solid. MS m/z ([M+H]$^+$) 579. $^1$H NMR (400 MHz, CDCl$_3$): δ (ppm) 1.49 (s, 9H), 1.51 (s, 9H), 3.00 (s, 3H), 3.31 (s, 3H), 3.45 (dd, J=2.9, 11.0 Hz, 1H), 3.58 (d, J=11.0 Hz, 1H), 3.99-4.29 (m, 2H), 4.30-4.59 (m, 4H), 5.14-5.47 (m, 2H), 6.02 (ddt, J=6.3, 10.3, 17.0 Hz, 1H), 7.10 (d, J=0.9 Hz, 1H), 8.45 (s, 1H), 11.46 (s, 1H).

Step 14: preparation of intermediate tert-butyl N-[(tert-butoxycarbonylamino)-[[trans-4-(dimethylcarbamoyl)-7-hydroxy-5,8-methano-6-oxo-4,8-dihydrothieno[2,3-e][1,3]diazepin-3-yl]methylamino]methylene]carbamate (10n)

To a solution of intermediate (10m) (24 mg, 0.04 mmol) in DCM (0.4 mL) were successively added Pd(PPh$_3$)$_4$ (24 mg, 0.02 mmol) and AcOH (17 µL, 0.304 mmol). The mixture was stirred at rt for 45 min. Further Pd(PPh$_3$)$_4$ (88 mg, 0.078 mmol) and AcOH (5 µL, 0.08 mmol) were added. The mixture was stirred for further 50 min. The mixture was concentrated in vacuo. The residue was purified by flash chromatography on silica gel (DCM/acetone 10/0 to 5/5) to provide intermediate (10n) (29 mg).

Step 15: preparation of intermediate tert-butyl N-[(tert-butoxycarbonylamino)-[[trans-4-(dimethylcarbamoyl)-5,8-methano-6-oxo-7-sulfooxy-4,8-dihydrothieno[2,3-e][1,3]diazepin-3-yl]methylamino]methylene]carbamate (10o)

A solution of intermediate (10n) in pyridine (400 µL) was heated at 40° C. in the presence of sulfur trioxide pyridine complex (33 mg, 0.2 mmol) for 2h. The mixture was concentrated in vacuo. The residue was triturated in DCM and filtered. The filtrate was concentrated in vacuo. The residue was purified by flash chromatography on silica gel (DCM/acetone 10/0 to 0/10) to provide intermediate (10o) (22 mg, 0.036 mmol, 89.5%). MS m/z ([M+H]$^+$) 619. MS m/z ([M-H]$^-$) 617.

Step 16: preparation of [N-[[trans-4-(dimethylcarbamoyl)-5,8-methano-6-oxo-7-sulfooxy-4,8-dihydrothieno[2,3-e][1,3]diazepin-3-yl]methyl]carbamimidoyl]ammonium 2,2,2-trifluoroacetate, Example 10

A mixture of intermediate (10o) (22 mg, 0.036 mmol) in DCM (0.4 mL) and TFA (3.3 mL) was stirred at 0° C. for 6 h. The mixture was diluted with Et$_2$O and the supernatant was removed (twice). The solid was triturated with ACN and filtered. The solid was washed with ACN and dried in vacuo in the presence of P$_2$O$_5$ to provide Example 10 (6 mg, 0.030 mmol, 36%) as TFA salt. MS m/z ([M+H]$^+$) 419. $^1$H NMR (400 MHz, DMSO-d$_6$): δ (ppm) 2.93 (s, 3H), 3.26 (s, 3H), 3.48 (dd, J=3.0, 11.2 Hz, 1H), 3.95 (dd, J=4.2, 15.7 Hz, 1H), 4.12 (dd, J=6.4, 15.8 Hz, 1H), 4.81 (d, J=2.7 Hz, 1H), 5.35 (s, 1H), 7.28 (s, 1H), 7.74 (d, J=6.0 Hz, 1H).

Example 11: synthesis [(trans-4-(dimethylcarbamoyl)-3-(2-quanidinoethyl)-5,8-methano-6-oxo-4,8-dihydrothieno[2,3-e][1,3]diazepin-7-yl] hydrogen sulfate

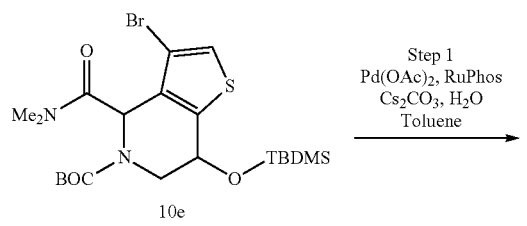
10e

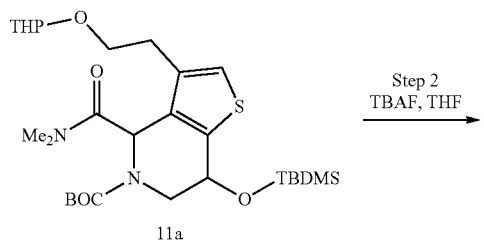
11a

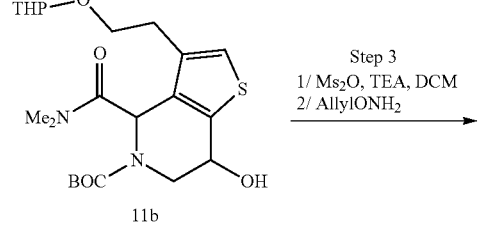
11b

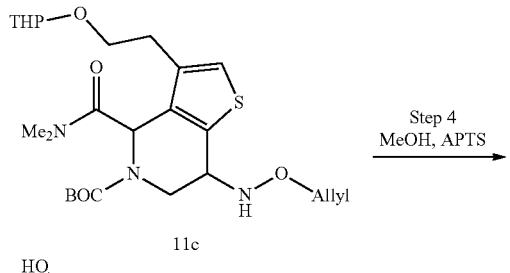
11c

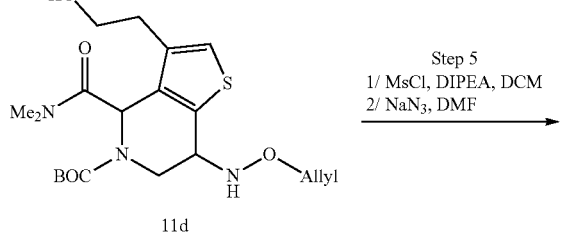
11d

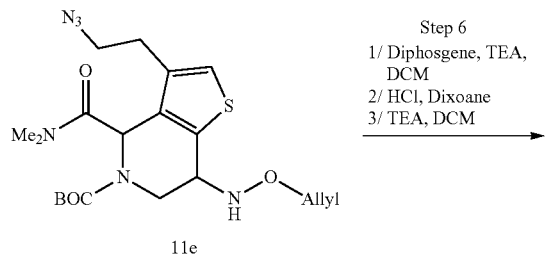
11e

Step 1
Pd(OAc)₂, RuPhos
Cs₂CO₃, H₂O
Toluene

Step 2
TBAF, THF

Step 3
1/ Ms₂O, TEA, DCM
2/ AllylONH₂

Step 4
MeOH, APTS

Step 5
1/ MsCl, DIPEA, DCM
2/ NaN₃, DMF

Step 6
1/ Diphosgene, TEA, DCM
2/ HCl, Dioxane
3/ TEA, DCM

-continued

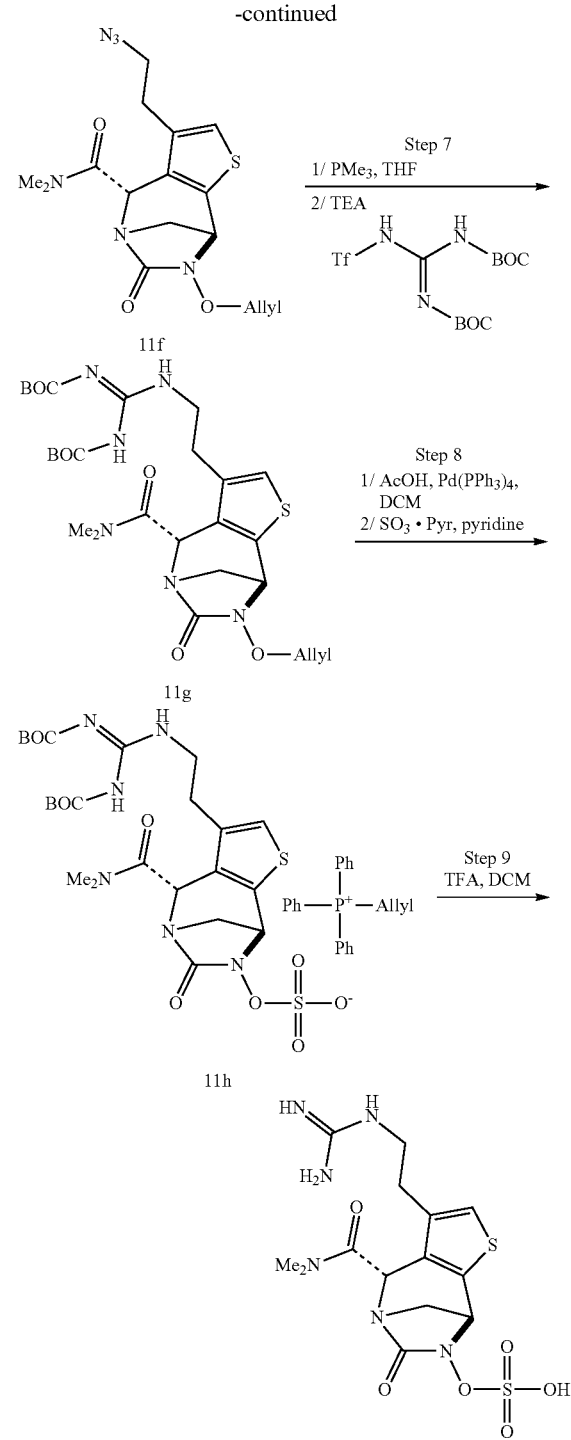

Example 11

Step 1: preparation of intermediate tert-butyl 7-[tert-butyl(dimethyl)silyl]oxy-4-(dimethylcarbamoyl)-3-(2-tetrahydropyran-2-yloxyethyl)-6,7-dihydro-4H-thieno[3,2-c]pyridine-5-carboxylate (11a)

To a degassed solution of intermediate (10e) (1.35 g, 2.60 mmol) in toluene (15 mL) and water (5 mL) were added potassium 2-(tetrahydro-2H-pyran-2-yloxy)ethyltrifluoroborate (613 mg, 2.60 mmol), cesium carbonate (2.54 g, 7.79 mmol), RuPhos (121 mg, 0.26 mmol) and palladium(II) acetate (29 mg, 0.13 mmol). The flask was sealed and the mixture was heated at 95° C. for 5 h. The mixture was cooled to rt and water was added. The layers were separated. The aqueous layer was extracted with toluene. The combined organic layers were washed with brine, dried over $Na_2SO_4$ and concentrated in vacuo. The residue was purified by flash chromatography on silica gel (cyclohexane/AcOEt 10/0 to 5/5) to provide intermediate (11a) (1.21 g, 2.12 mmol, 81%) as a yellow oil. MS m/z ($[M+Na]^+$) 591.

Step 2: preparation of intermediate tert-butyl 4-(dimethylcarbamoyl)-7-hydroxy-3-(2-tetrahydropyran-2-yloxyethyl)-6,7-dihydro-4H-thieno[3,2-c]pyridine-5- carboxylate (11b)

To a solution of intermediate (11a) (890 mg, 1.56 mmol) in anhydrous THF at 0° C. under inert atmosphere was added a solution of TBAF 1M in THF (2.35 mL, 2.35 mmol). The mixture was stirred at 0° C. for 2.5 h then concentrated in vacuo. The residue was purified by flash chromatography on silica gel (DCM/acetone 10/0 to 7/3) to provide intermediate (11b) (761 mg, quantitative) as a yellow oil. MS m/z ($[M+H]^+$) 455.

Step 3: preparation of intermediate tert-butyl 7-(allyloxyamino)-4-(dimethylcarbamoyl)-3-(2-tetrahydropyran-2-yloxyethyl)-6,7-dihydro-4H-thieno[3,2-c]pyridine-5- carboxylate (11c)

To a solution of intermediate (11b) (755 mg, 1.66 mmol) in DCM (10 mL) at −78° C. were added TEA (0.68 mL, 4.98 mmol) and methanesulfonic anhydride (434 mg, 2.49 mmol). The mixture was stirred at −78° C. for 45 min. A solution of o-allylhydroxylamine 50% in diethyl ether (1.14 g, 8.30 mmol) was added and the mixture was stirred at rt for 2.5 h. Water was added. Layers were separated. The aqueous layer was extracted with DCM. The organic layers were combined, dried over $Na_2SO_4$ and concentrated in vacuo. The residue was purified by flash chromatography on silica gel (DCM/acetone 10/0 to 8/2) to provide intermediate (11c) (603 mg, 1.18 mmol, 71%) as a yellow oil. MS m/z ($[M+Na]^+$) 532, m/z ($[M+H]^+$) 510.

Step 4: preparation of intermediate tert-butyl 7-(allyloxyamino)-4-(dimethylcarbamoyl)-3-(2-hydroxyethyl)-6,7-dihydro-4H-thieno[3,2-c]pyridine-5-carboxylate (11d)

A mixture of intermediate (11c) (443 mg, 0.87 mmol) and PPTS (328 mg, 1.30 mmol) in methanol (12 mL) was refluxed for 1 h. The mixture was filtered and the filtrate was concentrated in vacuo. The residue was purified by flash chromatography on silica gel (DCM/acetone 10/0 to 8/2) to provide intermediate (11d) (250 mg, 0.58 mmol, 67%) as a colorless oil. MS m/z ($[M+H]^+$) 426.

Step 5: preparation of intermediate tert-butyl 7-(allyloxyamino)-3-(2-azidoethyl)-4-(dimethylcarbamoyl)-6,7-dihydro-4H-thieno[3,2-c]pyridine-5-carboxylate (11e)

To a solution of intermediate (11d) (200 mg, 0.47 mmol) in anhydrous DCM (10 mL) at 0° C. were successively added DIPEA (0.123 mL, 0.705 mmol) and methanesulfonyl chloride (44 µL, 0.564 mmol). The mixture was stirred at 0° C. for 1 h. Water was added. The layers were separated. The aqueous layer was extracted with DCM. The organic layers were combined, dried over $Na_2SO_4$ and concentrated in vacuo. The residue was dissolved in anhydrous DMF (2.5 mL) and sodium azide (61 mg, 0.94 mmol) was added. The mixture was heated at 50° C. overnight before being poured in a saturated solution of $NaHCO_3$. The mixture was extracted twice with AcOEt. The organic layer was washed with brine, dried over $Na_2SO_4$ and concentrated in vacuo. The residue was purified by flash chromatography on silica gel (DCM/acetone 10/0 to 7/3) to provide intermediate (11e) (143 mg, 0.32 mmol, 67%, mixture of isomers) as a colorless oil. MS m/z ($[M+Na]^+$) 473, m/z ($[M+H]^+$) 451. $^1$H NMR (400 MHz, $CDCl_3$): δ (ppm) 1.47 and 1.48 (2s, 9H), 2.50-2.74 (m, 2H), 2.97 (s, 3H), 3.19-3.62 (m, 6H), 4.12-4.57 (m, 4H), 5.11-5.42 (m, 2H), 5.85-6.12 (m, 2H), 6.91 and 6.96 (2s, 1H).

Step 6: preparation of intermediate trans-7-allyloxy-3-(2-azidoethyl)-5,8-methano-N,N-dimethyl-6-oxo-4,8-dihydrothieno[2,3-e][1,3]diazepine-4-carboxamide (11f)

To a solution of intermediate (11e) (179 mg, 0.397 mmol) in anhydrous DCM (5 mL) under inert atmosphere at 0° C. were added TEA (83 µL 0.596 mmol) and diphosgene (34 µL 0.278 mmol). The mixture was stirred at 0° C. for 40 min. A saturated solution of $NaHCO_3$ (5 mL) was added. The aqueous layer was extracted with DCM. The organic layers were combined, dried over $Na_2SO_4$ and concentrated in vacuo. HCl 4N in dioxane (3.97 mL, 15.89 mmol) was added to the residue and the mixture was stirred at rt for 2 h before being concentrated in vacuo. The residue was dissolved in DCM (5 mL) and TEA (0.277 mL, 1.98 mmol) was added. The mixture was stirred at rt overnight. Water was added. The aqueous layer was extracted with DCM. The organic layers were combined, dried over $Na_2SO_4$ and concentrated in vacuo. The residue was purified by flash chromatography on silica gel (cyclohexane/AcOEt 5/5 to 0/10) to provide intermediate (11f) as trans isomer (70 mg, 0.185 mmol, 46%) and the cis isomer (40 mg, 0.106 mmol, 26%) as white solids.

Trans isomer: MS m/z ($[M+Na]^+$) 399, m/z ($[M+H]^+$) 377. $^1$H NMR (400 MHz, $CDCl_3$): δ (ppm) 2.51 (t, J=7.4 Hz, 2H), 3.03 (s, 3H), 3.34 (s, 3H), 3.36-3.53 (m, 3H), 3.56 (d, J=11.0 Hz, 1H), 4.34-4.49 (m, 3H), 5.23 (s, 1H), 5.25-5.41 (m, 2H), 5.93-6.08 (m, 1 H), 6.93 (s, 1H).

Cis isomer: MS m/z ($[M+Na]^+$) 399, m/z ($[M+H]^+$) 377. $^1$H NMR (400 MHz, $CDCl_3$): δ (ppm) 2.51-2.64 (m, 1H), 2.66-2.75 (m, 1H), 3.03 (s, 3H), 3.13 (d, J=10.7 Hz, 1H), 3.32 (s, 3H), 3.35-3.44 (m, 1H), 3.51-3.61 (m, 1H), 3.73 (dd, J=2.9, 10.7 Hz, 1H), 4.39 (d, J=6.3 Hz, 2H), 4.42 (d, J=2.8 Hz, 1H), 5.12 (s, 1H), 5.20-5.37 (m, 2H), 5.89-6.07 (m, 1H), 6.92 (s, 1H).

Step 7: preparation of intermediate tert-butyl N-[2-[trans-7-allyloxy-4-(dimethylcarbamoyl)-5,8-methano-6-oxo-4,8-dihydrothieno[2,3-e][1,3]diazepin-3- yl]ethyl]-N-(N-tert-butoxycarbonylcarbamimidoyl)carbamate (11g)

To a solution of intermediate (11f) (70 mg, 0.186 mmol) in anhydrous THF (2 mL) at 0° C. was added trimethylphosphine 1M in THF (0.28 mL, 0.28 mmol). The mixture was stirred at rt for 1 h before adding further trimethylphosphine 1M in THF (0.34 mL, 0.34 mmol). The stirring was resumed for 3 h. TEA (52 µL, 0.37 mmol) and 1,3-Di-Boc-2-(trifluoromethylsulfonyl)guanidine (95 mg, 0.242 mmol) were added and the mixture was stirred for 30 min. The mixture was concentrated in vacuo. The residue was purified by flash chromatography on silica gel (cyclohexane/AcOEt 8/2 to 2/8) to provide intermediate (11g) (90 mg, 0.152 mmol, 81%) as a colorless oil. MS m/z ($[M+H]^+$) 593. $^1$H NMR (400 MHz, $CDCl_3$): δ (ppm) 1.47 (s, 9H), 1.49 (s, 9H), 2.40-2.60 (m, 2H), 3.02 (s, 3H), 3.33 (s, 3H), 3.44 (dd, J=2.9, 11.0 Hz, 1H), 3.57 (d, J=11.0 Hz, 1H), 3.59-3.67 (m, 2H), 4.30-4.52 (m, 3H), 5.16 (s, 1H), 5.22-5.44 (m, 2H), 5.89-6.10 (m, 1H), 6.94 (s, 1H), 8.38 (s, 1H), 11.45 (s, 1H).

Step 8: preparation of intermediate allyl(triphenyl) phosphonium [trans-3-[2-[tert-butoxycarbonyl(ethanimidoyl)amino]ethyl]-4-(dimethylcarbamoyl)-5,8-methano-6-oxo-4,8- dihydrothieno[2,3-e][1,3]diazepin-7-yl] sulfate (11h)

To a solution of intermediate (11g) (90 mg, 0.152 mmol) in DCM (2 mL) were successively added Pd(PPh$_3$)$_4$ (88 mg, 0.078 mmol) and AcOH (17 µL, 0.304 mmol). The mixture was stirred at rt for 45 min. Further Pd(PPh$_3$)$_4$ (88 mg, 0.078 mmol) and AcOH (17 µL, 0.304 mmol) were added. The stirring was resumed for 45 min. Further Pd(PPh$_3$)$_4$ (44 mg, 0.038 mmol) and AcOH (9 µL, 0.15 mmol) were added. The stirring was resumed for 1 h. The mixture was concentrated in vacuo. The residue was co-evaporated twice with toluene. The residue was heated at 40° C. in the presence of pyridine (2 mL) and sulfur trioxide pyridine complex (121 mg, 0.76 mmol) for 2 h. The mixture was concentrated in vacuo. The residue was triturated in DCM and filtered. The filtrate was concentrated in vacuo. The residue was purified by flash chromatography on silica gel (DCM/acetone 10/0 to 0/10) to provide intermediate (11h) (90 mg, 0.096 mmol, 63%). MS m/z ([M−H]$^−$) 631.

Step 9: preparation of [(trans-4-(dimethylcarbamoyl)-3-(2-guanidinoethyl)-5,8-methano-6-oxo-4,8-dihydrothieno[2,3-e][1,3]diazepin-7-yl] hydrogen sulfate, Example 11

A mixture of intermediate (11h) (90 mg, 0.096 mmol), DCM (0.2 mL) and TFA (2 mL) was stirred at 0° C. for 5h. n-Heptane was added and the mixture was concentrated in vacuo. This operation was performed twice. The residue was purified by reversed phase chromatography on C18 (Water/acetonitrile 10/0 to 0/10). Fractions containing targeted compound were combined, frozen and lyophilized. The residue was stirred in water (1.5 mL) for 10 min. The solid was filtered. The solid was rinsed with water and dried in vacuo in the presence of P$_2$O$_5$ to provide Example 11 (13.3 mg, 0.030 mmol, 32%) as a white solid. MS m/z ([M+H]$^+$) 433. MS m/z ([M−H]$^−$) 431. $^1$H NMR (400 MHz, DMSO-d$_6$): δ (ppm) 2.34-2.45 (m, 1H), 2.50-2.57 (m, 1H), 2.93 (s, 3H), 3.29 (s, 3H), 3.31-3.37 (m, 3H), 3.46 (dd, J=3.0, 11.2 Hz, 1H), 4.78 (d, J=2.7 Hz, 1H), 5.29 (s, 1H), 7.15 (s, 1H), 7.40 (t, J=5.8 Hz, 1H).

| Example | Structure | |
|---|---|---|
| 4 COMPARATIVE | 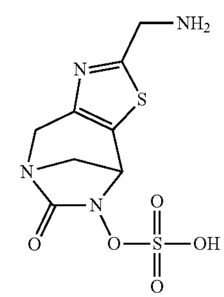 [SMILES: NCc1nc2c(s1)C1CN(C2)C(=O)N1OS(=O)(=O)O] | Covered by general formula in WO2004052891 (not described) |
| 5 COMPARATIVE | 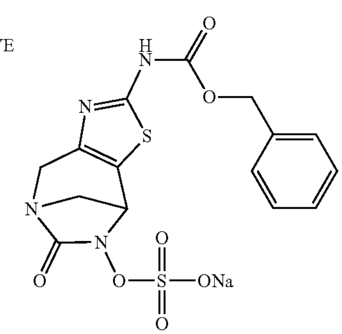 | Described as example 20 in WO2002100860 |
| 6 COMPARATIVE | 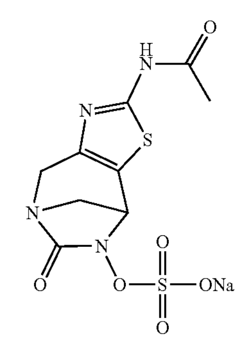 | Described as example 64 in WO2002100860 |

-continued

| Example | Structure | |
|---|---|---|
| 7 COMPARATIVE | [structure: thienyl-fused bicyclic urea with N-O-SO2-ONa] | Described as example 65 in WO2002100860 |
| 8 COMPARATIVE | [structure: 4-fluorophenyl-thienyl-fused bicyclic urea with ethyl ester and N-O-SO2-ONa] | Described as example 44 in WO2004052891 |

Biological Activity

MIC of Compounds and Synergy with Ceftazidime Against Bacterial Isolates (Table 1 and 2)

Compounds of the present invention were assessed against genotyped bacterial strains alone or in combination with the β-lactam ceftazidime. In the assays, MICs of said compounds, or of ceftazidime at fixed concentrations of said compounds were determined by the broth microdilution method according to the Clinical Laboratory Standards Institute (CLSI-M7-A7). Briefly, compounds alone according to the invention were prepared in DMSO and spotted (2 µL each) on sterile polystyrene plates (Corning, 3788). Compounds and ceftazidime dilutions were prepared in DMSO and spotted (1 µL each) on sterile polystyrene plates (Corning, 3788). Log phase bacterial suspensions were adjusted to a final density of $5 \times 10^5$ cfu/mL in cation-adjusted Mueller-Hinton broth (Beckton-Dickinson) and added to each well (98 µL Microplates were incubated for 16-20 h at 35° C. in ambient air. The MIC of the compounds was defined as the lowest concentration of said compounds that prevented bacterial growth as read by visual inspection.

The MIC of ceftazidime at each compound concentration was defined as the lowest concentration of ceftazidime that prevented bacterial growth as read by visual inspection.

TABLE 1

Bacterial species used in MIC determination

| Strains | | Resistance mechanism |
|---|---|---|
| E. coli | ECO 190317 | TEM-1, SHV-12, CTX-M-15, OXA-1 |
| E. coli | ECO UFR39 | CTX-M-15, NDM-1 |
| E. cloacae | ECL P99 | AmpC |
| K. pneumoniae | KPN 121206 | SHV-1, NDM-1 |
| P. aeruginosa | PAE 107051 | TEM-24, OXA-1 |
| P. aeruginosa | PAE UFR92 | derepressed AmpC, OprD- |
| P. aeruginosa | PAE 105250 (AH) | OXA-15 |
| P. aeruginosa | PAE UFR49 | VIM-2 |

TABLE 2

MIC of Ceftazidime (CAZ) and compounds alone (µg/mL)

MIC compounds of the invention alone (µg/mL)

| Compounds | ECO 190317 | ECO UFR39 | ECL P99 | KPN 121206 | PAE 107051 | PAE UFR92 | PAE 105250 (AH) | PAE UFR49 |
|---|---|---|---|---|---|---|---|---|
| CAZ | 128 | >256 | 128 | >256 | 256 | 32 | 256 | 64 |
| 1 | 0.25 | 0.5 | 2 | 32 | 8 | 8 | 8 | 16 |
| 2 | 0.063 | 0.125 | 1 | >32 | 2 | 4 | 4 | 4 |
| 3 | 0.5 | 2 | 0.5 | 16 | 4 | 8 | 8 | 16 |
| 4 | 0.25 | 0.25 | 1 | 32 | >32 | 32 | 32 | 32 |

TABLE 2-continued

MIC of Ceftazidime (CAZ) and compounds alone (µg/mL)

MIC compounds of the invention alone (µg/mL)

| Compounds | ECO 190317 | ECO UFR39 | ECL P99 | KPN 121206 | PAE 107051 | PAE UFR92 | PAE 105250 (AH) | PAE UFR49 |
|---|---|---|---|---|---|---|---|---|
| COMPARATIVE 5 | >32 | >32 | >32 | >32 | >32 | >32 | >32 | >32 |
| COMPARATIVE 6 | 2 | 4 | 16 | >32 | >32 | >32 | >32 | >32 |
| COMPARATIVE 7 | 2 | 4 | 8 | >32 | >32 | >32 | >32 | >32 |
| COMPARATIVE 8 | >32 | >32 | >32 | >32 | >32 | >32 | >32 | >32 |
| COMPARATIVE 9 | 32 | >32 | >32 | >32 | 8 | 32 | 8 | 4 |
| 10 | 2 | 32 | 16 | 32 | 4 | 8 | 8 | 8 |
| 11 | 4 | >32 | 16 | >32 | 4 | 8 | 4 | 4 |

TABLE 3

MIC of Ceftazidime (CAZ) alone and CAZ/compound combinations combination of CAZ and compounds of the invention at 4 µg/mL: MIC (µg/mL)

| Compounds | ECO 190317 | ECO UFR39 | ECL P99 | KPN 121206 | PAE 107051 | PAE UFR92 | PAE 105250 (AH) | PAE UFR49 |
|---|---|---|---|---|---|---|---|---|
| CAZ | 128 | >256 | 128 | >256 | 256 | 32 | 256 | 64 |
| CAZ + 1 | <0.125 | <0.125 | <0.125 | >128 | 4 | 4 | 32 | 32 |
| CAZ + 2 | <0.125 | <0.125 | <0.125 | >128 | <0.125 | <0.125 | <0.125 | <0.125 |
| CAZ + 3 | <0.125 | <0.125 | <0.125 | >128 | <0.125 | 8 | <0.125 | 64 |
| CAZ + 4 | <0.125 | <0.125 | <0.125 | >128 | 4 | 8 | 128 | 64 |
| COMPARATIVE CAZ + 5 | 128 | >128 | >128 | >128 | >128 | 32 | >128 | 64 |
| COMPARATIVE CAZ + 6 | <0.125 | <0.125 | 1 | >128 | 8 | 32 | >128 | 64 |
| COMPARATIVE CAZ + 7 | <0.125 | <0.125 | <=0.125 | >128 | 16 | 32 | >128 | 64 |
| COMPARATIVE CAZ + 8 | 128 | >128 | 64 | >128 | >128 | 32 | >128 | 64 |
| COMPARATIVE CAZ + 9 | 64 | >128 | 128 | >128 | 16 | 32 | 64 | 0.5 |
| CAZ + 10 | <0.125 | >128 | 32 | >128 | <0.125 | 32 | 16 | 8 |
| CAZ + 11 | <0.125 | >128 | 128 | >128 | <0.125 | 16 | 0.125 | 0.25 |

The invention claimed is:

1. A compound of formula (I), in which:

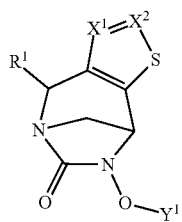

(I)

wherein:
R$^1$ is chosen in the group consisting of H, C(=O)NR$^2$R$^3$;
n is an integer comprised between 1 and 6;
R$^2$ and R$^3$, identical or different, are chosen in the group consisting of H, linear or branched (C1-C6)alkyl optionally substituted by one or more R$^5$;
R$^5$ is C(=O)NH$_2$;

Y$^1$ is chosen in the group consisting of SO$_3$H, CHFC(=O)Y$^2$ and CF$_2$C(=O)Y$^2$, SO$_3$(C1-C6)alkyl-C(=O)O(C1-C6)alkyl;

Y$_2$ is chosen in the group consisting of OH, O(C1-C6) alkyl linear or branched, O(C3-C11)cycloalkyl, O-(4 to 6-membered)heterocyclyl comprising 1 or 2 heteroatom independently chosen in the group consisting of N, O and S;

NY$^3$Y$^4$, wherein the alkyl, cycloalkyl and heterocyclyl are optionally substituted by one or more Y$^5$;

Y$^3$ and Y$^4$, each identical or different, is chosen in the group consisting of linear or branched (C1-C6)alkyl, linear or branched O(C1-C6)alkyl, (C3-C11)cycloalkyl, (4 to 6-membered)heterocyclyl comprising 1 or 2 heteroatoms independently chosen in the group consisting of N, O or S, or form together with the nitrogen atom to which they are linked a (4 to 6-membered) heterocyclyl comprising 1 or 2 heteroatoms independently chosen in the group consisting of N, O or S; wherein the alkyl, cycloalkyl and heterocyclyl is optionally substituted by one or more Y$^5$;

Y⁵, each identical or different, is chosen in the group consisting of linear or branched (C1-C6)alkyl, (C3-C6) cycloalkyl, linear or branched O(C1-C6)alkyl, linear or branched O(C1-C6)alkyl-O(C1-C6)alkyl, linear or branched (C1-C6)alkyl-O(C1-C6)alkyl; and O(C3-C6) cycloalkyl;

X¹=X² is chosen in the group consisting of N=CX⁴, CX³=CA¹ and CA¹=CX⁴;

A¹ is chosen in the group consisting of H and a halogen;

X³ and X⁴ is chosen in the group consisting of (CH₂)ₘ—C(=O)NX⁶X⁷, (CH₂)ₙ—NX⁶X⁷, (CH₂)ₙ—NX⁶C(=O)X⁷, (CH₂)ₙ—NHC(=NX⁶)NHX⁷, (CH₂)ₘ-(5- to 6-membered heteroaryl comprising from 1 to 4 heteroatom independently chosen in the group consisting of N, O, S), wherein the heteroaryl is substituted at least by one or more Z³;

m is an integer comprised between 0 and 6;

X⁶, X⁷ and X⁸, each identical or different, are chosen in the group consisting of H, linear or branched (C1-C6) alkyl-Z³;

Z¹ and Z², each identical or different are chosen in the group consisting of H, linear or branched (C1-C6)alkyl;

Z³, each identical or different, is chosen in the group consisting of (CH₂)ₘ—NZ¹Z², (CH₂)ₘ—NHC(=NH)NHZ¹;

Z⁴ represents H or linear or branched (C1-C6)alkyl;

any sulphur atom present within a heterocycle can be oxidized to form a S=O group or a S(O)₂ group;

any nitrogen atom present within a heterocycle or present within group wherein it is trisubstituted thus forming a tertiary amino group, can be further quaternized by a methyl group; or a racemate, an enantiomer, a diastereoisomer, a geometric isomer or a pharmaceutically acceptable salt thereof, with the exception that if one of X³ or X⁴ represent (CH₂)ₘ—C(=O)NX⁶X⁷, or (CH₂)ₙ—NX⁶X⁷ then at least one of X⁶ or X⁷ is different from H.

2. The compound of claim 1, wherein:

R¹ is chosen in the group consisting of H and C(=O)NR²R³; and/or

Y¹ is chosen in the group consisting of SO₃H, CHFC(=O)Y² and CF₂C(=O)Y².

3. The compound of claim 1 having a structure corresponding to formula (IA):

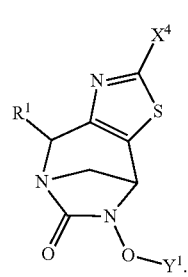

(IA)

4. The compound of claim 1 having a structure corresponding to formula (IB):

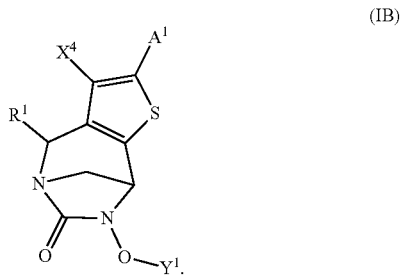

(IB)

5. The compound of claim 1 having a structure corresponding to formula (IC):

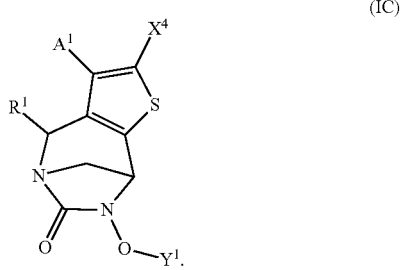

(IC)

6. The compound of claim 1 have a structure corresponding to formula (I*), formula (IA*), formula (IB*), or formula (IC*):

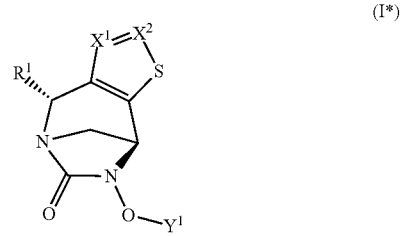

(I*)

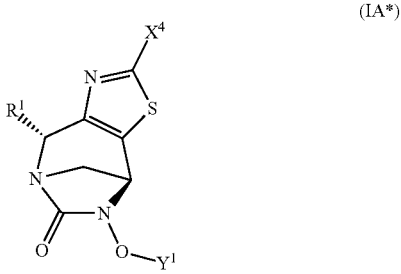

(IA*)

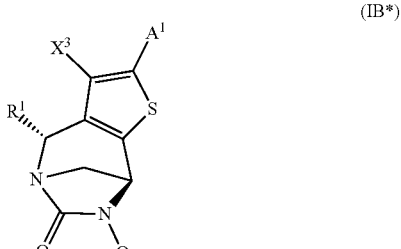

(IB*)

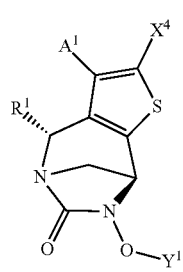

(IC*)

7. The compound of claim 1 selected from the group consisting of:
 [2-(2-aminoethylcarbamoyl)-5,8-methano-6-oxo-4,8-dihydrothiazolo[4,5-e][1,3]diazepin-7-yl]sulfonic acid;
 [2-(guanidinomethyl)-5,8-methano-6-oxo-4,8-dihydrothiazolo[4,5-e][1,3]diazepin-7-yl]sulfonic acid;
 [2-(2-guanidinoethylcarbamoyl)-5,8-methano-6-oxo-4,8-dihydrothiazolo[4,5-e][1,3]diazepin-7-yl]sulfonic acid;
 [trans-4-(dimethylcarbamoyl)-2-(2-guanidinoethylcarbamoyl)-5,8-methano-6-oxo-4,8-dihydrothiazolo[4,5-e][1,3]diazepin-7-yl] hydrogen sulfate;
 [N-[[trans-4-(dimethylcarbamoyl)-5,8-methano-6-oxo-7-sulfooxy-4,8-dihydrothieno[2,3-e][1,3]diazepin-3-yl]methyl]carbamimidoyl]ammonium 2,2,2- trifluoroacetate;
 [(trans-4-(dimethylcarbamoyl)-3-(2-guanidinoethyl)-5,8-methano-6-oxo-4,8-dihydrothieno[2,3-e][1,3]diazepin-7-yl] hydrogen sulfate.

8. A pharmaceutical composition comprising a compound according to claim 1 and a pharmaceutically acceptable excipient.

9. The pharmaceutical composition according to claim 8 further comprising an antibacterial compound.

10. The pharmaceutical composition according to claim 9 wherein the antibacterial compound is selected from aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins and mixtures thereof.

11. The pharmaceutical composition according to claim 8 further comprising a β-lactam compound.

12. The pharmaceutical composition according to claim 11, the β-lactam compound is selected from the group consisting of penicillin, cephalosporins, penems, carbapenems, monobactam, and combinations thereof.

13. A pharmaceutical composition comprising a compound according to claim 1 and ceftazidime.

14. A kit comprising:
 a first pharmaceutical composition that comprises a first pharmaceutically active compound a first pharmaceutically acceptable excipient; and
 a second pharmaceutical composition that comprises a second pharmaceutically active compound and second pharmaceutically acceptable excipient;
wherein the first and second pharmaceutically active compounds are different compounds according to claim 1.

15. A kit comprising:
 a first pharmaceutical composition comprising the compound of claim 1; and
 a second pharmaceutical composition comprising ceftazidime.

16. A method for treating a bacterial infection caused by Escherichia species, Enterobacter species or P.aeruginosa, the method comprising the administration to a person in need thereof of a compound of formula (I), in which:

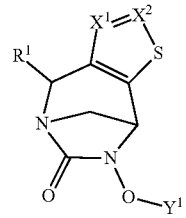

(I)

wherein:
 $R^1$ is chosen in the group consisting of H, $C(=O)NR^2R^3$;
 n is an integer comprised between 1 and 6;
 $R^2$ and $R^3$, identical or different, are chosen in the group consisting of H, linear or branched (C1-C6)alkyl optionally substituted by one or more $R^5$;
 $R^5$ is $C(=O)NH_2$;
 $Y^1$ is chosen in the group consisting of $SO_3H$, $CHFC(=O)Y^2$ and $CF_2C(=O)Y^2$, $SO_3$(C1-C6)alkyl-C(=O)O(C1-C6)alkyl;
 $Y^2$ is chosen in the group consisting of OH, O(C1-C6) alkyl linear or branched, O(C3-C11)cycloalkyl, O-(4 to 6-membered)heterocyclyl comprising 1 or 2 heteroatom independently chosen in the group consisting of N, O and S;
 $NY^3Y^4$, wherein the alkyl, cycloalkyl and heterocyclyl are optionally substituted by one or more $Y^5$;
 $Y^3$ and $Y^4$, each identical or different, is chosen in the group consisting of linear or branched (C1-C6)alkyl, linear or branched O(C1-C6)alkyl, (C3-C11)cycloalkyl, (4 to 6-membered)heterocyclyl comprising 1 or 2 heteroatoms independently chosen in the group consisting of N, O or S, or form together with the nitrogen atom to which they are linked a (4 to 6-membered) heterocyclyl comprising 1 or 2 heteroatoms independently chosen in the group consisting of N, O or S; wherein the alkyl, cycloalkyl and heterocyclyl is optionally substituted by one or more $Y^5$;
 $Y^5$, each identical or different, is chosen in the group consisting of linear or branched (C1-C6)alkyl, (C3-C6) cycloalkyl, linear or branched O(C1-C6)alkyl, linear or branched O(C1-C6)alkyl-O(C1-C6)alkyl, linear or branched (C1-C6)alkyl-O(C1-C6)alkyl; and O(C3-C6) cycloalkyl;
 $X^1=X^2$ is chosen in the group consisting of $N=CX^4$, $CX^3=CA^1$ and $CA^1=CX^4$;
 $A^1$ is chosen in the group consisting of H and a halogen;
 $X^3$ and $X^4$ is chosen in the group consisting of $(CH_2)_m$—$C(=O)NX^6X^7$, $(CH_2)_n$—$NX^6X^7$, $(CH_2)_n$—$NX^6C(=O)X^7$, $(CH_2)_n$—$NHC(=NX^6)NHX^7$, $(CH^2)_m$-(5- to 6-membered heteroaryl comprising from 1 to 4 heteroatom independently chosen in the group consisting of N, O, S), wherein the heteroaryl is substituted at least by one or more $Z^3$;
 m is an integer comprised between 0 and 6;
 $X^6$, $X^7$ and $X^8$, each identical or different, are chosen in the group consisting of H, linear or branched (C1-C6) alkyl-$Z^3$;
 $Z^1$ and $Z^2$, each identical or different are chosen in the group consisting of H, linear or branched (C1-C6)alkyl;
 $Z^3$, each identical or different, is chosen in the group consisting of $(CH_2)_m$—$NZ^1Z^2$, $(CH_2)_m$—$NHC(=NH)NHZ^1$;

$Z^4$ represents H or linear or branched (C1-C6)alkyl;

any sulphur atom present within a heterocycle can be oxidized to form a S=O group or a $S(O)_2$ group;

any nitrogen atom present within a heterocycle or present within group wherein it is trisubstituted thus forming a tertiary amino group, can be further quaternized by a methyl group; or a racemate, an enantiomer, a diastereoisomer, a geometric isomer or a pharmaceutically acceptable salt thereof, with the exception that if one of $X^3$ or $X^4$ represent $(CH_2)_m$—C(=O)$NX^6X^7$, or $(CH_2)_n$—$NX^6X^7$ then at least one of $X^6$ or $X^7$ is different from H.

17. A method for treating a bacterial infection caused by Escherichia species, Enterobacter species or P.aeruginosa, the method comprising the simultaneous, separate or sequential administration to a patient in need thereof of a kit according to claim 14.

* * * * *